United States Patent [19]
Gaudernack et al.

[11] Patent Number: 5,961,978
[45] Date of Patent: Oct. 5, 1999

[54] THERAPEUTICALLY USEFUL PEPTIDES AND PEPTIDE FRAGMENTS

[75] Inventors: Gustav Gaudernack, Sandvika; Tobias Gedde-Dahl, Snarøya; Jon Amund Eriksen, Porsgrunn, all of Norway

[73] Assignee: Norsk Hydro, a.s., Norway

[21] Appl. No.: 08/433,133

[22] Filed: May 3, 1995

Related U.S. Application Data

[63] Continuation of application No. 07/938,230, Dec. 16, 1992, abandoned.

[30] Foreign Application Priority Data

Feb. 26, 1991 [GB] United Kingdom .................... 9103974
Feb. 21, 1992 [WO] WIPO ...................... PCT/NO92/00032

[51] Int. Cl.⁶ .......................... A61K 39/00; A61K 38/00; A01N 37/18; C07K 2/00
[52] U.S. Cl. .................... 424/185.1; 424/192.1; 424/277.1; 514/2; 530/300; 530/806; 530/324
[58] Field of Search ...................................... 530/300, 806, 530/324; 514/2; 424/185.1, 192.1, 277.1

[56] References Cited

U.S. PATENT DOCUMENTS 5,100,664 3/1992 Doyle et al. .............................. 424/92
5,320,947 6/1994 Cheever et al. ..

FOREIGN PATENT DOCUMENTS 0253325 1/1988 European Pat. Off. .
9111719 9/1991 WIPO .

OTHER PUBLICATIONS

Lanzavecchia, A Science 260: 937–944, 1993.
Deres et al. Nature. 342(6249) 561–564, 1989.
Peace et al, J. Immunol 146 (6) 2059–65, 1991.
*Genes IV* by Benjamin Lewin Oxford University Press, Oxford 1990 p. 820.
D. J. Peace et al. In Fed. Am. Soc. Exp. Biol (1990) p. A2013, Abstract 1854.
S.S. Zamvil et al., J.Exp. Med. (1988) 168:1181–1186.
Jung et al., J.Exp. Med. (1991) vol. 173, pp. 273–276.

*Primary Examiner*—Lila Feisee
*Assistant Examiner*—Yvonne Eyler
*Attorney, Agent, or Firm*—Fitzpatrick, Cella, Harper & Scinto

[57] ABSTRACT

Synthetic peptides and fragments of oncogene protein products which elicit T cellular immunity, for use in cancer vaccines and compositions for anti-cancer treatment.

138 Claims, 33 Drawing Sheets

PROTOCOL:

2 MILLION CELLS/ml x 10ml

20 MICROGRAMS OF FIVE p21 RAS PEPTIDES

1 WEEK

RESTIMULATION: 1 MILLION IRRADIATED AUTOLOGOUS FEEDER CELLS/ml

AND 20 MICROGRAMS OF EACH PEPTIDE FINAL DILUTION

1 WEEK

RESTIMULATION (AS DESCRIBED ABOVE)

1 WEEK

CLONING: 20 TERASAKI PLATES, 1 BLAST PER WELL

CLONES IN 51 OUT OF 600 WELLS

PROBABILITY OF CLONALITY: 97.8%

45 CLONES EXPANDED

29 CLONES CHARACTERIZED

FIG. 1

THERAPEUTICALLY USEFUL PEPTIDES AND PEPTIDE FRAGMENTS

This application is a continuation of application Ser. No. 07/938,230 filed on Dec. 16, 1992, now abandoned.

SUMMARY OF THE INVENTION

This invention relates to synthetic peptides and fragments of oncogene protein products which elicit T cellular immunity, and to cancer vaccines and compositions for anti-cancer treatment comprising said peptides or peptide fragments.

PRIOR ART

From EP272321 it is known to use an oncogene protein product or a fragment thereof for the production of an immunoglobulin specific for the oncogene protein, and thereafter forming a conjugate of said immunoglobulin and an anti-cancer agent to be used in the treatment of cancer.

From EP177814 and EP175360 it is known to produce antibodies against oncogene protein products, such as the p21 protein of ras, only differing in one amino acid in position 12 from the normal protein product. These antibodies may be used for diagnostic or therapeutic purposes. In order to achieve immunogenic peptide fragments of the p21 ras protein, a cysteine residue is inserted between the positions 16 and 17, to which a protein carrier may be attached.

Further, from EP 253325, there are known oncogene-related peptides, which comprise a portion of the amino acid sequence coded for by an oncogene, and antibodies directed to said peptides.

It is further known that one approach to an immunological cancer therapy has been through administration of interleukin-2 combined with specific lymphocytes, so called lymphokine-activated killer cells (LAK cells), or tumour infiltrating lymphocytes (TIL cells). The beneficial effects achieved for some patients having specific cancers are not of a general nature. Further, the side effects experienced by some of the patients are quite unpleasant and sometimes severe. (Steven A. Rosenberg, Scientific American, May 1990, Adoptive Immunotherapy for Cancer.)

It is also known that attempts have been made to develop cancer vaccines based on injection of cancer cells from the patients own cancer or insoluble fragments of said cells or such cells mixed with other nonspecific stimulators of the immune system, such as BCG, interferons or interleukins.

D. J. Peace et al, in Fed. Am. Soc. Exp. Biol. (1990) J4(7), p. A2013 Abstract No 1854, have published results of immunization of mice with a 5–16 fragment of p21 ras protein having a substitution of arginine for glycine at position 12. which resulted in T cell responses. The response was specific for the immunizing peptide and the T cells were capable of responding to the whole protein carrying the same Arg-12 substitution. These results demonstrate that ras peptides are immunogenic in the context of the H-2 molecules of the C57BL/6 mouse strain used in these experiments, and that antigen presenting cells of this mouse strain are capable of processing p21 ras to yield fragments cross reactive with the synthetic peptide used for immunization.

The finding that a mouse strain can be immunized is not relevant for the present invention for the following reasons:

It is a general observation in mice that strains with different H-2 types recognize different sets of peptides from the same protein, [S. S. Zamvil et al, J. Exp. Med, Vol. 168, (1988), 1181–1186], thus a peptide which elicits an immune response in a mouse of one strain, may not stimulate T cells from another, closely related mouse strain. Also in experimental models, T cells from mice, rats and human beings are known to recognize different, non overlapping epitopes of the same protein. The explanation for this is thought to reside in differences between the species in their antigen processing machinery and peptide binding capabilities of their MHC molecules.

From Stefan Jung and Hermann J. Schleusener, J. Exp. Med., Vol. 173, January 1991 it is reported that a synthetic peptide fragment of the amino acids 5–16 of the p21 ras protein having a valine instead of a glycine amino acid in position 12 is recognized by human CD4$^+$ T cells from two healthy persons and that these T cells may be generated as antigen specific T cell lines, which do not cross react with the corresponding peptides derived from the normal p21 ras proteins. In this work it is shown that the human immune system recognizes this single synthetic peptide fragment.

The relevance of this finding is, however unclear since it is known that T cell reactivity against synthetic peptides may differ from T cell reactivity against the whole protein from which the peptides were derived. The explanation for this discrepancy being that equivalents of the synthetic peptide are not formed during proteolytic cleavage/processing of the protein in vivo. Thus, it is of vital importance that the peptide fragment used will elicit specific T cell responses or evoke memory T cell responses to the actual oncogene protein fragment produced by processing and presented by the cancer cell and other antigen presenting cells. The definition of such peptides is a prerequisite for development of cancer vaccines and cancer therapy based on T cell immunity.

TECHNICAL BACKGROUND

The genetic background for the onset of cancer are proto-oncogenes and oncogenes. Proto-oncogenes are normal genes of the cell which have the potential of becoming oncogenes. All oncogenes code for and function through a protein. In the majority of cases they have been shown to be components of signal transduction pathways. Oncogenes arise in nature from proto-oncogenes through point mutations or translocations, thereby resulting in a transformed state of the cell harbouring the mutation. Cancer develops through a multi-step process involving several mutational events and oncogenes. In its simplest form a single base substitution in a proto-oncogene may cause the resulting gene product to differ in one amino acid.

In experimental models involving murine tumours it has been shown that point mutations in intracellular "self"-proteins may give rise to tumour rejection antigens, consisting of peptides differing in a single amino acid from the normal peptide. The T cells recognizing these peptides in the context of the major histocompatibility (MHC) molecules on the surface of the tumour cells are capable of killing the tumour cells and thus rejecting the tumour from the host. (Boon, T. et al, Cell, 1989, Vol. 58, p 293–303)

In the field of human cancer immunology the last two decades has seen intensive efforts to characterize genuine cancer specific antigens.

In particular, effort has been devoted to the analyses of antibodies to human tumour antigens. The prior art suggests that such antibodies could be used both for diagnostic and therapeutical purposes, for instance in connection with an anti-cancer agent. One problem is that antibodies can only bind to tumour antigens that are exposed on the surface of tumour cells. For this reason the efforts to produce a cancer treatment based on the immune system of the body has been less successful than expected.

Antibodies typically recognize free antigen in native conformation and can potentially recognize almost any site exposed on the antigen surface. In contrast to the antibodies produced by the B cells, T cells recognize antigens only in the context of MHC molecules, designated HLA (human leucocyte antigen) in humans, and only after appropriate antigen processing, usually consisting of proteolytic fragmentation of the protein, resulting in peptides that fit into the groove of the MHC molecules. This enables T cells to recognize also peptides derived from intracellular proteins. T cells can thus recognize aberrant peptides derived from anywhere in the tumor cell, in the context of MHC molecules on the surface of the tumor cell, and subsequently can be activated to eliminate the tumor cell harbouring the aberrant peptide.

The HLA molecules are encoded by the HLA region on the human chromosome No 6. The class I molecules are encoded by the HLA A, B and C subloci, and the class II molecules are encoded by the DR, DP and DQ subloci. All the gene products are highly polymorphic. Different individuals thus express distinct HLA molecules that differ from those of other individuals. This is the basis for the difficulties in finding HLA matched organ donors in transplantations. The significance of the genetic variation of the HLA molecules in immunobiology is reflected by their role as immune-response genes. Through their peptide binding capacity, the presence or absence of certain HLA molecules governs the capacity of an individual to respond to peptide epitopes. As a consequence, HLA molecules determine resistance or susceptibility to disease.

T cells may control the development and growth of cancer by a variety of mechanisms. Cytotoxic T cells, both HLA class I restricted CD8+ and HLA Class II restricted CD4+, may directly kill tumour cells carrying the appropriate tumour antigens. CD4+ helper T cells are needed for cytotoxic T cell responses as well as for antibody responses, and for inducing macrophage and LAK cell killing.

Although the prior art has identified many oncogenes and their protein products, and a recently published study has shown that the T cell repertoire of a healthy person includes T cells with a specificity against a synthetic peptide fragment derived from one p21 ras oncogene product, no previous studies have defined the correct antigens or antigenic sites giving rise to tumour specific T cell immunity.

Thus the present invention is based on the idea that another possible approach for combatting cancer is by using the body's own immune system through an activation and strengthening of the immune response from specific T cells.

DEFINITION OF THE INVENTION

The present invention involves the discovery of synthetic peptides and peptide fragments of oncogene proteins which elicit specific T cell responses against cancer cells which harbour an oncogene.

The peptides and fragments according to this invention are characterized in that they a) have a point of mutation or translocation as compared to the corresponding fragment of the proto-oncogene protein; and b) correspond to, completely cover or are a fragment of the processed oncogene protein fragment as presented by the cancer cell or other antigen presenting cells (APC); and c) induce specific T cell responses to the actual oncogene protein fragment produced by the cell by processing and presented by the HLA molecule.

Since these mutations give rise to the transforming capacity of oncogenes, they are pivotal in the development of cancer. By raising specific T cell responses against these mutations, control of the development and growth of the tumour cells carrying the mutation is possible. Thus for the first time it is possible to develop prophylaxis and therapy directed against the specific genetic alterations in neoplastic cells.

DETAILED DESCRIPTION OF THE INVENTION

One purpose of the present invention is to develop a vaccine to prevent the establishment of cancers carrying the most commonly observed oncogene mutations, based partly or solely on synthetic peptides or peptide fragments of oncogene proteins which produce T cell immunity against the oncogene's gene product.

Another purpose of the present invention is to produce a cancer therapy for cancers having the said mutations in their proto-oncogenes, based on the T cell immunity which may be induced in patients by stimulating their T cell immunity either in vitro or in vivo with the peptides according to the present invention.

In order for a cancer vaccine and methods for specific cancer therapy based on specific T cell immunity to be effective, three conditions must be met:

1. The peptides used must correspond to, completely cover and/or be an active fragment of the processed oncogene protein fragment as presented by the cancer cell or other antigen presenting cells,
2. The peptides used must be bound to a HLA molecule in an immunogenic form, and
3. T-cells capable of recognizing and responding to the HLA peptide complex must be present in the circulation of the subject.

It has been established that all these conditions are met for the peptides according to the present invention. The peptides according to the present invention give rise to specific T cell immune responses in vitro. The HLA molecules capable of binding each of the peptides were determined. Evidence for a general binding of ras peptides to DR and DQ molecules was further obtained in direct binding assays with purified DR and DQ molecules. It has been established that the synthetic peptides or peptide fragments according to this invention correspond to the processed oncogene protein fragments. This is exemplified with synthetic p21 ras peptide fragments having a mutation in position 61. Specific T cell memory responses were evoked in vitro by these synthetic peptides. This is a clear indication that the cancer patient's T cells had been activated by the same or very similar peptide fragments in vivo.

It has recently been established that the T cell repertoire of a healthy person encompass T cells with a specificity against a single synthetic peptide having a mutation in position 12, and it was further investigated if this phenomenon was of a general nature. Thus, a complete panel of peptides representing the known, common p21 ras mutations in the positions 12, 13 and 61 were teeted looking for T cells being activated by these peptide fragments.

In the present description and claims, the amino acids are either represented by their full name or by the three letter abbreviation as known in the art.

EMBODIMENTS

The peptides according to this invention are synthetic peptides corresponding to and/or encompassing the processed peptide being presented by the cancer cell or other antigen presenting cells, including a mutation in one or more positions corresponding to the oncogene mutation, and giving rise to T cell immunity against the oncogene protein. The amino acid at the position of the point of mutation may be any amino acid except the amino acid found in the normal proto-oncogene encoded protein, but preferred are the amino acids found in oncogene proteins.

The peptides according to this invention further include fragments having one or several amino acid substitutions at the flanks of the point of mutation or translocation.

Transforming ras genes are the oncogenes most frequently identified in human cancer, with an overall incidence estimated to be around 10–20%. The transforming genes carry mutation in position 12, 13 and 61 in the ras gene product p21.

According to one aspect of this invention, the synthetic peptides are fragments including at least one of the positions 12, 13 and 61 of the oncogene protein ras p21, having the same amino acid sequence.

The amino acid in the position 12 may be any amino acid except Gly, which is found in the protein product encoded for by the proto-oncogene, when the remainder of the sequence corresponds to the normal proto-oncogene. One group of preferred peptides according to this invention are the peptides p113–p119, the amino acid sequences of which will appear from Table 8, or fragments thereof, which will elicit a T cell response against the oncogene's protein product.

The amino acid in the position 13 may be any amino acid except Gly, which is found in the protein product encoded for by the proto-oncogene. One group of preferred peptides according to this invention are the peptides p120–p121, the amino acid sequences of which will appear from Table 8, or fragments thereof, which will elicit a T cell response against the oncogene's protein product.

The amino acid in the position 61 may be any amino acid except Gln, which is found in the protein product encoded for by the proto-oncogene. One group of preferred peptides according to this invention are the peptides shown in Table 9, or fragments thereof, which will elicit a T cell response against the oncogene's protein product.

Preferred peptides according to this invention are peptides or fragments of p21 ras proteins which are selected from the amino acids 1–25 and which have at least one mutation in the positions 12 and/or 13. The sequence of the amino acids 1–25 of the normal p21 ras protein having a Gly in both position 12 and 13 will appear from Table 6.

Other preferred peptides according to this invention are peptides or fragments of p21 ras proteins which are selected from the amino acids 45–72, especially 51–67 and which have at least one mutation in position 61. The sequence of the amino acids 45–72 of the normal p21 ras protein having a Gln in position 61 will appear from Table 6.

Other peptides according to the present invention are peptide fragments of p53 comprising at least mutations in position 273, in which position any amino acid except Arg may be located.

Further peptides according to the present invention are peptide fragments of the bcr-abl fusion protein p190, in which exon 3 of bcr and exon 2 of abl are joined, or bcr-abl fusion protein p210, in which exon 2 of bcr and exon 2 of abl are joined.

Other peptides are peptide fragments of a bcr-abl fusion protein, in which exon c3 of bcr and exon 2 of abl are joined.

Preferred peptides of this group will comprise the following fragments or parts thereof:

Ile-Pro-Leu-Thr-Ile-Asn-Lys-Glu-Glu-Ala-Leu-Gln-Arg-Pro-Val-Ala-Ser-Asp-Phe-Glu (SEQ ID NO. 95)

Ala-Thr-Gly-Phe-Lys-Gln-Ser-Ser-Lys-Ala-Leu-Gln-Arg-Pro-Val-Ala-Ser-Asp-Phe-Glu (SEQ ID NO. 96)

Ala-Phe-Asp-Val-Lys-Ala-Leu-Gln-Arg-Pro-Val-Ala-Ser-Asp-Phe-Glu (SEQ ID NO. 97)

Still other preferred peptides are fragments of ret fusion protein, comprising the following sequence or parts thereof: Leu-Arg-Lys-Ala-Ser-Val-Thr-Ile-Glu-Asp-Pro-Lys-Trp-Glu-Phe (SEQ ID NO. 98)

Still other preferred peptides are fragments of the EGF receptor fusion protein comprising the following sequence or parts thereof: Ser-Arg-Ala-Leu-Glu-Glu-Lys-Lys-Gly-Asn?-Tyr-Val-Val-Thr-Asp-His-Gly (SEQ ID NO. 99)

Still other preferred peptides are fragments of the retinol receptor fusion protein comprising the following sequence or parts thereof: Leu-Ser-Ser-Cys-Ile-Thr-Gln-Gly-Lys-Ala-Ile-Glu-Thr-Gln-Ser-Ser-Ser-Glu-Glu (SEQ ID NO: 100)

The present invention further includes larger fragments carrying a few amino acid substitutions at either the N-terminal or the C-terminal end, as it has been established that such peptides may give rise to T cell clones having the appropriate specificity.

The peptides or fragments according to the present invention may be symmetrical or unsymmetrical around the position where the mutation is found in the oncogene proteins.

Further it is considered that the peptides may be administered together, either simultaneously or separately, with compounds such as cytokines, i.e. interleukin-2 or the like in order to strengthen the immune response as known in the art.

The invention includes, but is not limited to these specific peptides and any synthetic peptides containing or overlapping these sequences or variations therein, including peptides with amino acid substitutions that retain or enhance the activity documented.

The peptides according to the present invention can be used in a vaccine or a therapeutical composition either alone or in combination with other materials, such as for instance in the form of a lipopeptide conjugate which as known in the art may induce high-affinity cytotoxic T lymphocytes, (K. Deres, Nature, Vol.342, (November 1989)).

The peptides or peptide fragments according to the present invention may be useful to include in either a synthetic peptide or recombinant fragment based vaccine.

The peptides of the present invention are particularly suited for use in a vaccine capable of safely eliciting either type of immunity:

(1) the peptides are synthetically produced and therefore do not include transforming cancer genes or other sites or materials which might produce deleterious effects, (2) the peptides may be used alone to induce cellular immunity, (3) the peptides may be targeted for a particular type of T cell response without the side effects of other unwanted responses.

The peptides or fragments according to the present invention can be included in pharmaceutical compositions or in vaccines together with usual additives, diluents, stabilizers or the like as known in the art.

According to this invention, a pharmaceutical composition or vaccine may include the peptides or fragments alone or in combination with at least one pharmaceutically acceptable carrier or diluent.

Further a vaccine composition can comprise a selection of peptides having the most common mutations as found in oncogene proteins.

Further a vaccine composition can comprise a peptide selected for one cancer, which vaccine would be administered to persons belonging to a high risk group for this particular cancer.

The peptides and peptide fragments according to this invention may be produced by conventional processes as known in the art, and this is elucidated in the description of the synthesis below.

As mentioned above a cancer vaccine according to the present invention may be administered to persons belonging to a high risk group for one definite cancer connected to one or several oncogenes. Examples of oncogenes found in human tumours will appear from Table 5.

The cancer vaccine according to this invention may further be administered to the population in general for example as a mixture of peptides giving rise to T cell immunity against various common cancers.

A cancer therapy according to the present invention may be administered both in vivo or in vitro having as the main goal the raising of specific T cell lines or clones against the gene product of the oncogene responsible for the cancer type with which the patient is afflicted.

BIOLOGICAL EXPERIMENTS

DESCRIPTION OF THE FIGURES

FIG. 1 shows the protocol for eliciting p21 ras peptide specific T cell responses in normal donors in vitro, and for cloning of such cells. Mononuclear cells from peripheral blood (PBMC) were isolated from defibrinated blood by centrifugation on Lymphoprep (Nycomed, Oslo, Norway). Washed PBMC were resuspended in RPMI 1640 (Gibco, Paisley, Scotland) supplemented with 100 IU/ml penicillin, streptomycin (100 µg/ml) and 15% autologous serum, and the indicated amounts of synthetic peptides and incubated in a 5% $CO_2$ incubator at 37° C. The structure of the peptides used is given in Table 1. All of the peptides representing mutations in position 12 and 13 contain an additional alanine or valine in the C-terminus.

For the T cell cloning procedure, T cell blasts were seeded at 1 or 10 blasts per well in Terasaki plates in the same peptide containing medium as above. Each well contained 25000 irradiated (2000R) autologous PBMC as feeder cells and was supplemented with recombinant human IL-2 (Amersham, England) at a final concentration of 20 U/ml, in a total volume of 20 µl. T cell growth was evaluated microscopically on day 5–6 and transferred to 96 well plates (Costar, Cambridge, Mass., USA). Each well contained 100000 fresh, irradiated autologous PBMC as feeder cells, as well as peptides and IL-2 as above, in a final volume of 120 µl. Growing clones were further expanded in 24 well plates on day 3–5 after transfer from 96 well plates, in the same manner as described above, and restimulated weekly with fresh irradiated feeder cells, peptides and IL-2. Further expansion of the clones was done in medium containing only IL-2, and finally in medium without peptides or IL-2.

FIG. 2 and FIGS. 2a–2e show the specificity of the T cell clones I, B, E and F in T cell proliferation assays. Assays were set up in triplicate in 96 well plates, with the five peptides present in the original peptide mixture as stimulating antigens. The wells contained 50000 irradiated (8000 R) autologous EBV transformed B cells as antigen presenting cells (APC).

Cultures were incubated for 2 days at 37° C. in a 5% $CO_2$ incubator, and pulsed overnight with 1 µCi of $^3$H-thymidine (Amersham, England) per well before harvesting onto glass fibre filters by an automated cell harvester (Scatron, Lierbyen, Norway). Thymidine incorporation into DNA was quantitated by liquid scintillation counting using an LKB 1205 Betaplate Liquid Scintillation counter. Data are given as medians of triplicate cultures. Controls included T cell clones cultured alone, or with APC in the absence of peptides. The panels are scaled according to the magnitude of the positive response.

FIGS. 3a–3d show the results of blocking experiments with clones I, B, E and F using the monoclonal antibodies L243, specific for HLA-DR and FN81.1.1, specific for HLA-DQ. Proliferation assays were as described in FIG. 2, with the exception that the APC were preincubated for 30 minutes at 37° C. with the indicated concentration of monoclonal antibody before the addition of T cells and peptides to the incubation mixture. Data are expressed as described in FIG. 2.

Figure 4:
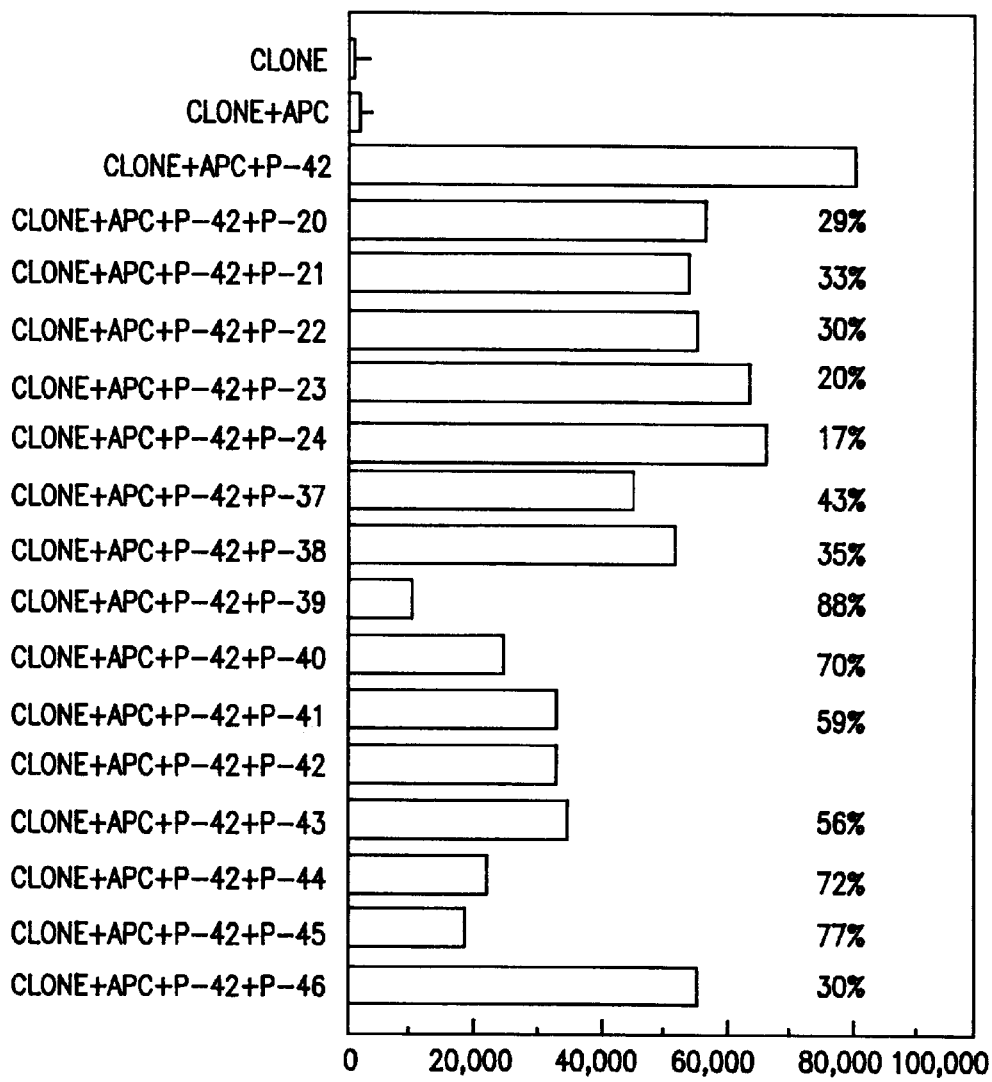

FIG. 4 shows peptide inhibition studies with clone I as indicator responder cell. Conditions were as described in FIG. 2, except that 10 µmolar concentration of stimulatory peptide (peptide 42) and 250 µmolar concentration of the inhibitory peptides were used. APC were preincubated for 30 minutes at 37° C. with inhibitory peptides before the addition of stimulatory peptides and T cells. Data are expressed as in FIG. 2. (Note: peptide 42 at a concentration of 250 µmolar appears to inhibit clone I. This is also evident from the dose response curve of this clone with peptide 42 (data not shown).)

Figure 5:
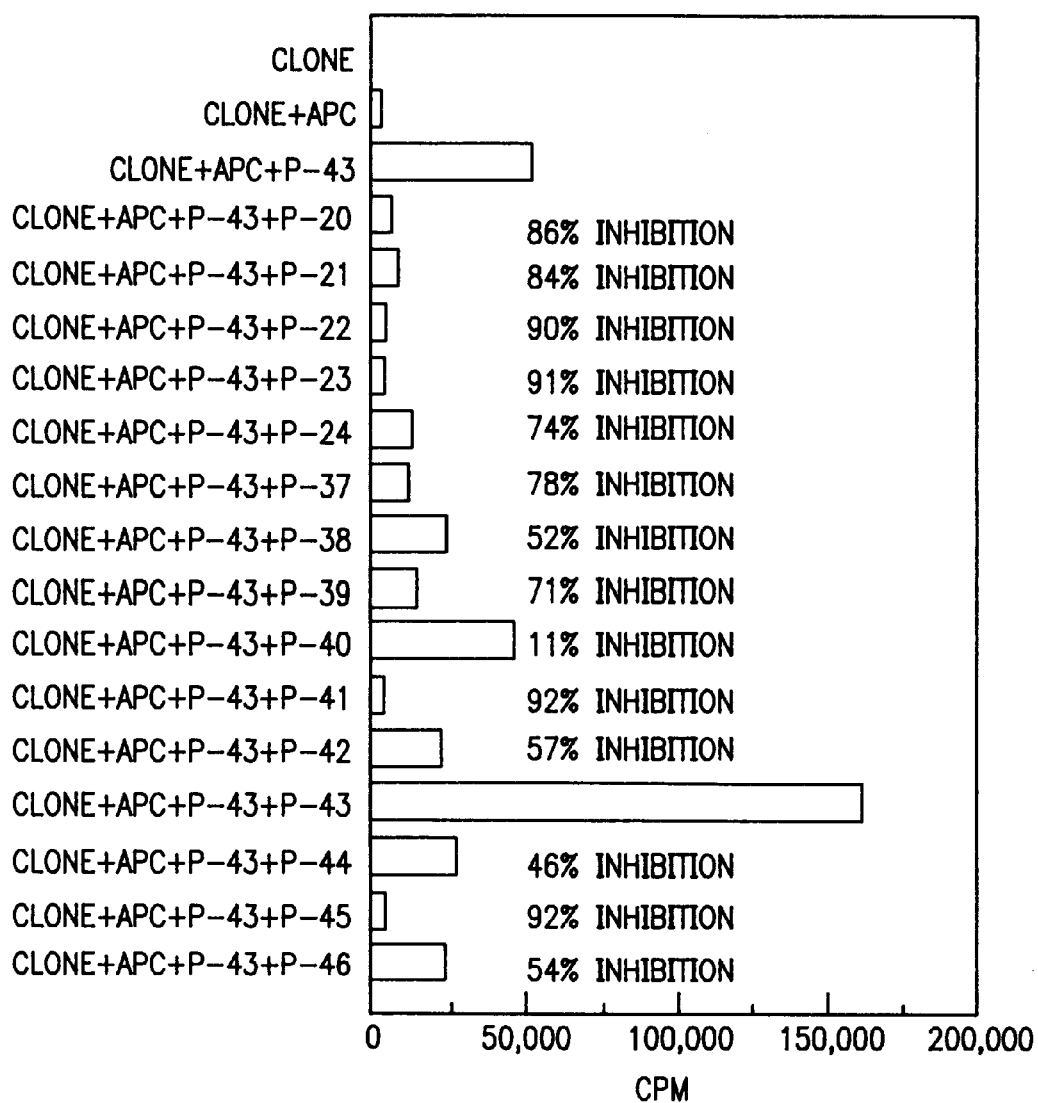

FIG. 5 shows similar results as in FIG. 4, this time inhibition of the response of clone E to peptide 43 is recorded. Conditions are otherwise as described in FIG. 4.

Figure 6:
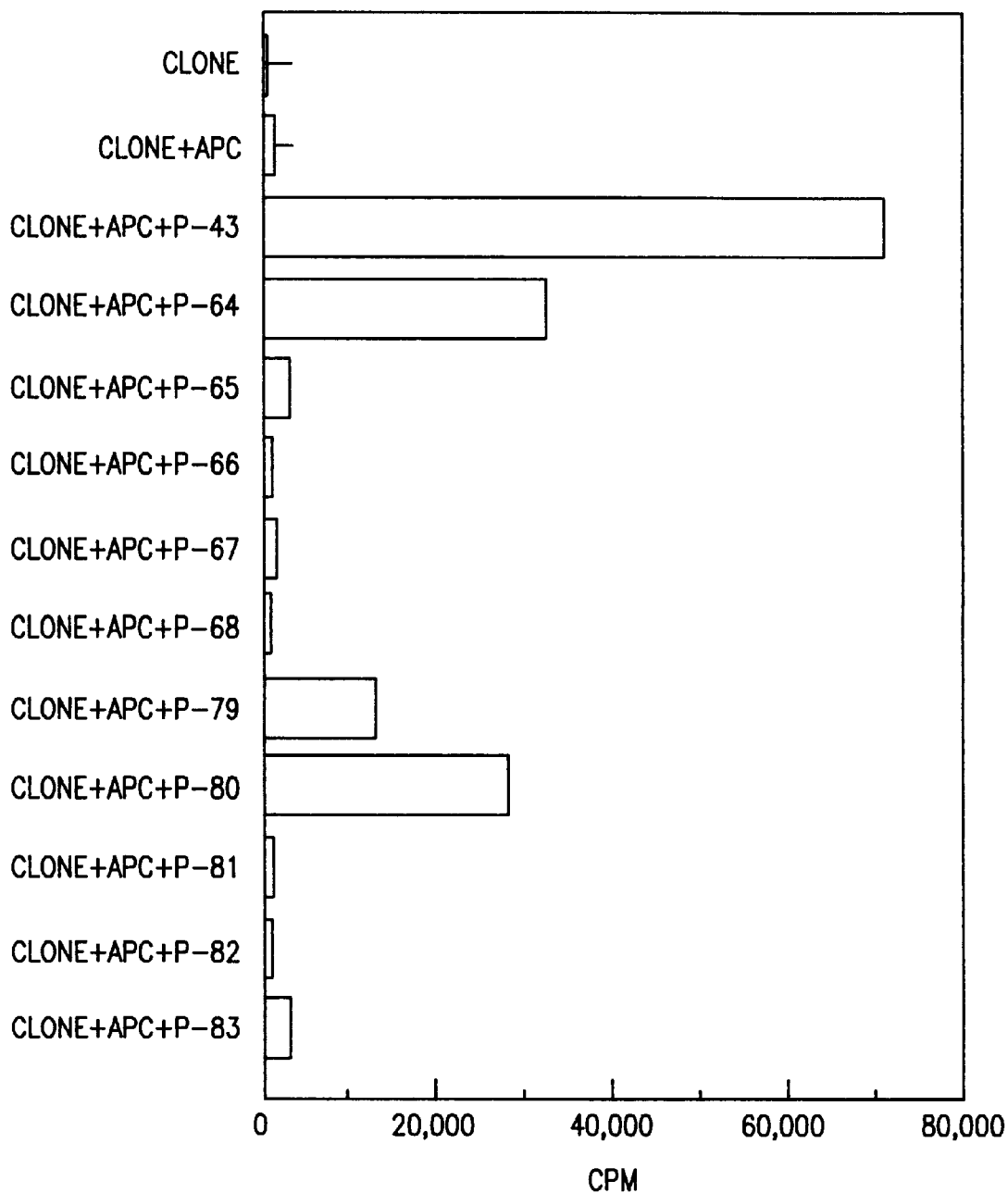

FIG. 6 shows the response of clone E to truncated forms of peptide 43. The peptides were truncated from the N-terminal and C-terminal end as seen in Table 2. The conditions of the assay were as described in FIG. 2. Each peptide was present in a concentration of 10 µmolar, and the number of responder T cells and APC was 50000.

Figure 7:
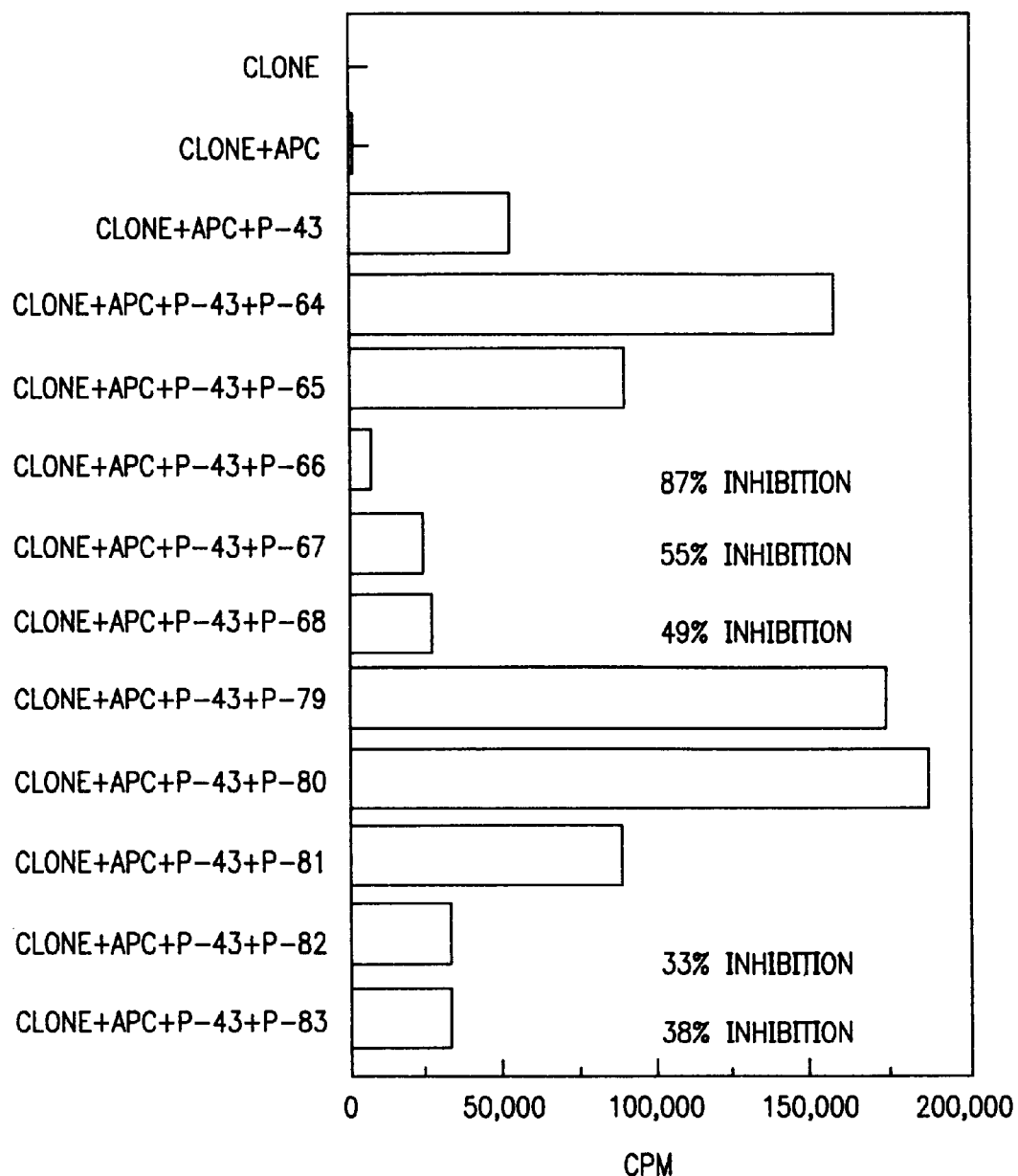

FIG. 7 shows peptide inhibition studies with clone E as indicator responder cell, and using the same truncated forms of peptide 43. Five µmolar concentration of stimulatory peptide (peptide 43) and 250 µmolar of the inhibitory peptides were used. Conditions were otherwise as described in FIG. 4. Note: Peptide 65 and 81 are non-stimulatory in a concentration of 10 µmolar (FIG. 6), but are stimulatory in a concentration of 250 µmolar.

Figure 8:
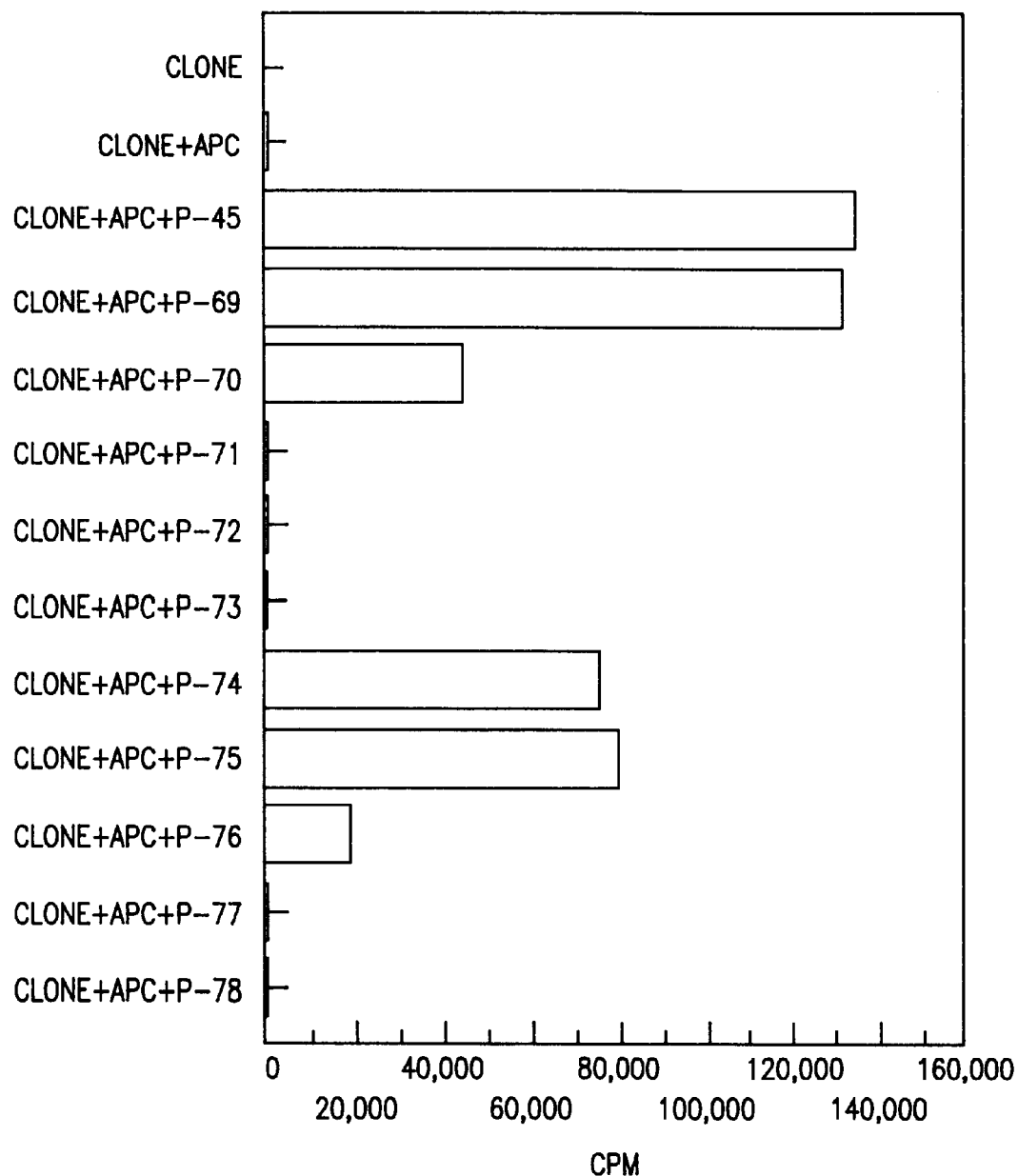

FIG. 8 shows the response of clone F to truncated forms of peptide 45. The structure of the peptides is given in Table 2. The conditions of the assay were exactly as described in FIG. 6.

Figure 9:
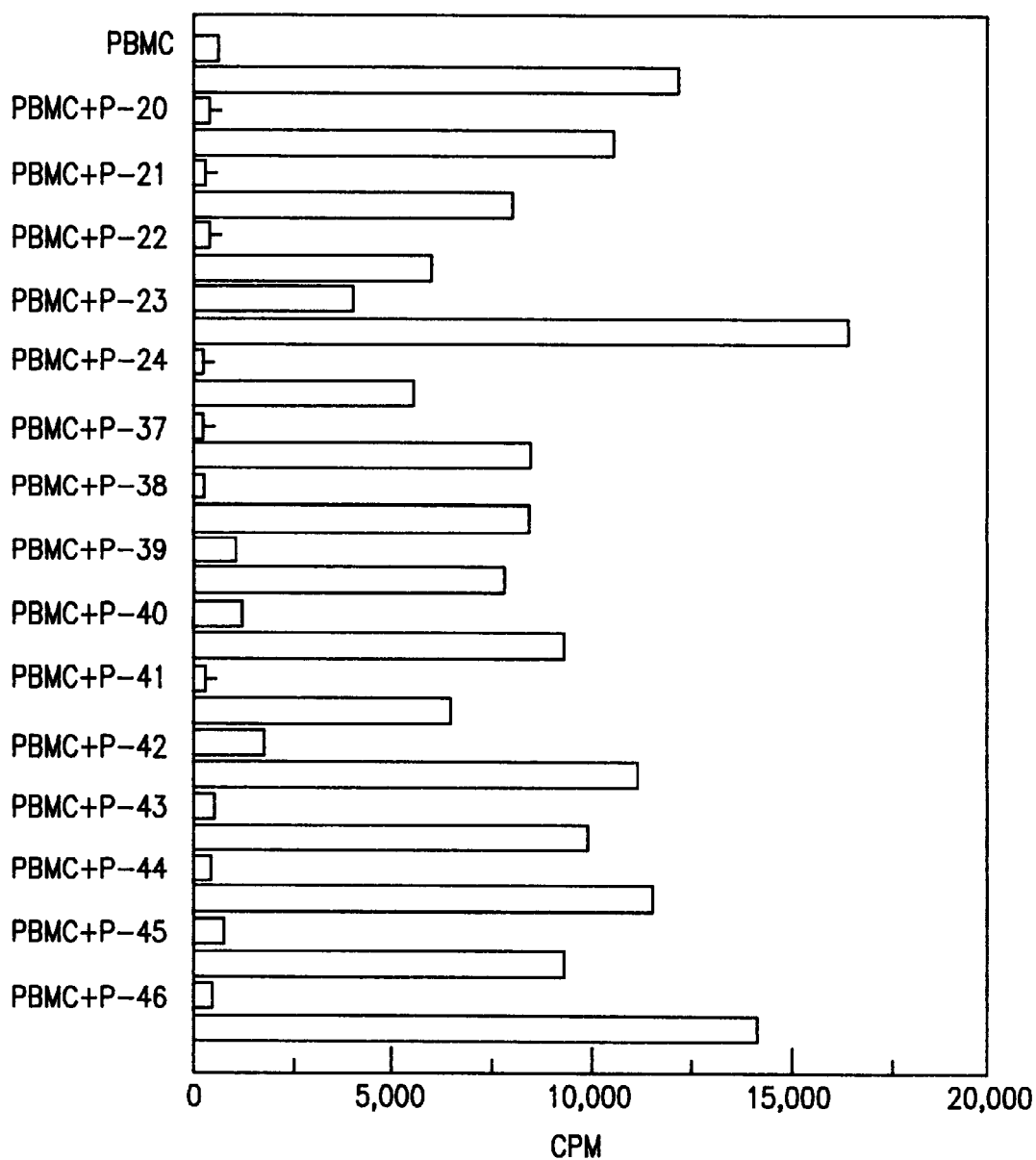

FIG. 9 shows the results of stimulation of PBMC from a patient with follicular thyroid carcinoma with the whole panel of p21 ras derived peptides. PBMC, 100000 cells/well in 96 well plates were incubated with 100 µg/ml of each peptide in the absence of (first column) or presence of (second column) 1 U/ml of recombinant human IL-2. $^3$H-thymidine (1 µCi) was added on day 6, and the cultures harvested and processed on day 7 as described in FIG. 2. Results are given as medians of triplicates. Controls were PBMC cultured alone or in the presence of recombinant IL-2.

Figure 10:
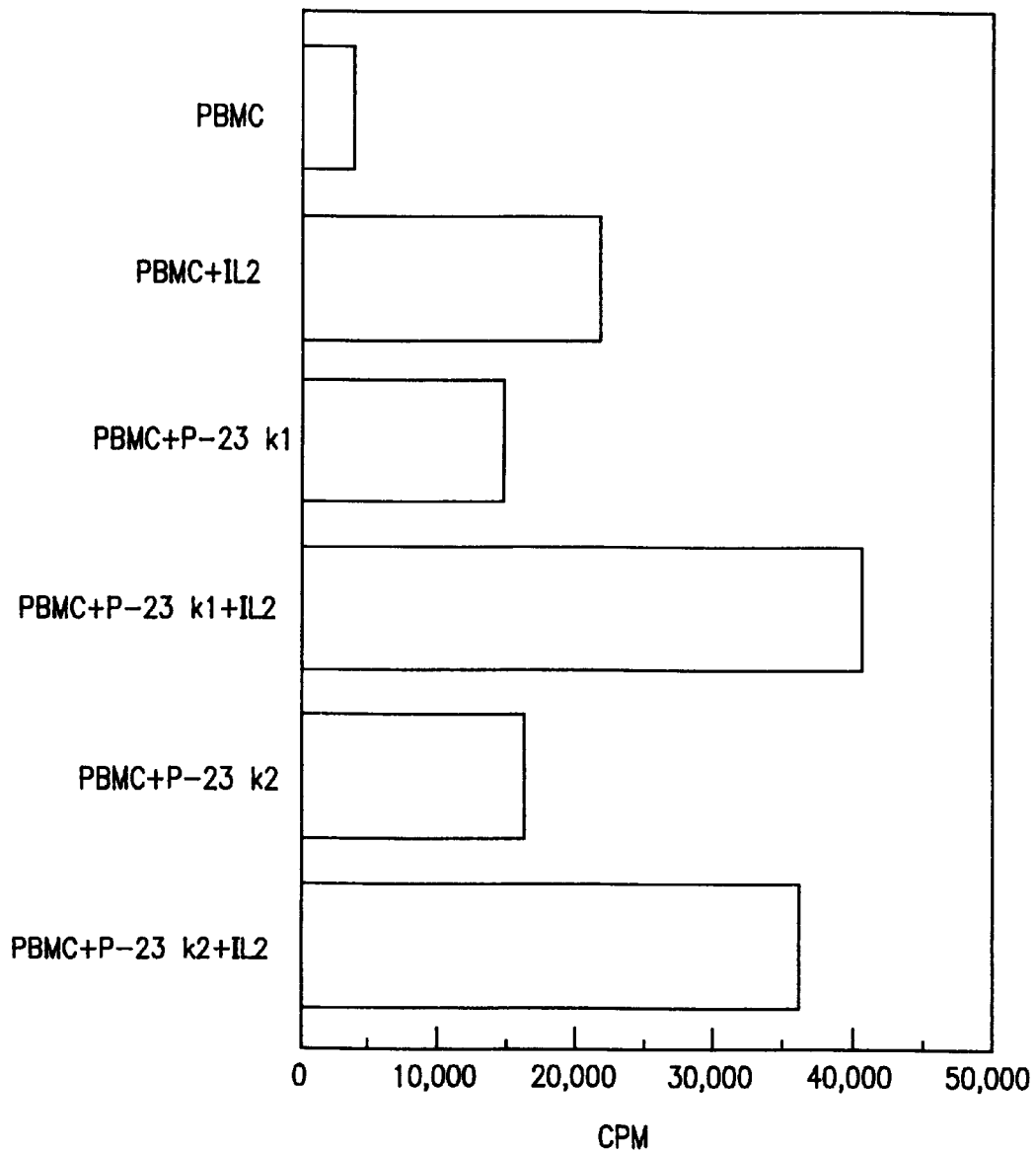

FIG. 10 shows the response of PBMC from the same donor as in FIG. 9 to peptide 23, in the presence or absence of IL-2. Conditions are as in FIG. 9, except that 200000 cells per well was used, as well as two different doses of peptide.

Figure 11:
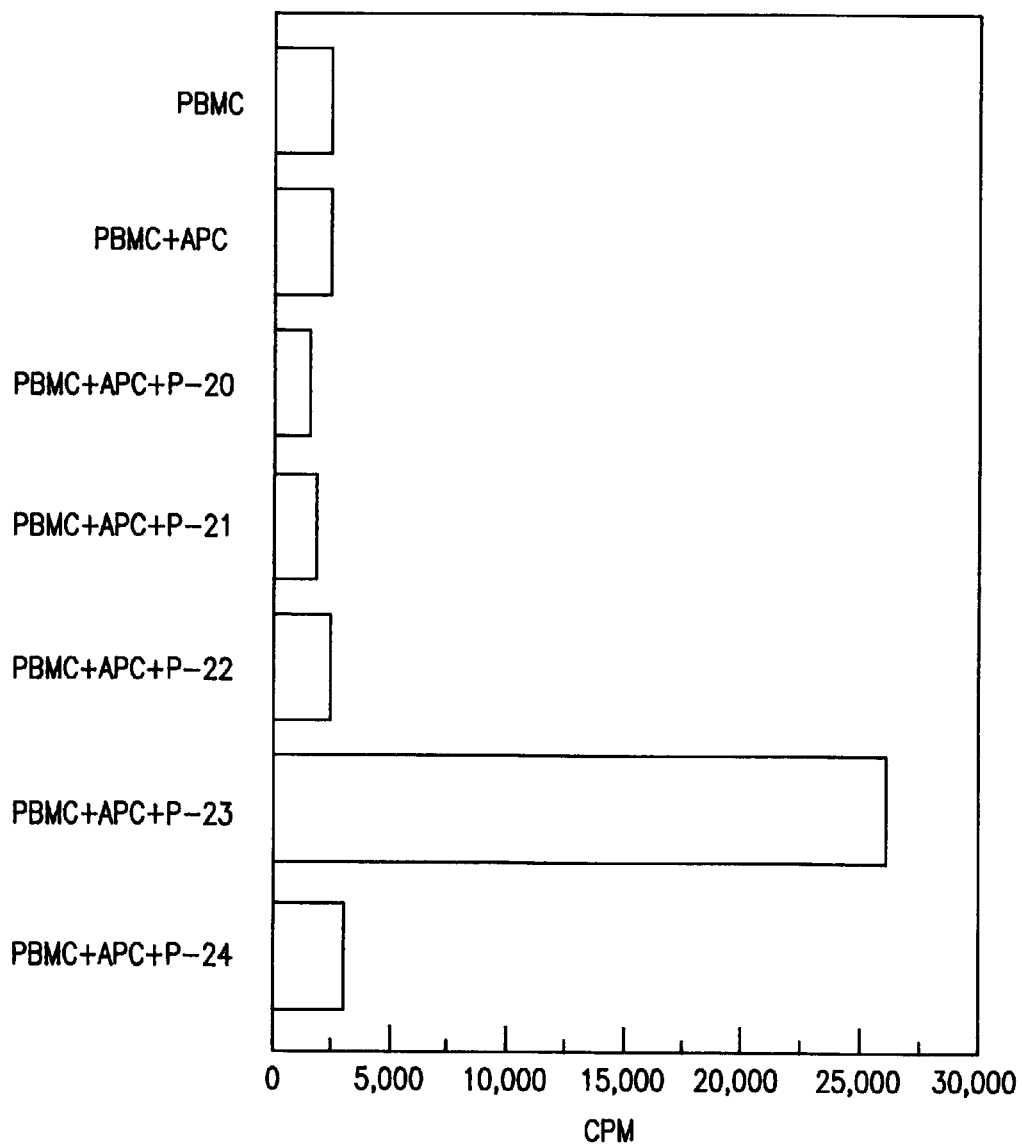
Figure 12A:
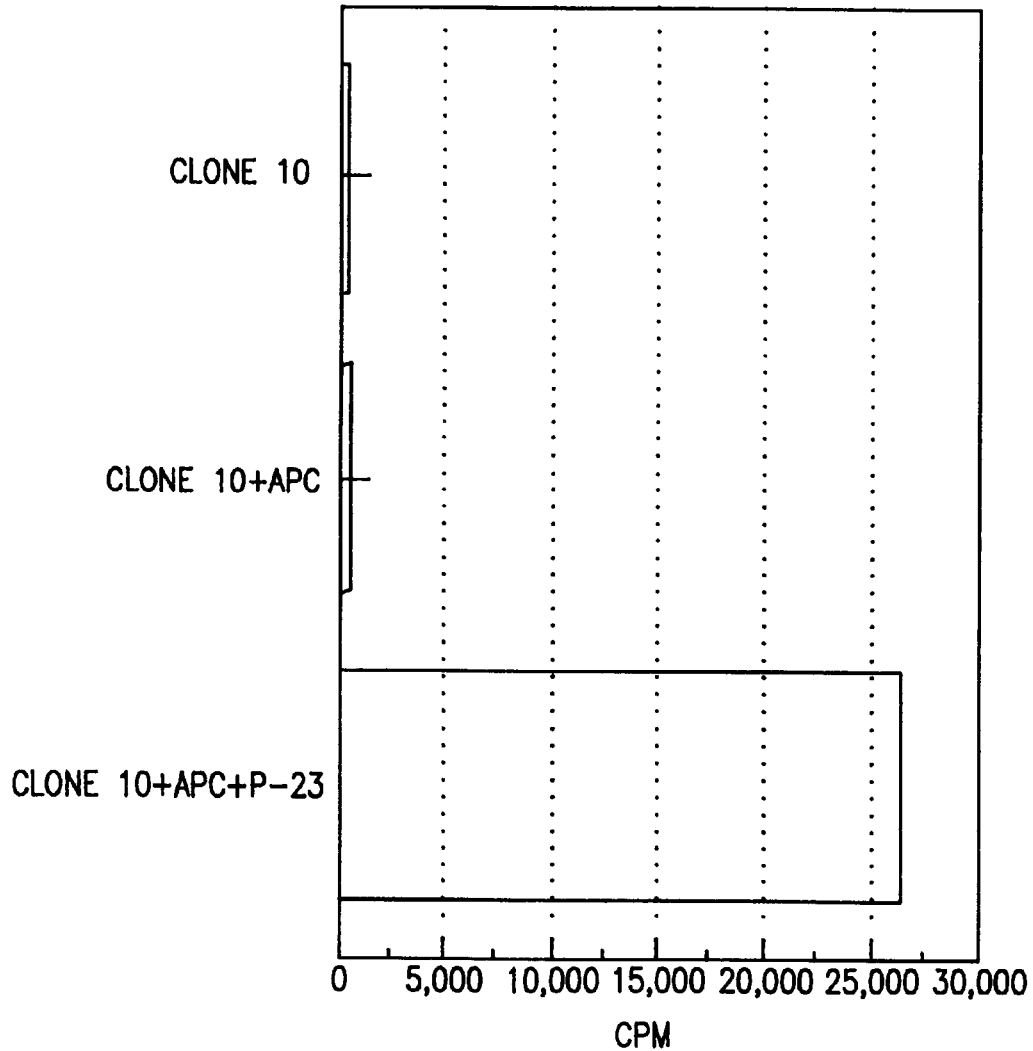
Figure 12B:
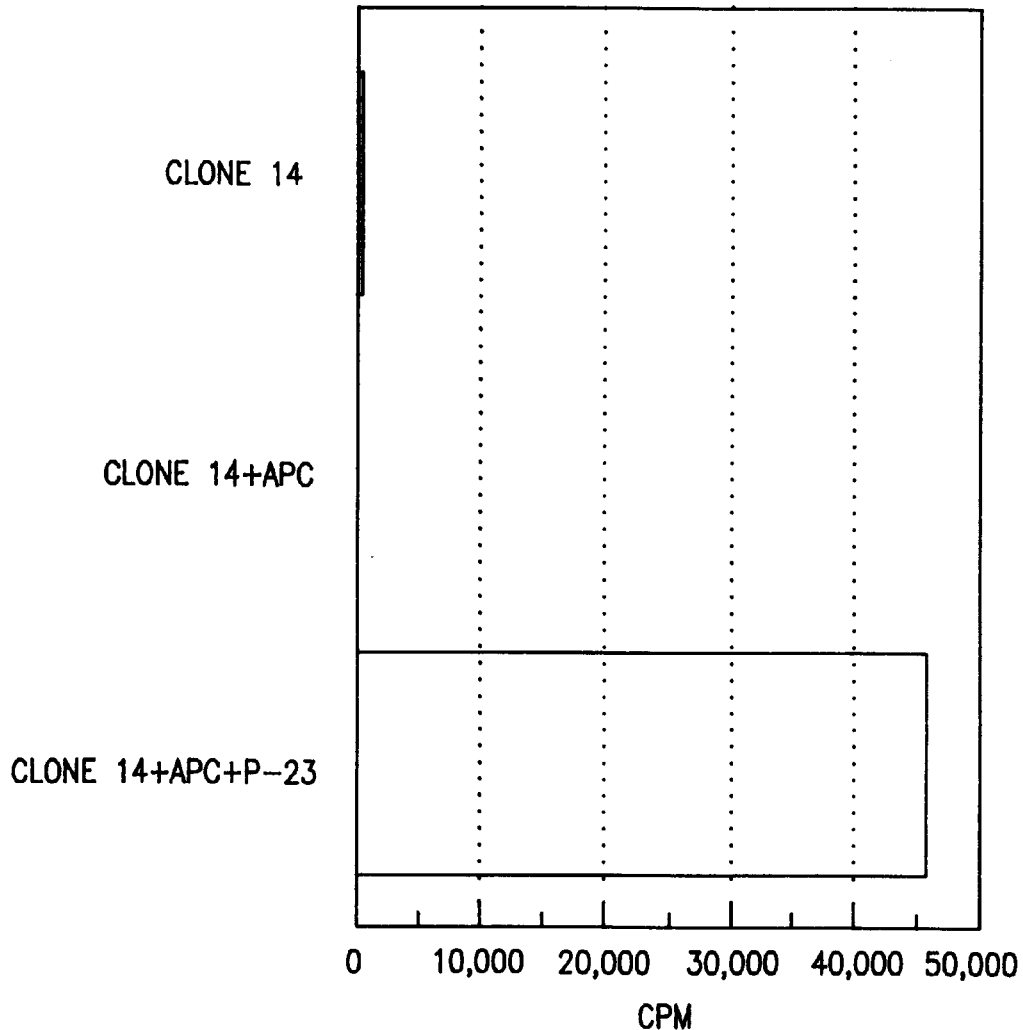
Figure 12C:
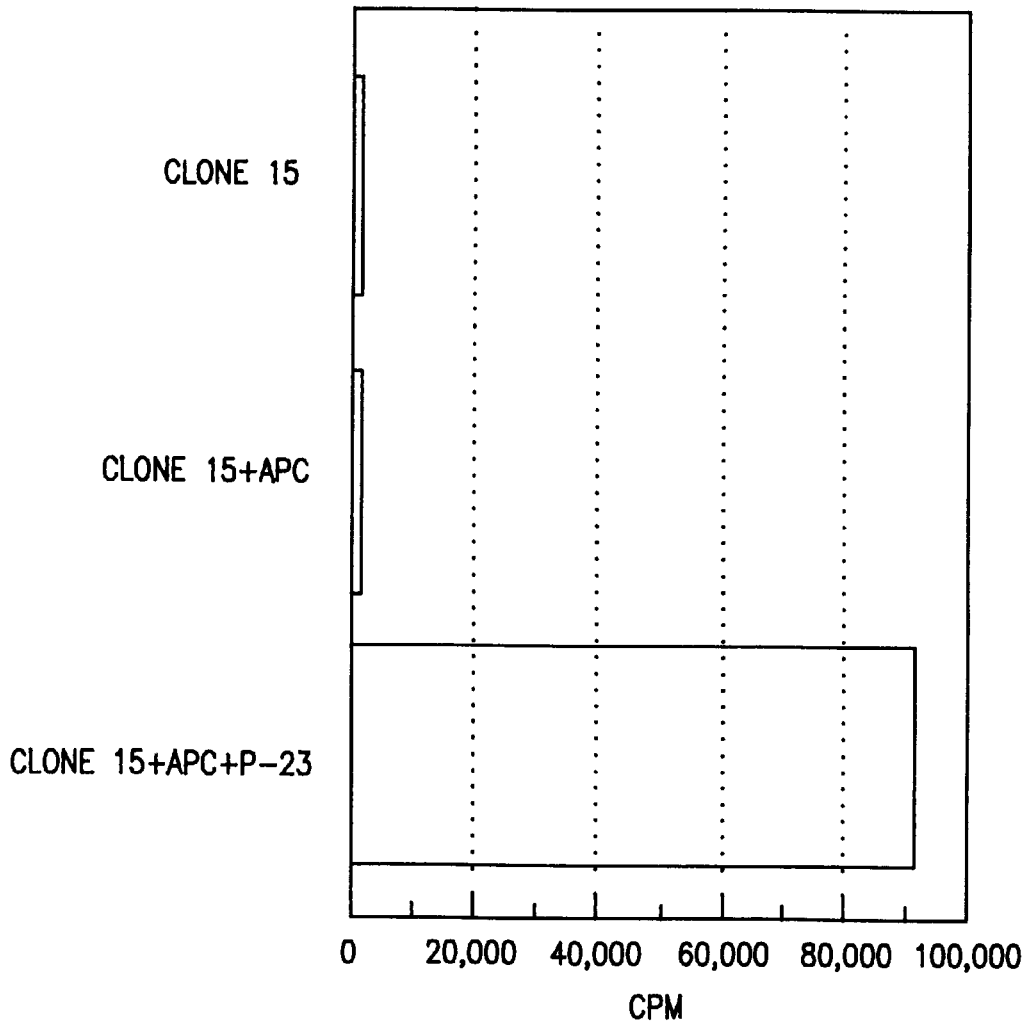
Figure 12D:
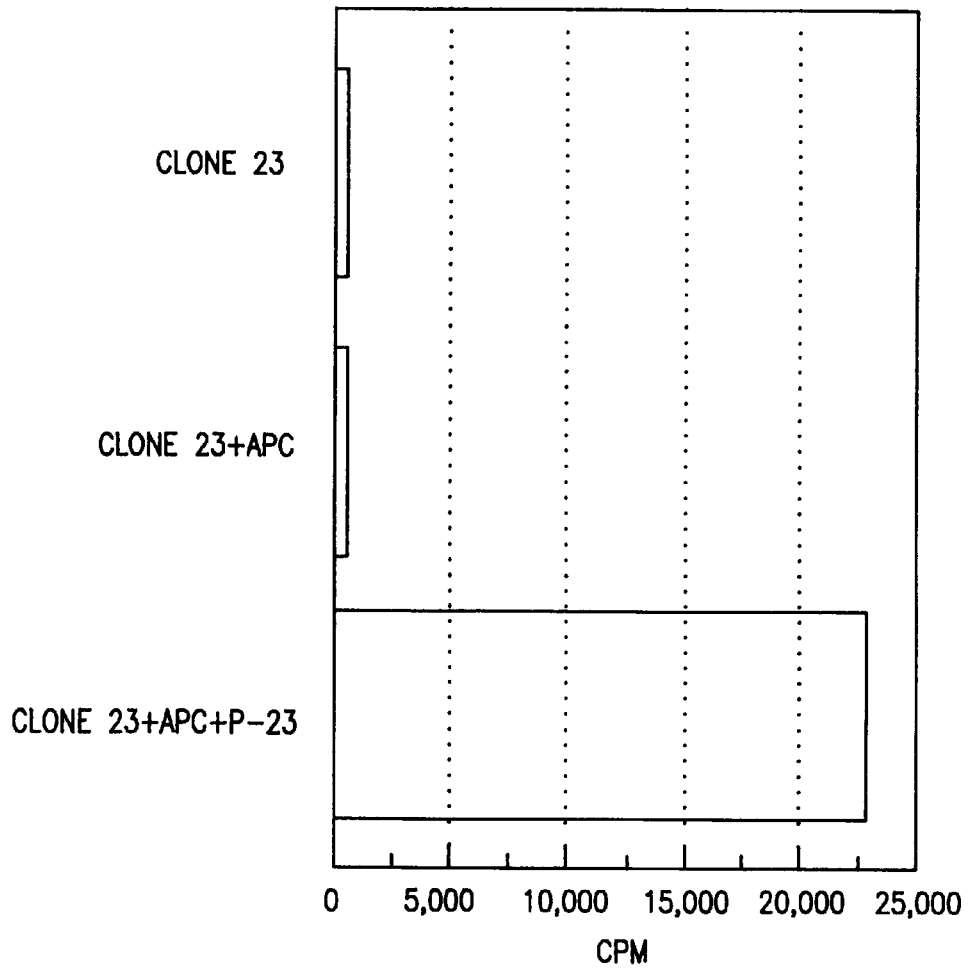

FIG. 11 shows the response of a secondary T cell culture derived from the patient described in FIG. 9 and 10 to five peptides representing the amino acid sequence around position 61 of the normal and mutated p21 ras proteins.

Conditions were as described in FIG. 2, except that 25000 of the responder cells abd APC were used, and the peptide concentration was 200 µg/ml.

FIGS. 12a–12d show the reactivity of the T cell clones 10, 14, 15, and 23 towards peptide 23. Conditions of the assay were as described in FIG. 2, except that 50000 irradiated allogeneic HLA-DQ identical PBMC were used as APC, and peptide concentration was 50 µg/ml.

Figure 13:
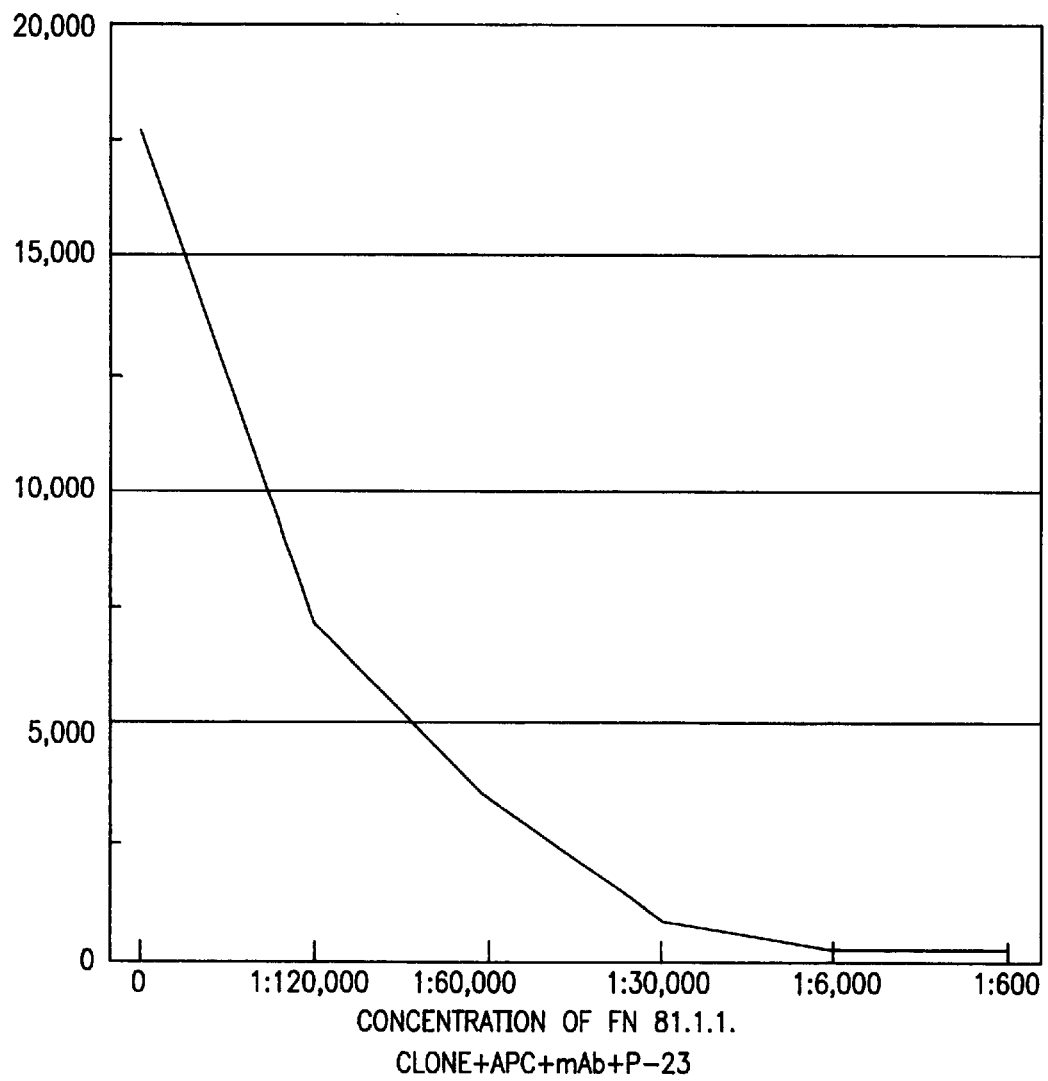

FIG. 13 shows the results of blocking experiments with clone 14, using a monoclonal antibody FN81.1.1., specific for HLA-DQ. Conditions were as described in FIG. 2 and 3.

Figure 14:
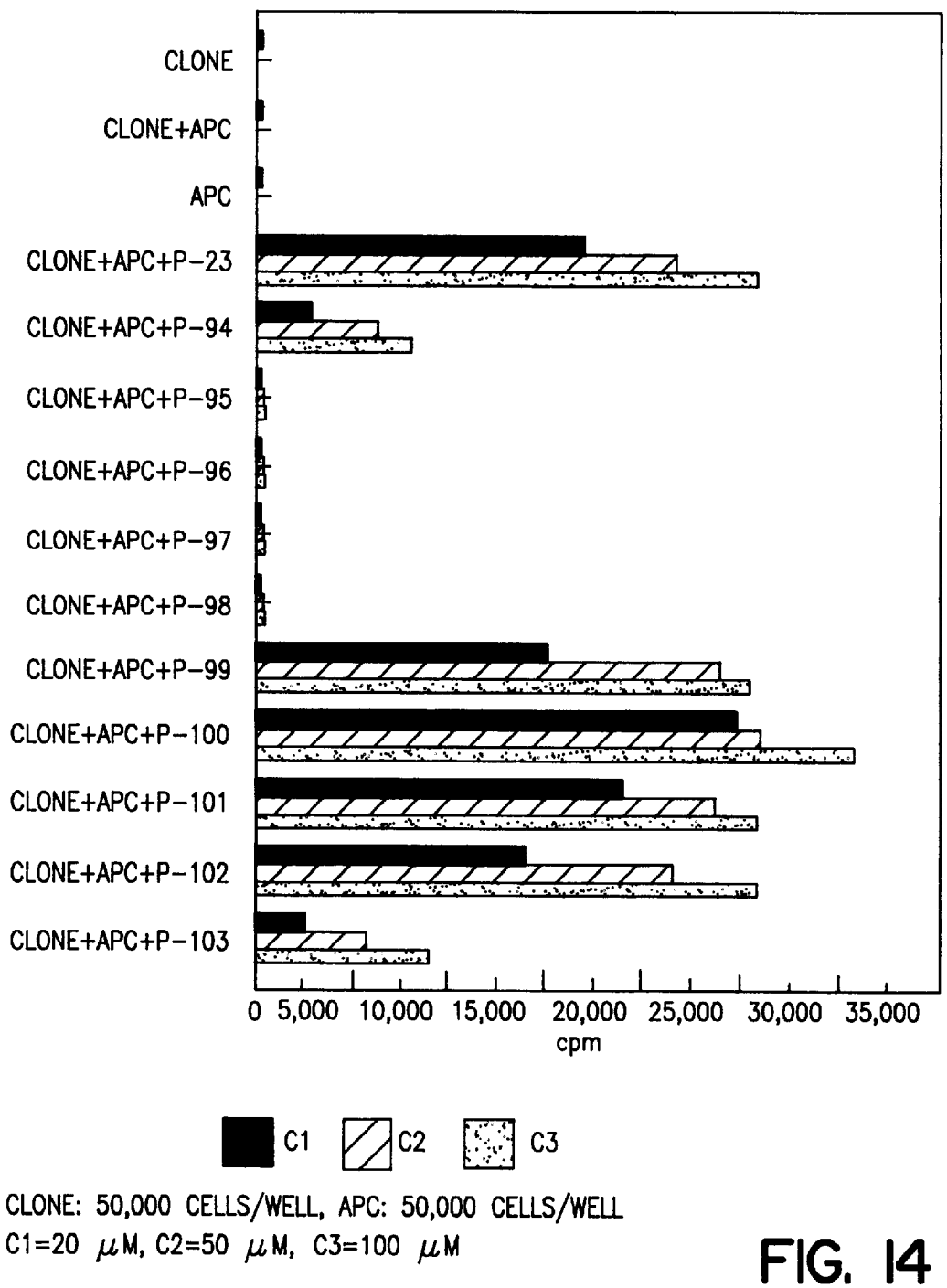

FIG. 14 shows the response of clone 15 to truncated forms of peptide 23. The peptides were truncated from the N-terminal and C-terminal end as seen in Table 7. The conditions of this assay were as described in FIG. 2, with the exception that each peptide was used in final concentration of 20, 50 and 100 µmolar. The number of responder cells and APC was 50 000.

Figure 15:
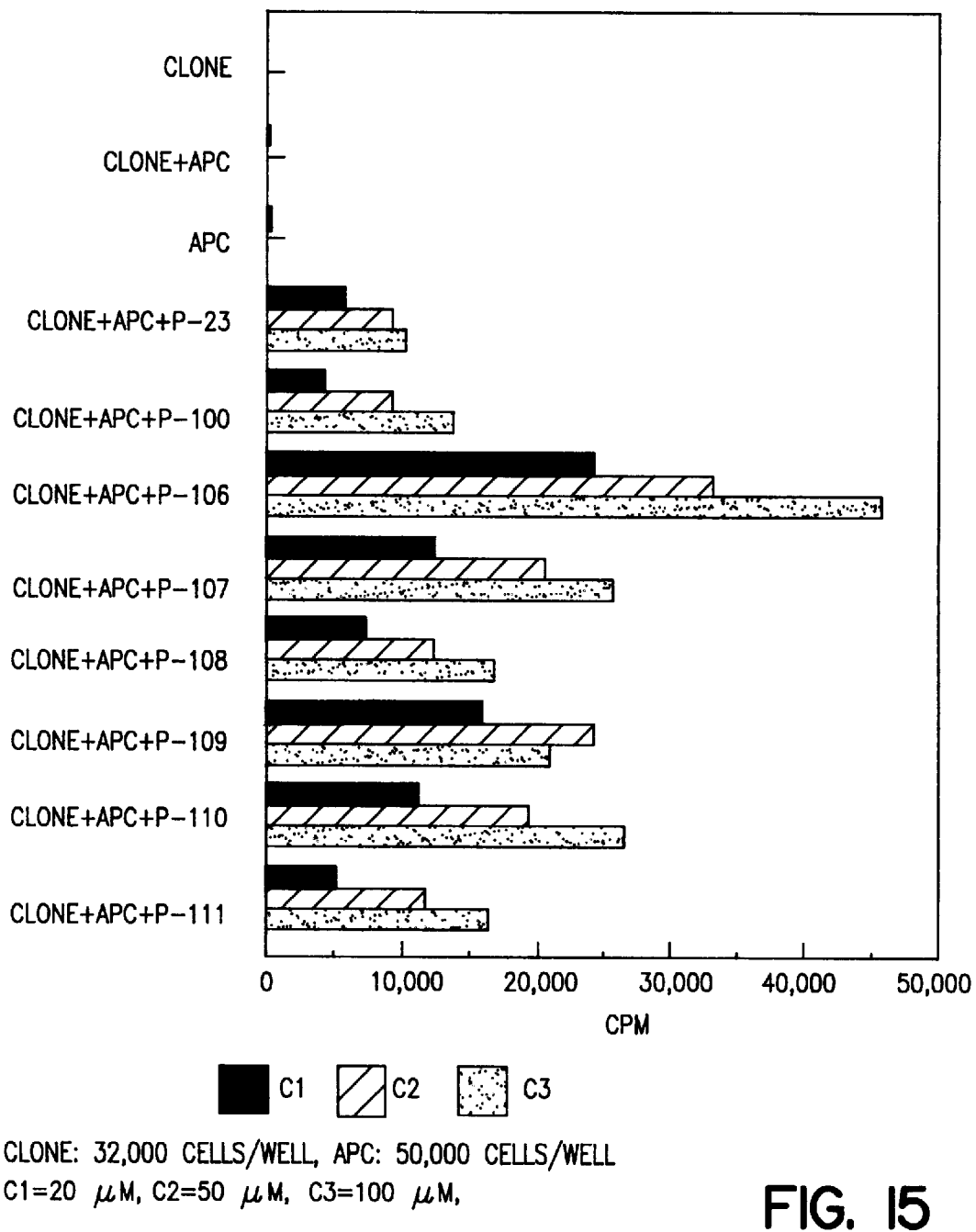

FIG. 15 shows the response of clone 14 to a new set of synthetic peptides carrying the same mutation in position 61 as found in peptide 23. These new peptides encompass the sequences 51–67, 52–67, 53–67, 51–65, 52–65 and 53–65 of the ras sequence, see Table 6. The sequences of these peptides are given in Table 7. Conditions were as described in FIG. 14.

Figure 16:
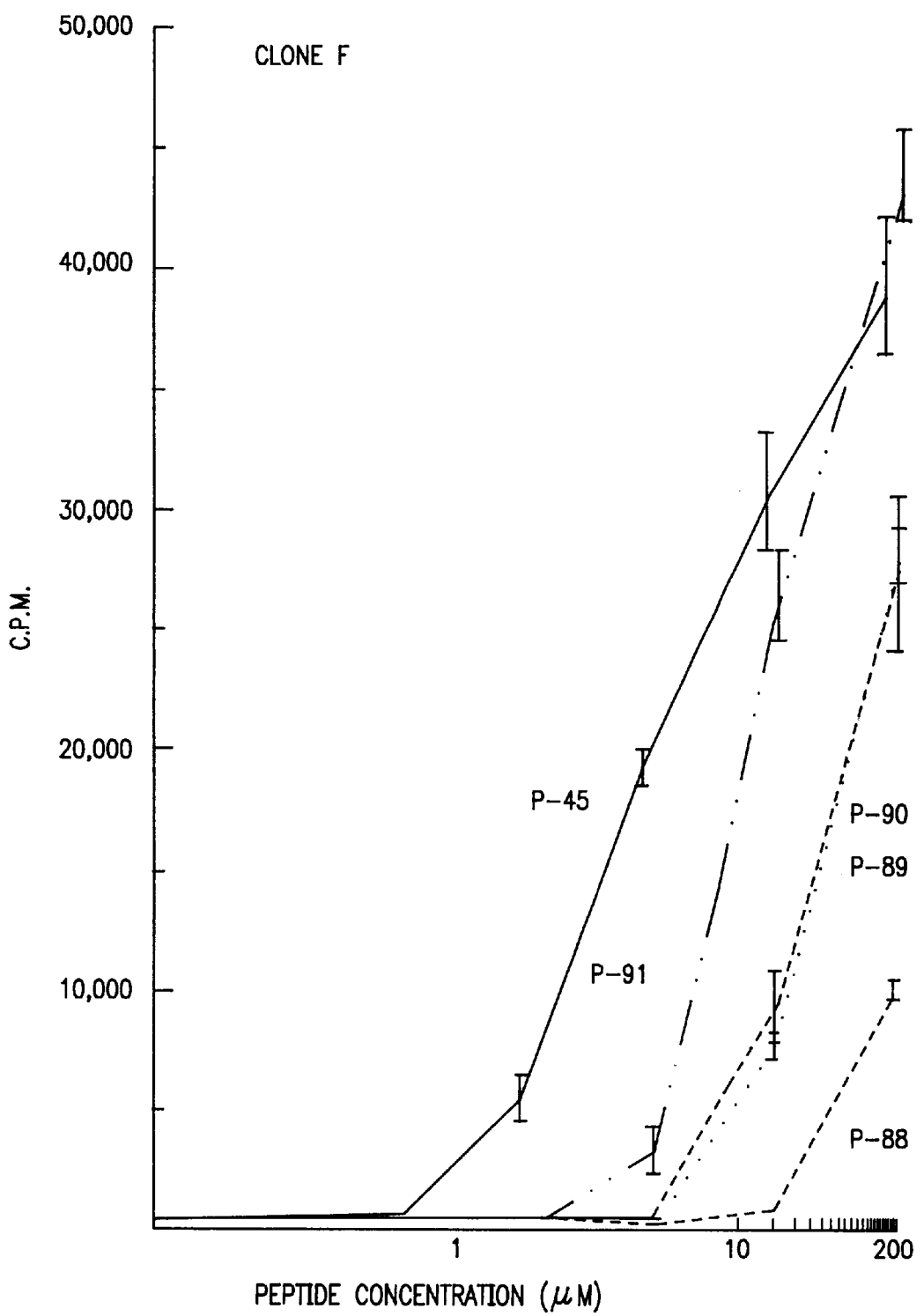

FIG. 16 shows dose-response curves for clone F to peptide 45, and peptides 88–91. The structures of the peptides are given in Table 2. The peptide concentration was as given in the Figure, and the conditions of the assay were otherwise as described for FIG. 6.

Figure 17A:
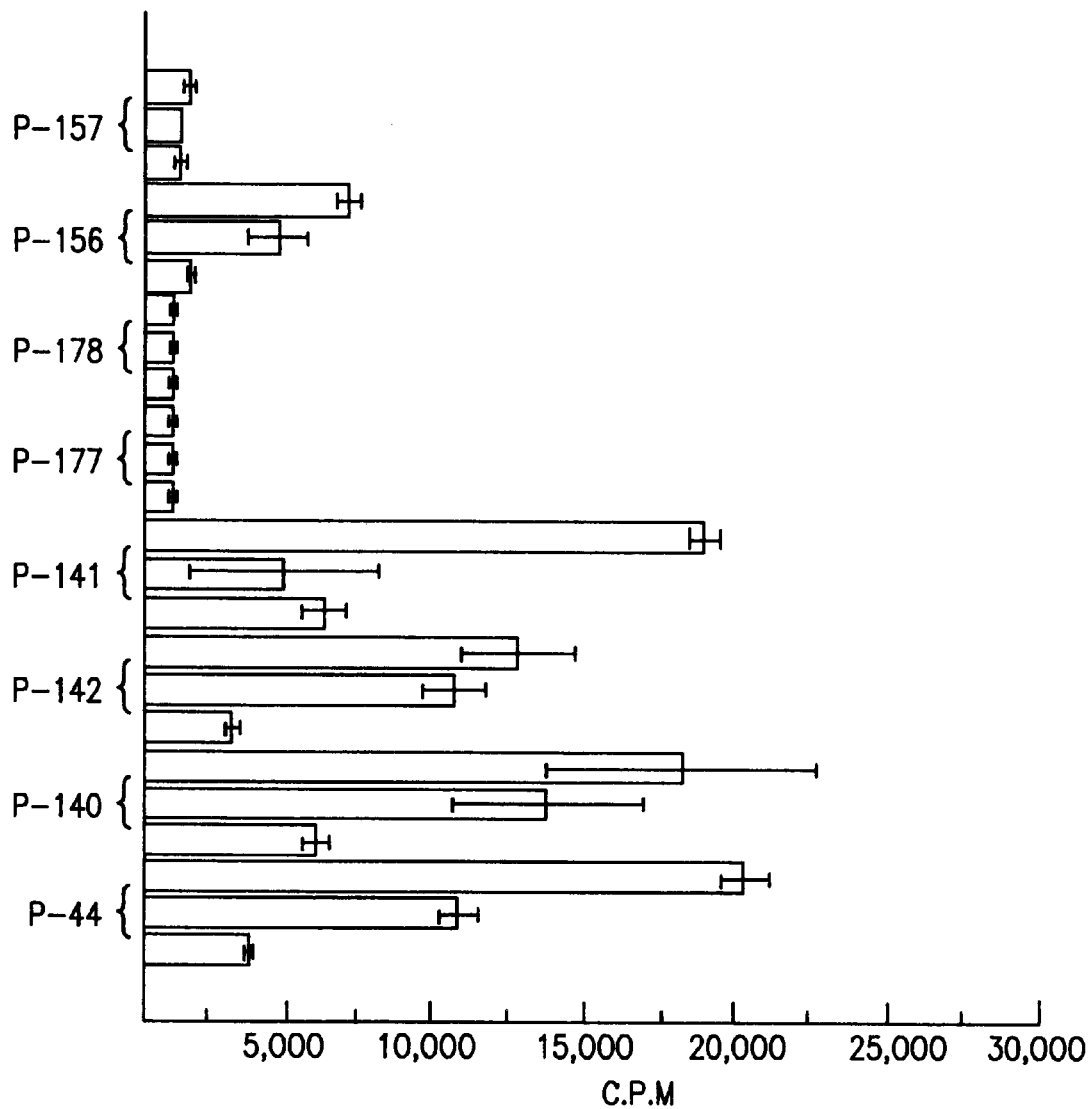
Figure 17B:
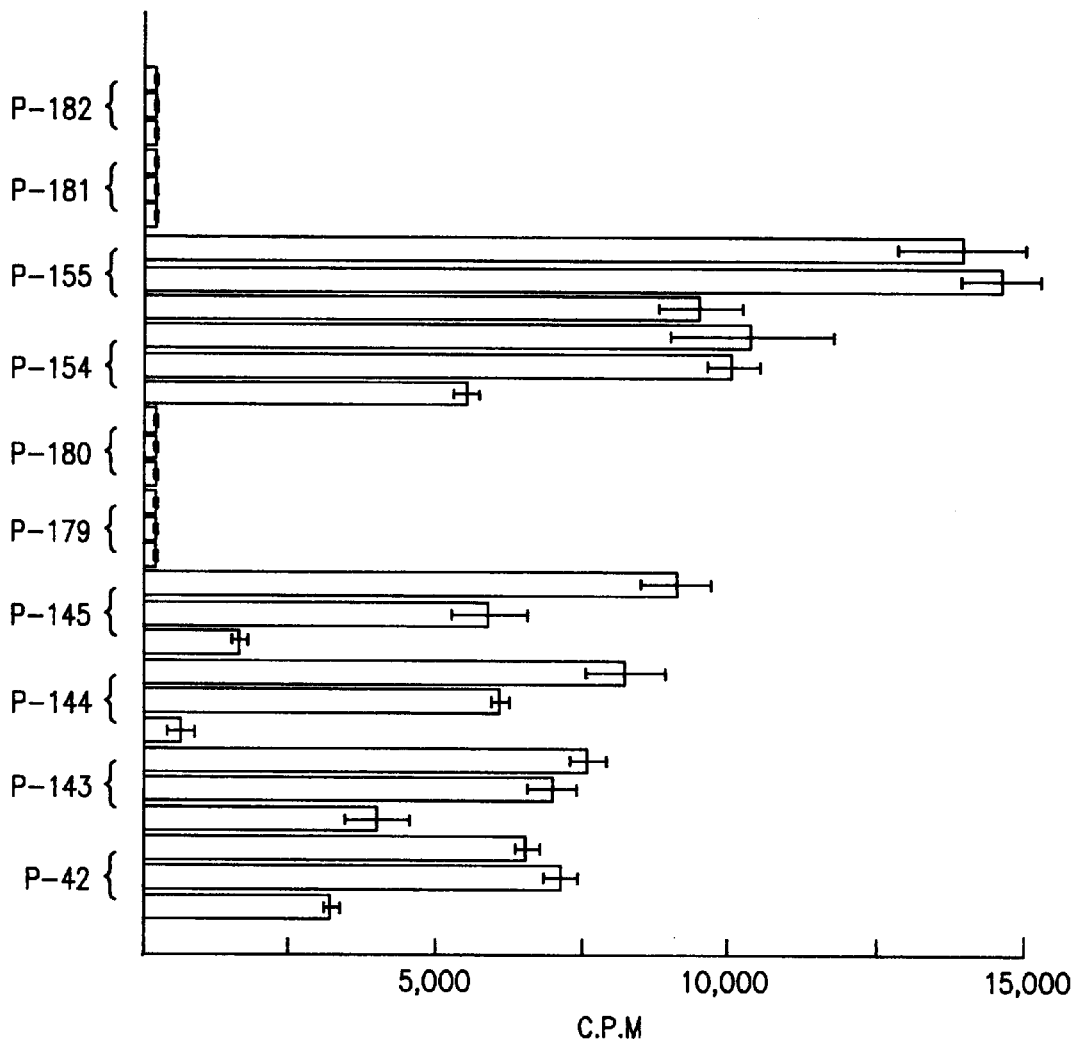

FIGS. 17a–17b show the response of clone B to truncated forms of peptide 43 and of clone I to truncated forms of peptide 42. The peptides were truncated from the N-terminal and C-terminal end as seen in Table 2. For each peptide tree different doses were used, the final concentrations being 20, 50 and 100 µmolar. The number of responder cells and APC was 50 000. The conditions of the assay were as described in FIG. 2.

Figure 18A:
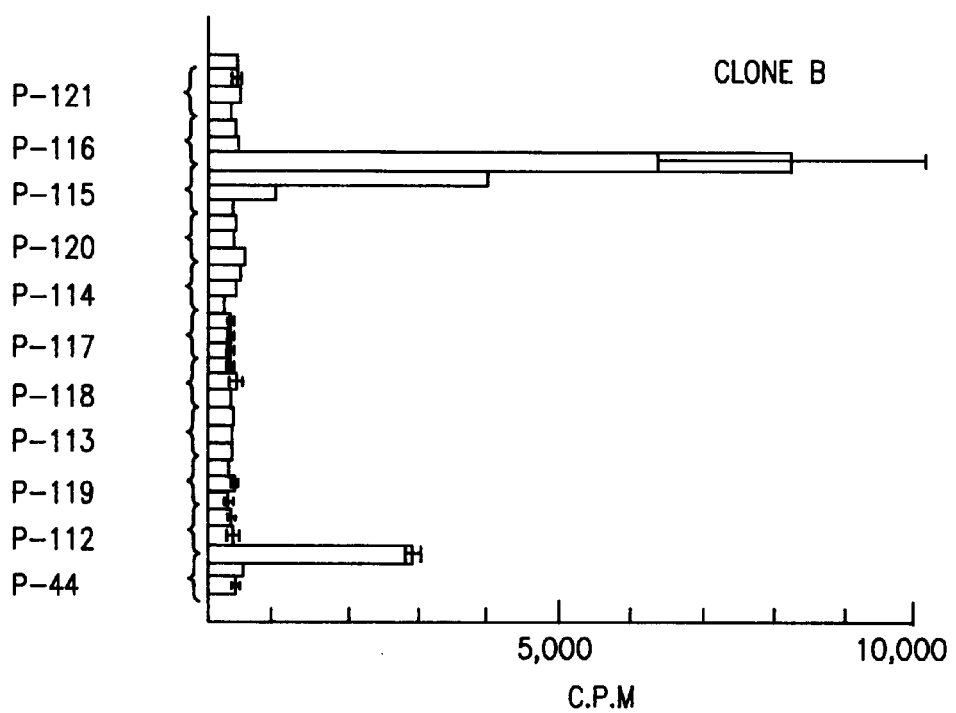
Figure 18B:
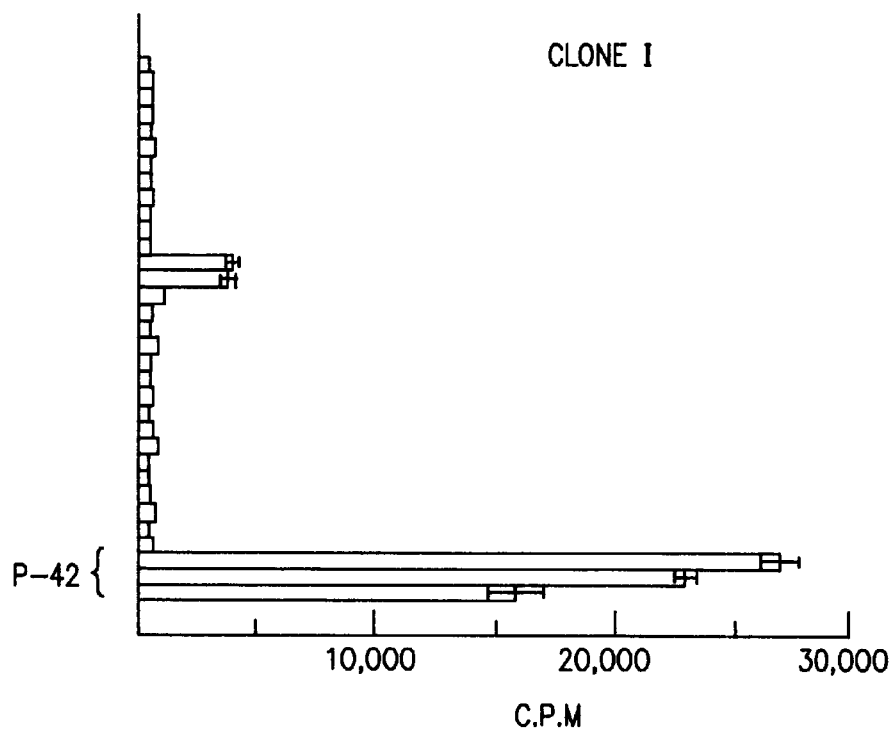
Figure 18C:
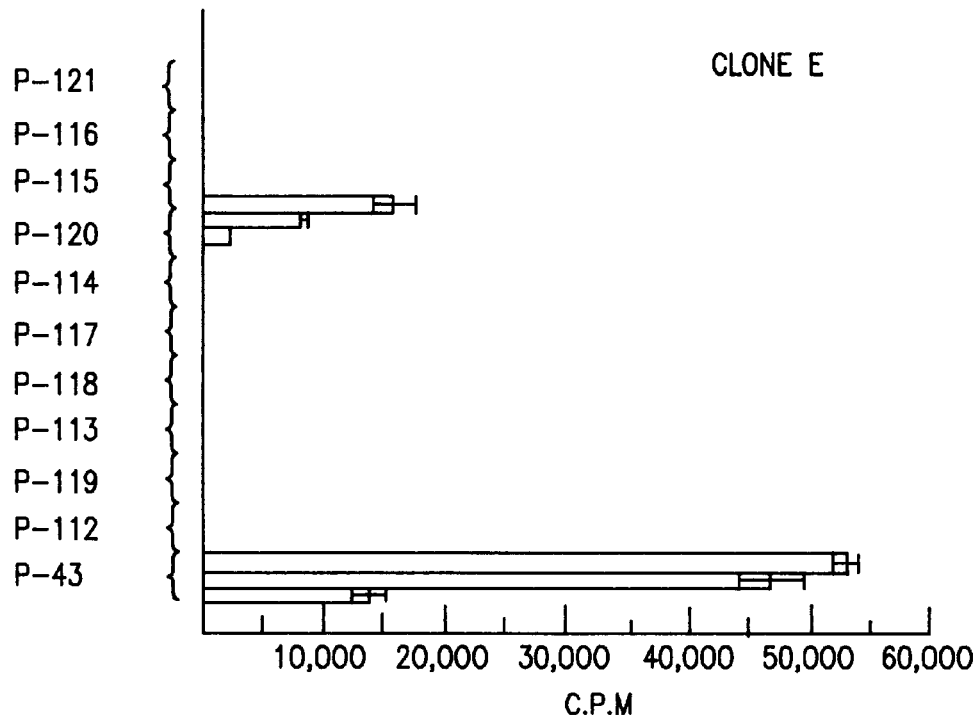
Figure 18D:
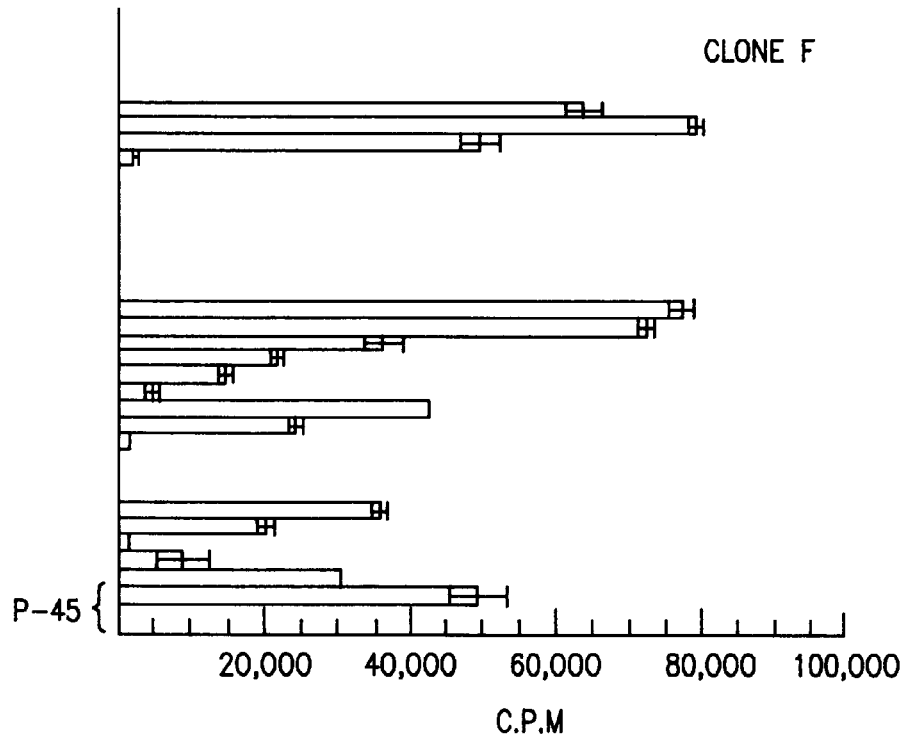

FIGS. 18a–18b show the result of experiments where clones B, I, E and F were stimulated with a panel of long peptides. For each peptide three different doses were used, the final concentrations being 20, 50 and 100 µmolar. For comparison the clones were stimulated with peptides 42, 43, 44 and 45 used for eliciting the clones. The number of responding cells and APC were 50 000. Conditions were otherwise as described for FIG. 2.

Figure 19A:
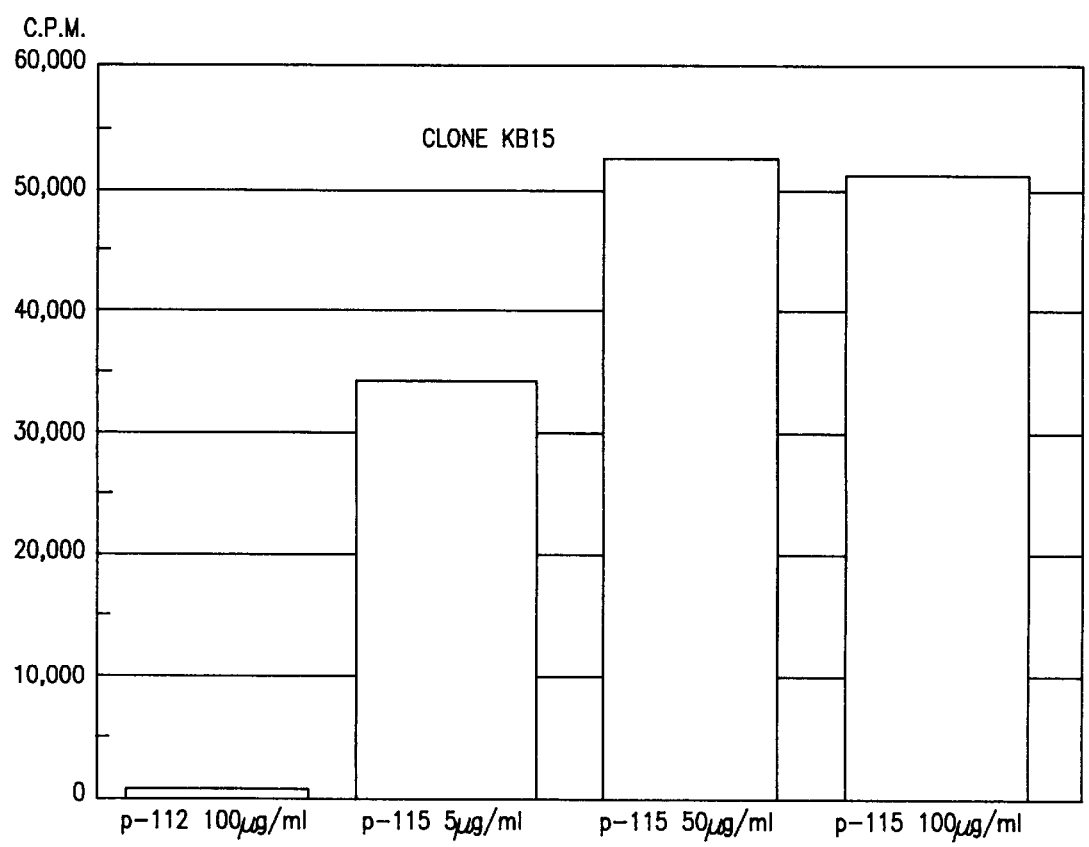
Figure 19B:
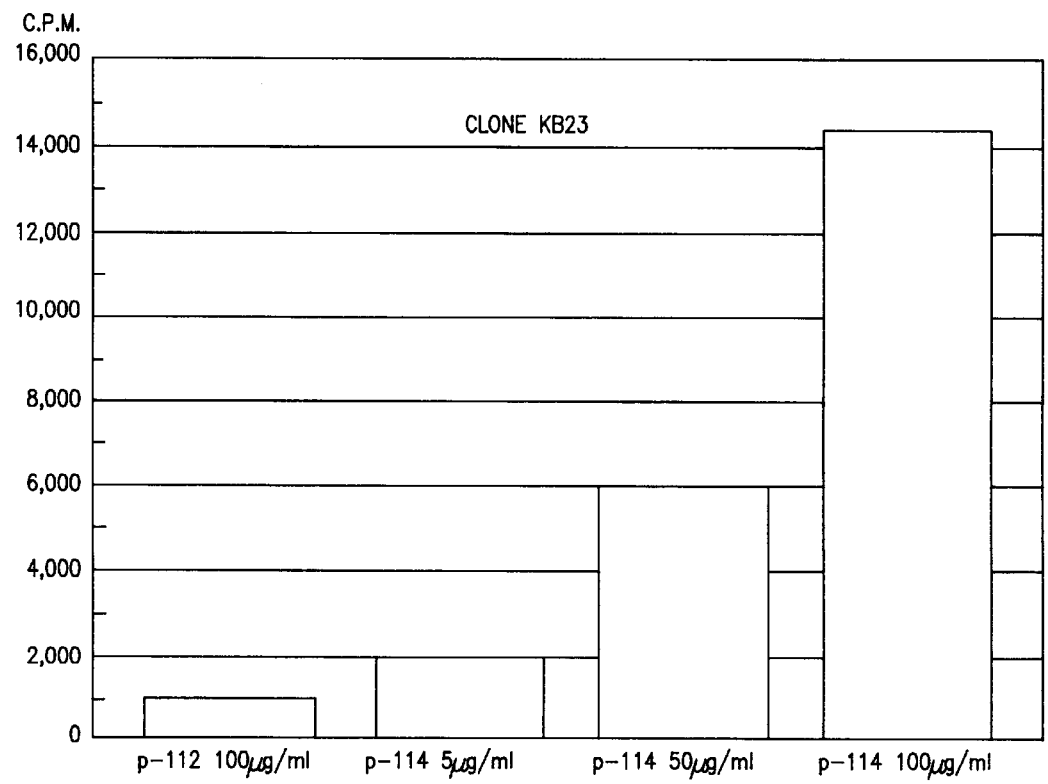

FIGS. 19a–19b show the response of two T cell clones KB 15 and KB 23 derived from a healthy donor after repeated stimulation with a mixture of long peptides, (p-112, p-113, p-114, p-115 and p-116) ) Culture conditions were essentially as described in FIG. 1.

Figure 20:
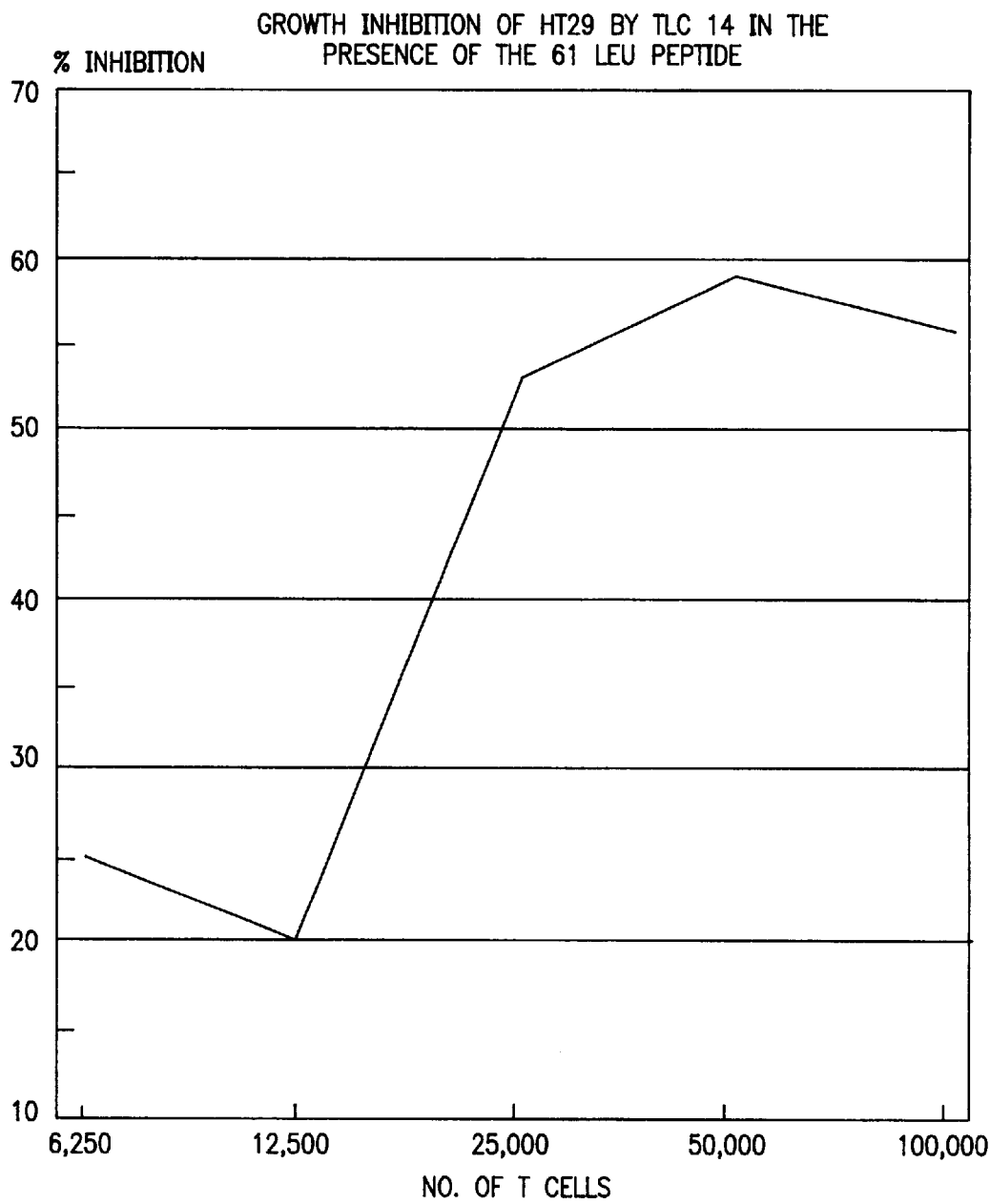

FIG. 20 shows the results of growth inhibition studies of IFN-γ treated HT29 colon carcinoma cells (ATCC, Rockville Md.) using clone 14 as effector cells. The number of target cells seeded per microwell was 20 000, and the cells were treated with recombinant human IFN (Amersham, UK), 500 U/ml for 3 days before the addition of irradiated (2000 rad) effector cells as indicated in the Figure. Peptide treated cells were cultured for the last 24 hours with peptide 106 at the final concentration of 10 µg/ml. After addition of effector cells, cultures were pulsed overnight with 1 µCi of $^3$H-Thymidine per well before harvesting as described in FIG. 2. Specific growth inhibition was calculated from incorporation data of control cultures without peptide added.

INDUCTION OF RAS SPECIFIC T CELLS BY PRIMARY IMMUNIZATION IN VITRO

We first investigated if the T cell repertoire of normal healthy persons contained T cells capable of recognizing and responding to a panel of peptides carrying amino acid sequences derived from mutated p21 ras.

Peripheral blood mononuclear cells from healthy donors were stimulated in vitro with mixtures of synthetic p21 ras peptides according to the present invention as described in FIG. 1.

The results of some of these experiments are shown in Table 3. No primary response against the peptide mixtures could be observed. Similar experiments with a panel of 15 healthy donors stimulated with individual peptides also demonstrated a complete lack of primary responses against these peptides (data not shown). Together these results indicate that the frequency of responsive cells in a normal population is very low. However, when in vitro cultures were repeatedly stimulated with peptides and fresh irradiated antigen presenting cells, strong response against the corresponding peptides could be observed (Table 3).

These data clearly demonstrate that after appropriate in vitro immunization with peptides carrying amino acid sequences derived from mutated oncogenes, specific T cell responses can be obtained. Thus we also have shown that T cells with specificity for p21 ras derived peptides are present in a normal T cell repertoire, and this donor has HLA molecules that are capable of binding such peptides.

We next wanted to investigate the fine specificity of the T cells capable of recognizing p21 ras peptides and to define the HLA molecules that are responsible for binding of these peptides and presenting them to the responding T cells. To this end we cloned the activated T cells present in the culture which was responding to a mixture containing the peptides P-42 to P-46. The cloning procedure is described in FIG. 1. Data from the cloning experiments are summarized in Table 4. Of the clones showing specificity for single peptide, four were selected for further studies.

Figure 2A:
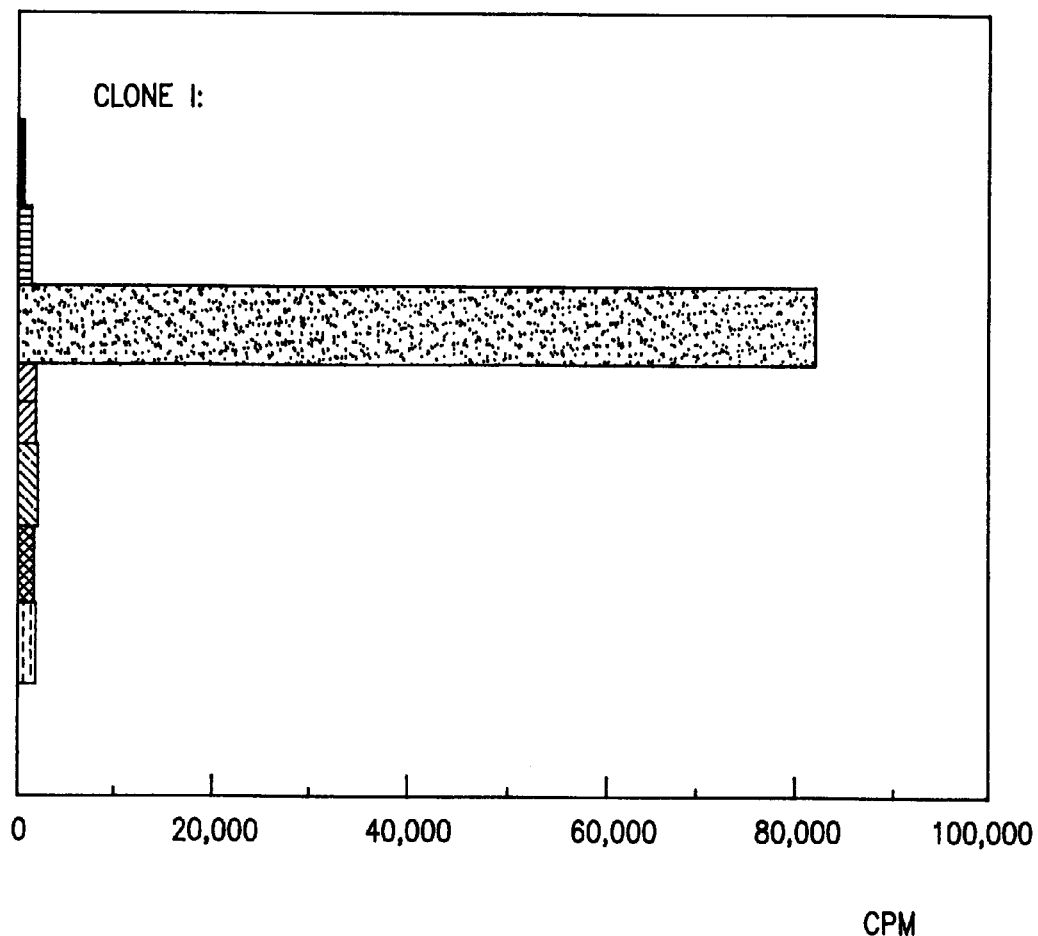
Figure 2A:
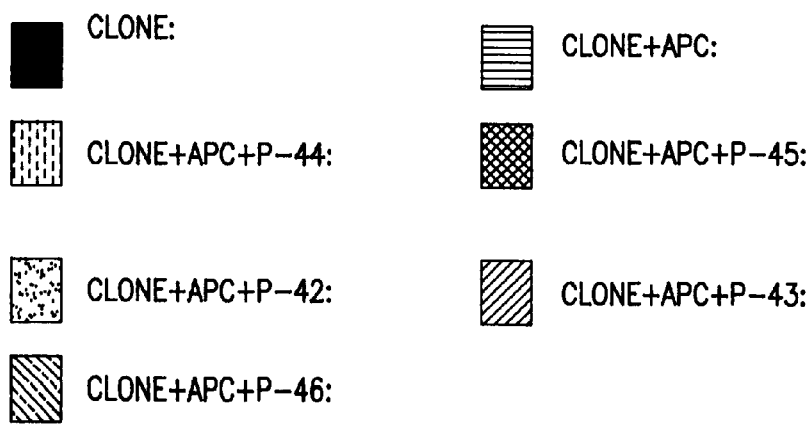

Clone I showed exclusive specificity for peptide 42 which contains the amino acid lysine in position 12. Substituting lysine with several other amino acids totally abrogated the response (FIG. 2a).

Figure 3A:
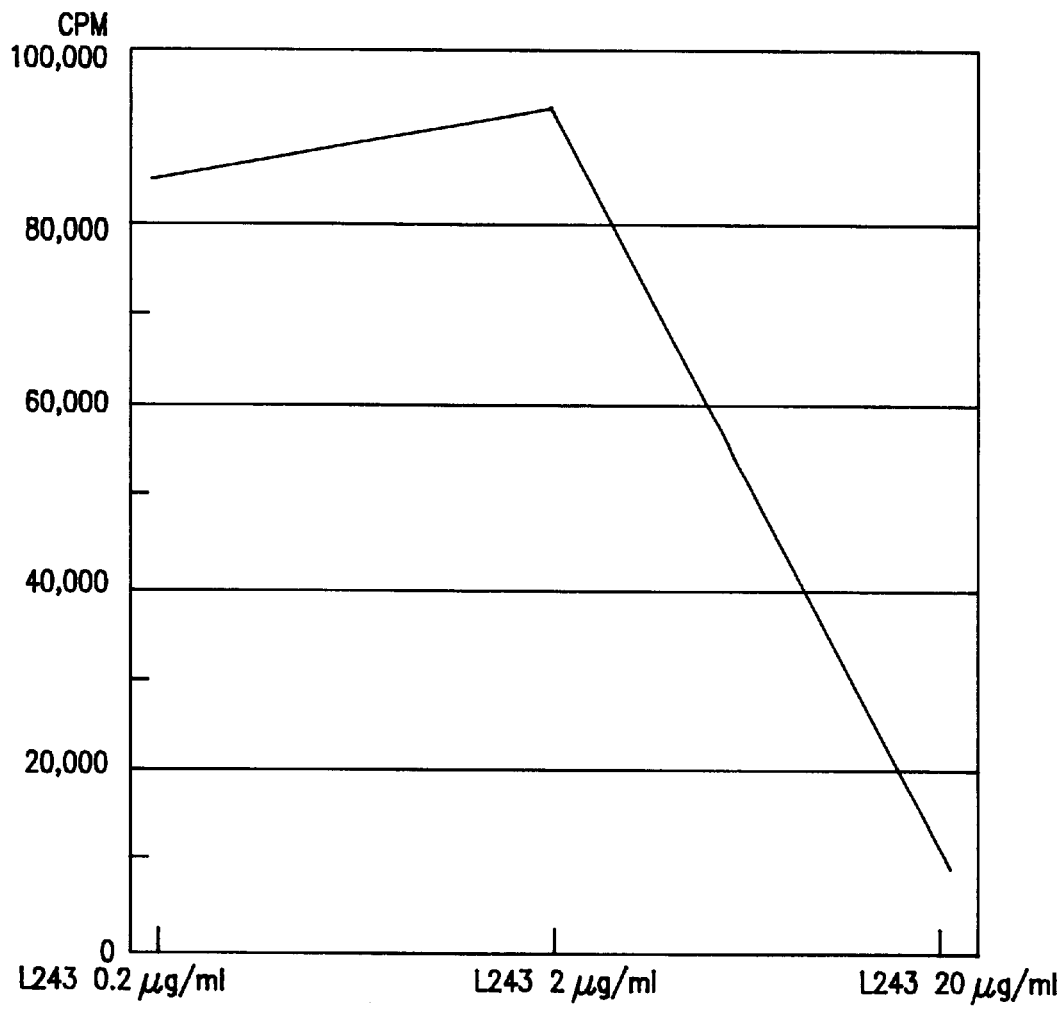

The response against peptide 42 could be completely blocked with the reference monoclonal antibody against HLA-DR, L243, but not with monoclonal antibodies against HLA-DQ and -DP, demonstrating that peptide 42 is bound to HLA-DR in this particular donor (FIG. 3a).

Figure 2B:
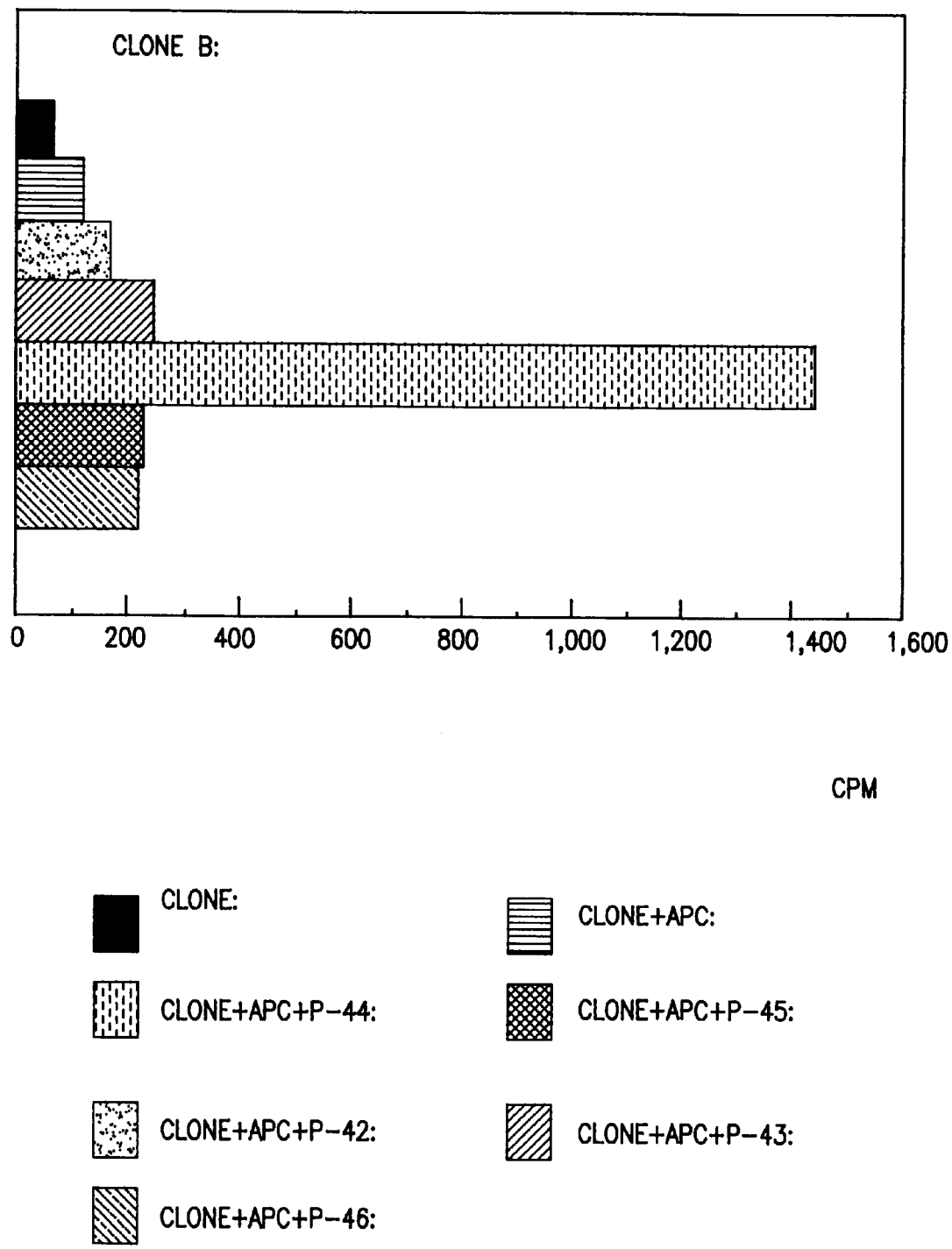

Clone B showed exclusive specificity for peptide 44 which contains the amino acid arginine in position 12. None of the other peptides were recognized (FIG. 2b).

Figure 3B:
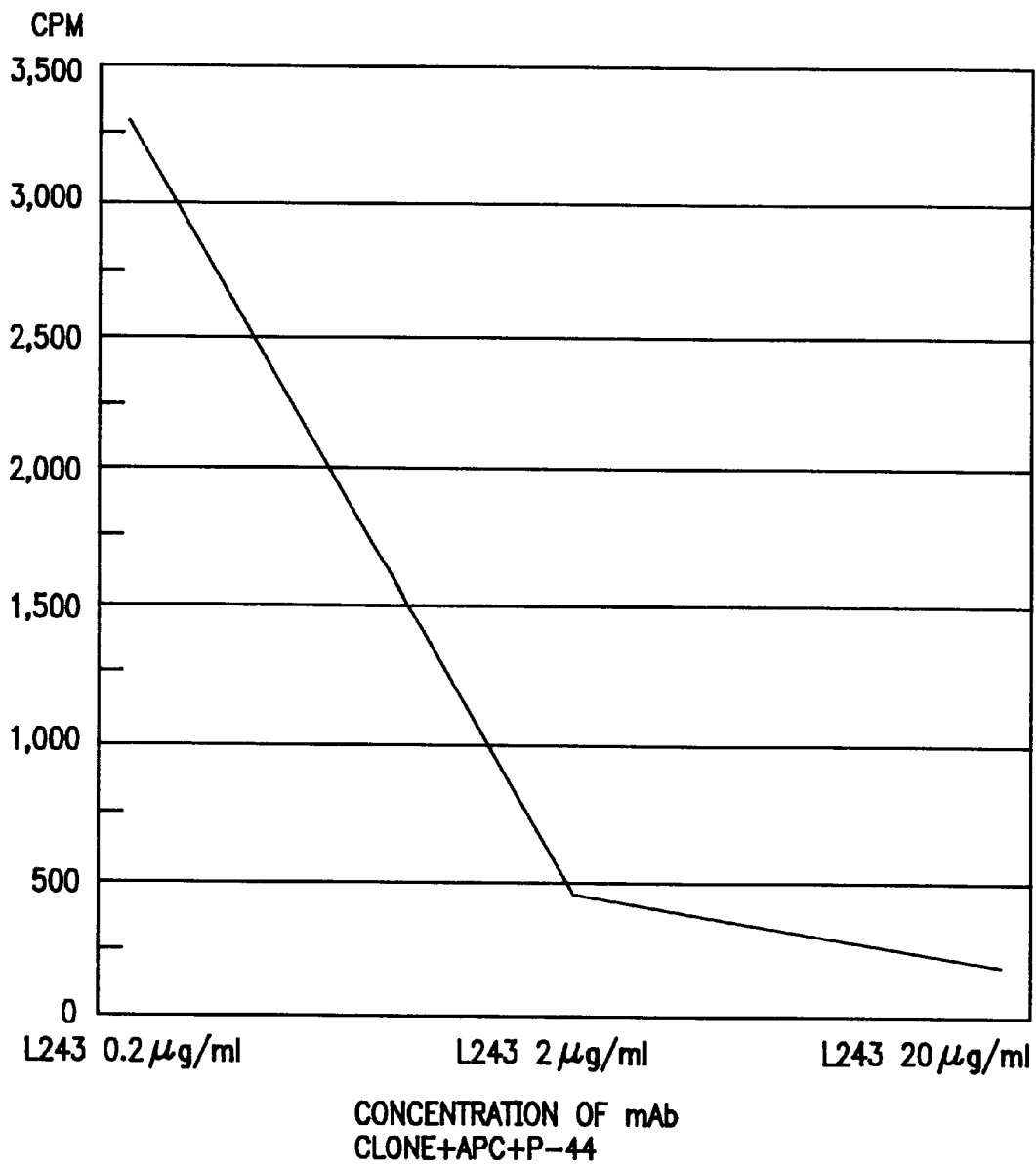

As with clone I, clone B was also HLA-DR restricted as evidenced by blocking studies with monoclonal antibodies (FIG. 3b).

Figure 2C:
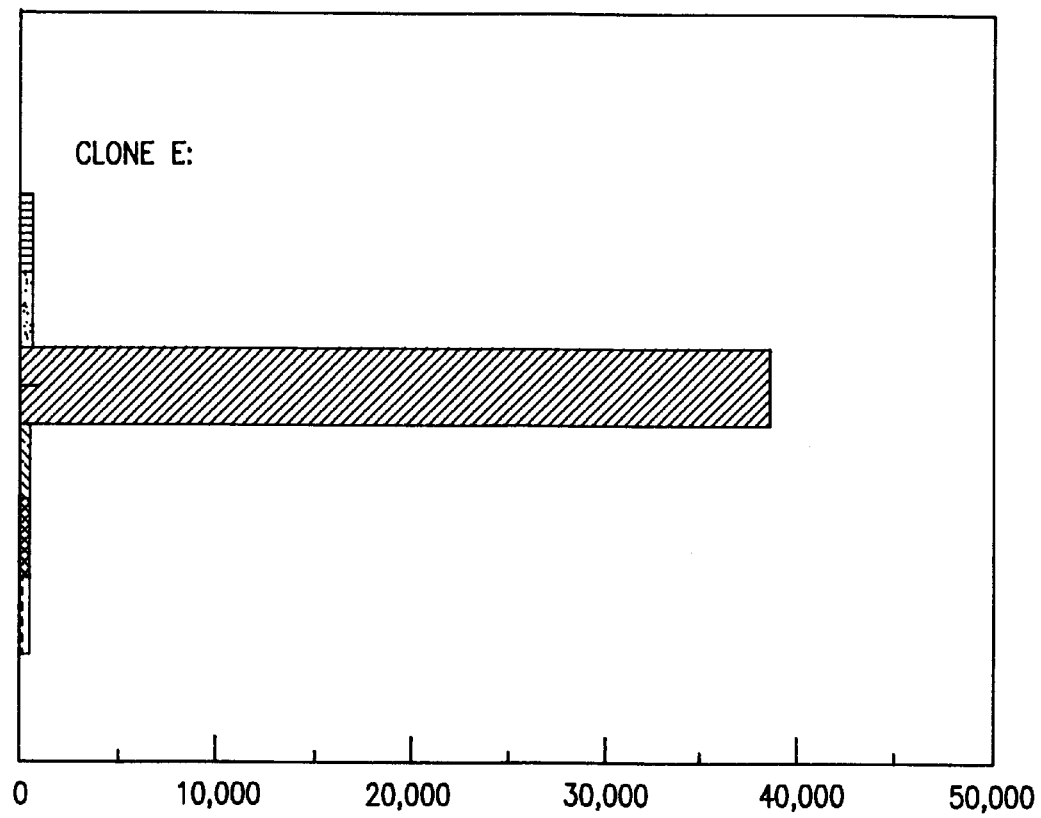
Figure 2C:
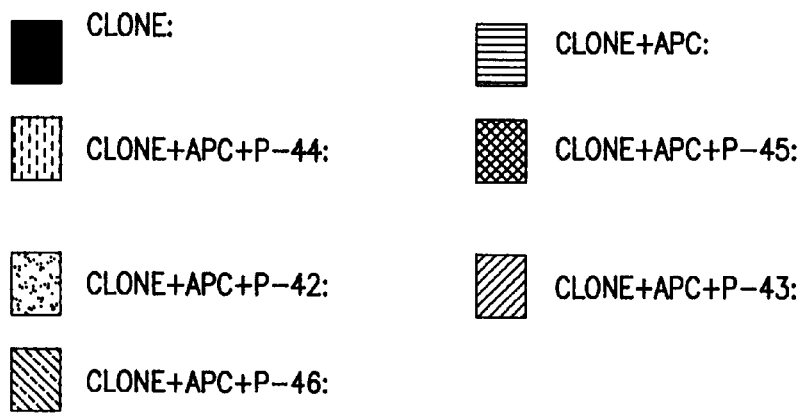
Figure 2D:
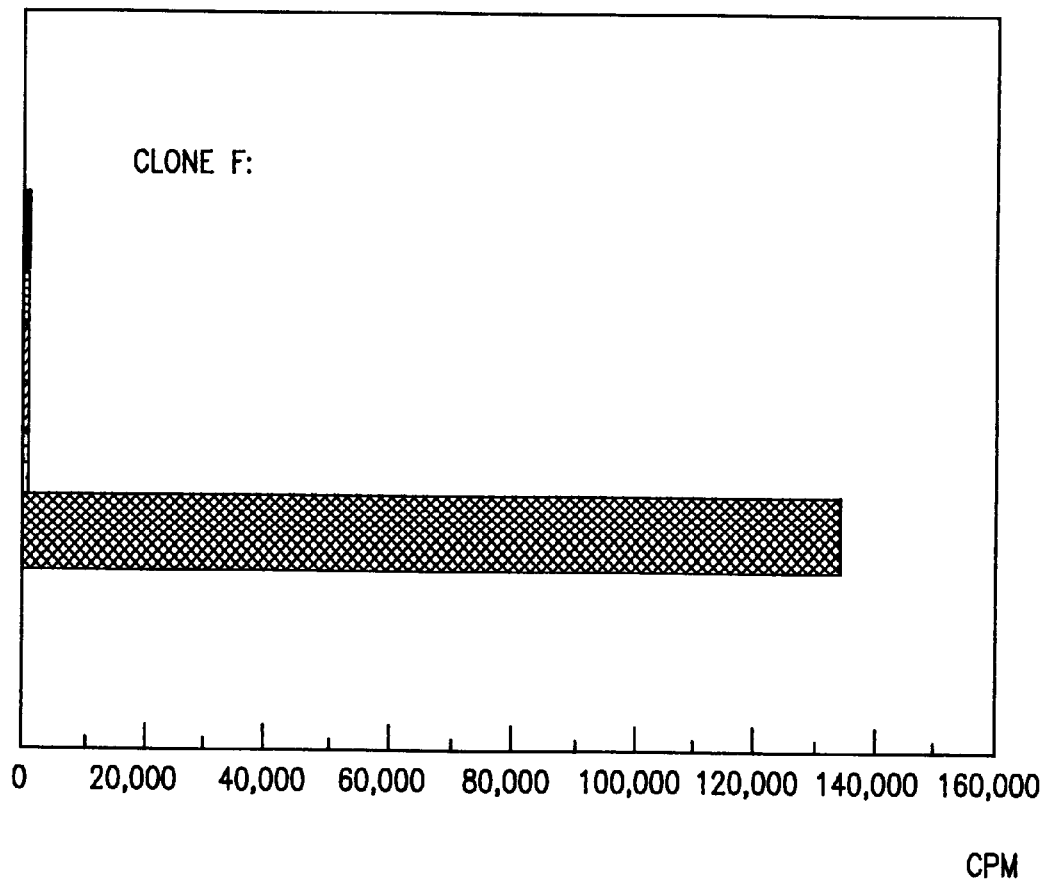
Figure 2D:
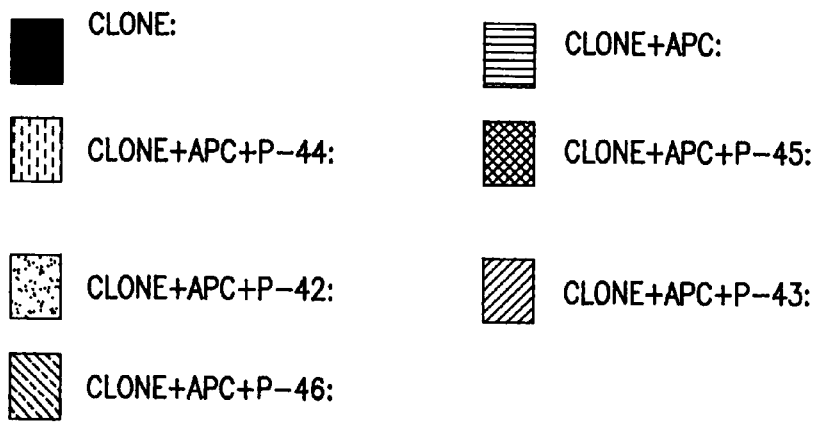

Clone E showed exclusive specificity for peptide 43 which contains the amino acid valine in position 13. None of the other peptides were recognized (FIG. 2c).

Figure 3C:
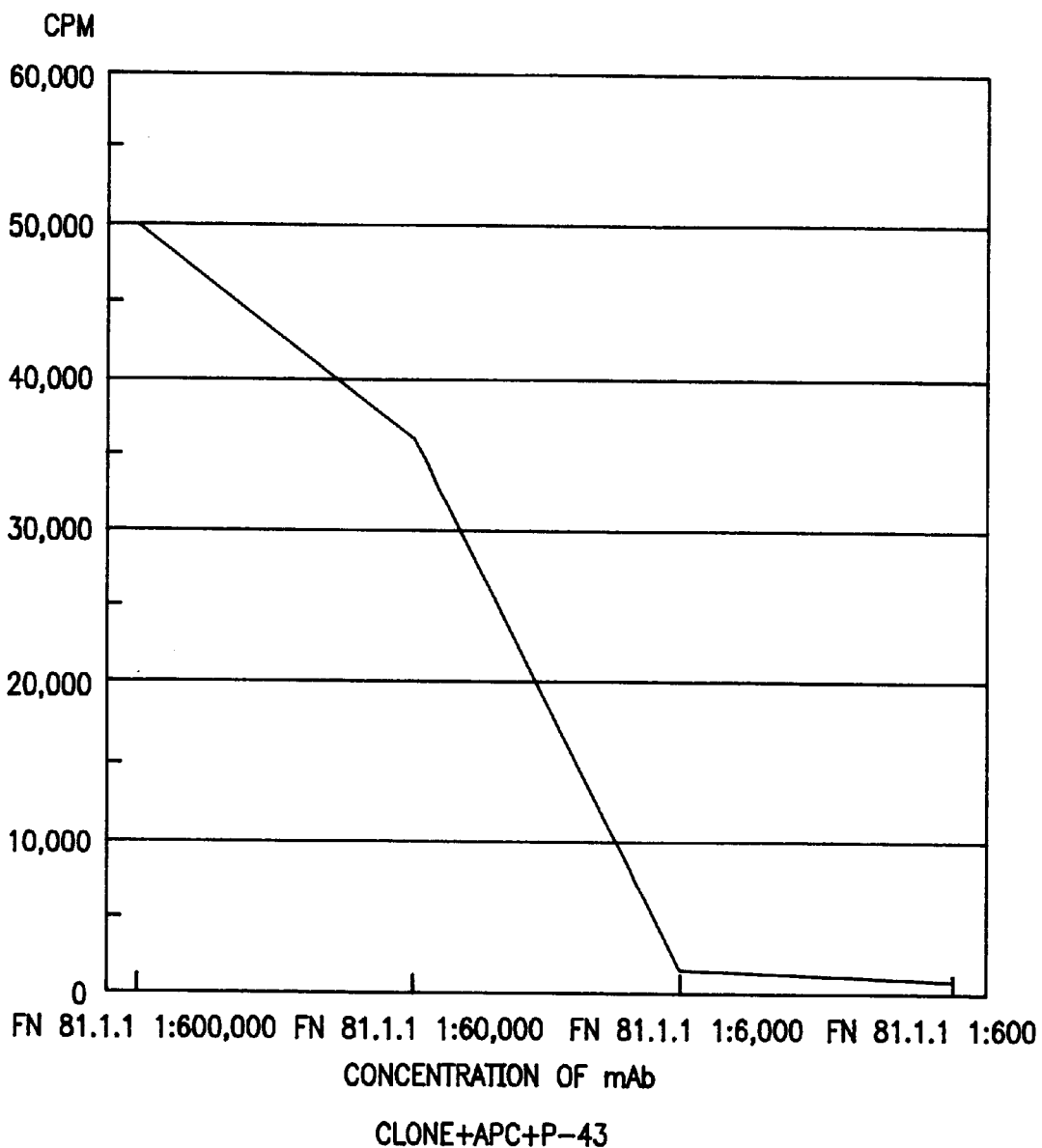

Contrary to the clones recognizing peptide 42 and peptide 44 this clone was not blocked by anti HLA-DR monoclonal antibodies, but instead was blocked by a monoclonal antibody recognizing HLA-DQ (FIG. 3c). Anti HLA-DP had no effect. These data show that peptide 43 is bound to HLA-DQ in this particular donor.

Figure 2E:
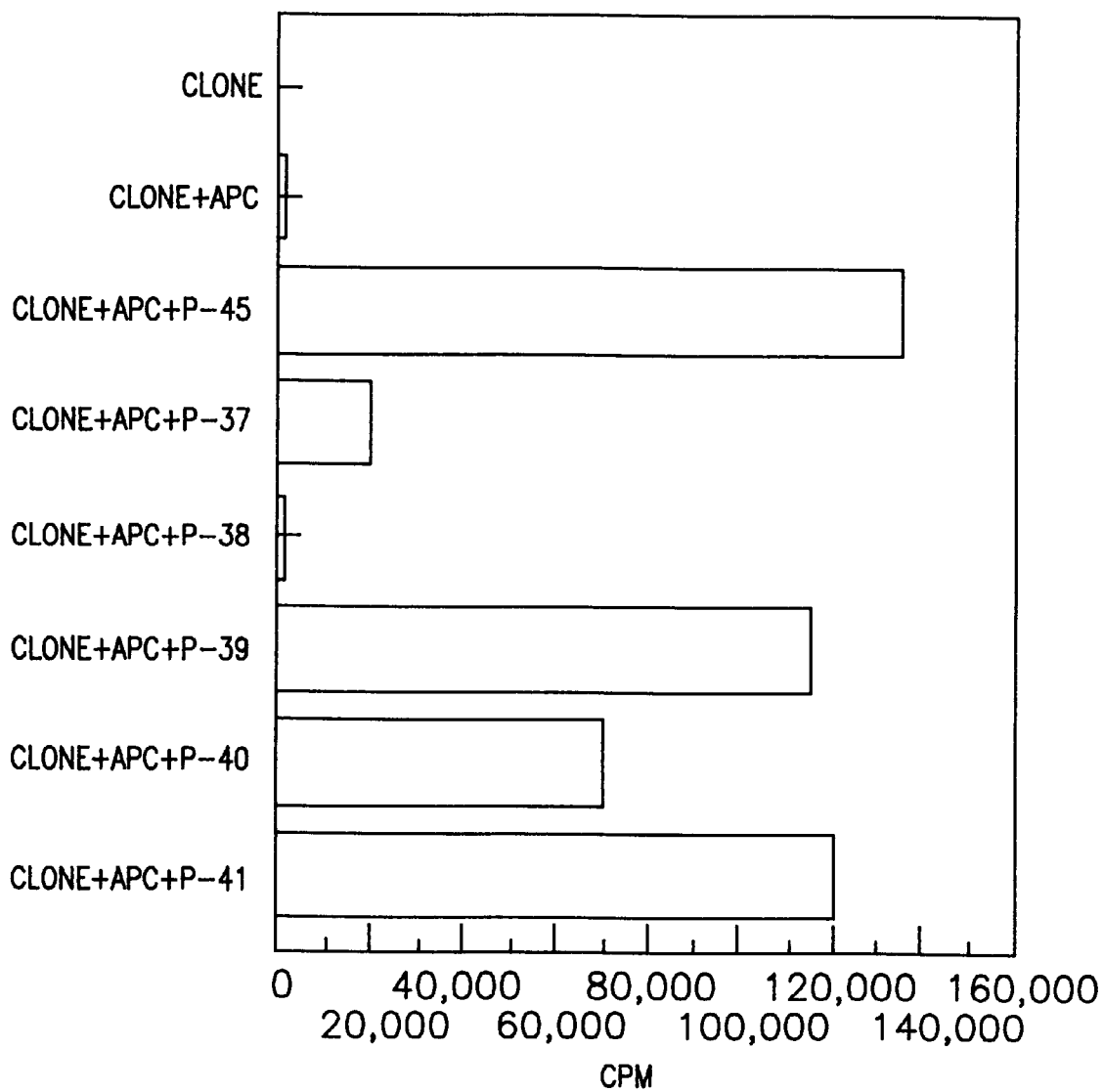
Figure 3D:
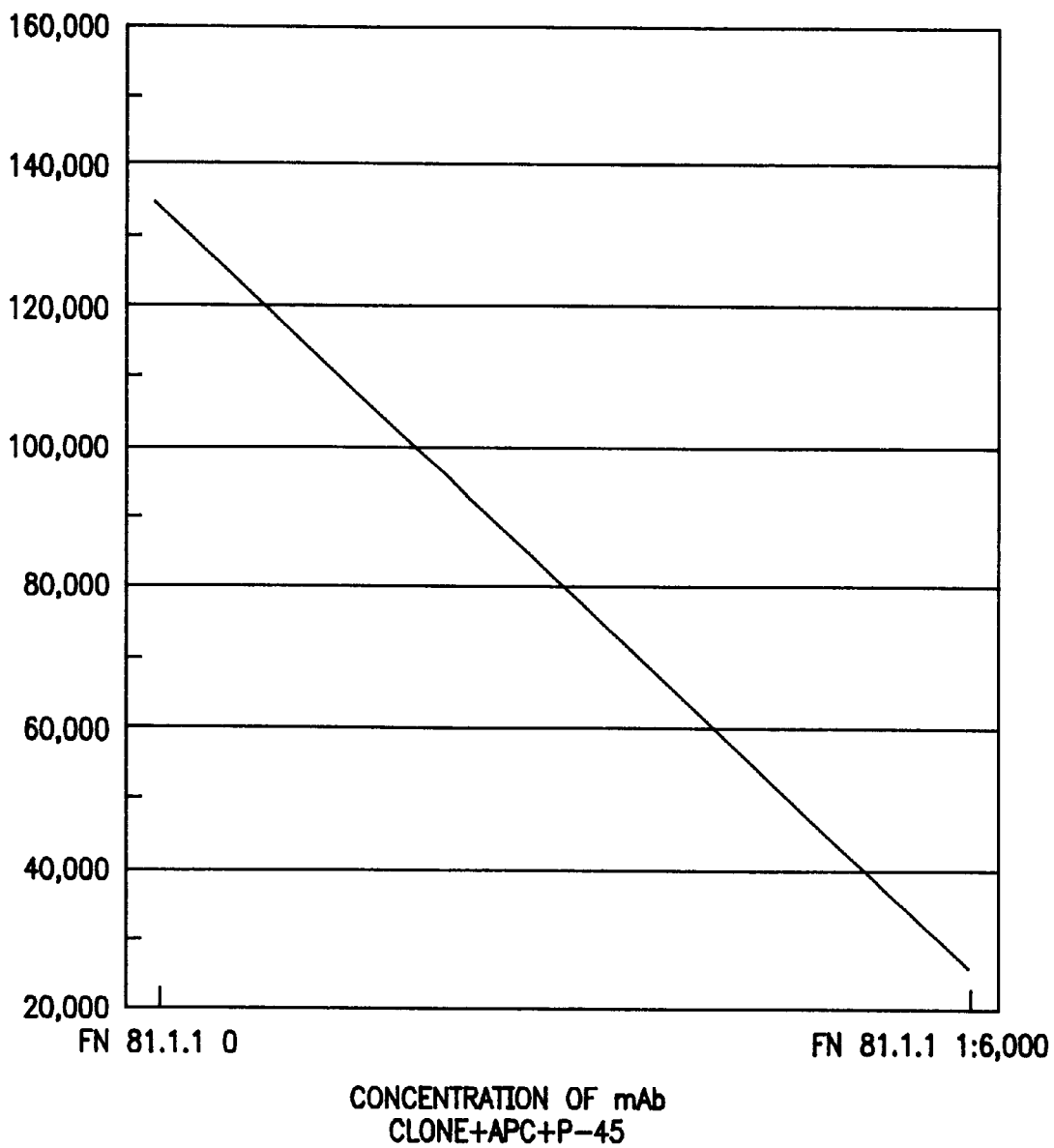

Clone F showed a different pattern of reactivity. Clone F gave very strong responses against peptide 45 containing alanine in position 12, which was present in the original peptide mixture. It was unreactive to the other peptides in the mixture (FIG. 2d), but reacted to a variable degree towards the other peptides (FIG. 2e). The reactivity of this clone seemed to be critically dependent on having amino acid glycine in position 13 since substitution of this glycine with aspartic acid or valine totally abrogated the response. Substitution of glycine in position 12 with the basic amino acid lysine or arginine resulted in low or no responses indicating that such substitutions interfere with the T cell receptor binding site. As with clone E, this clone was also HLA-DQ restricted as demonstrated by blocking by monoclonal antibodies (FIG. 3d). One interesting observation is that the two peptides carrying basic amino acids in position 12, and which fail to stimulate the HLA-DQ restricted clone F, both are capable of binding to HLA-DR and are reciprocally recognized by the two clones I and B.

In order to map peptide binding to HLA-DR and HLA-DQ, we tested the non-stimulatory p21 ras peptides for capacity to inhibit the binding of peptide 42 to HLA-DR, using stimulation of clone I as indicator system, and inhibition of peptide 43 binding to HLA-DQ using stimulation of clone E as an indicator system.

Binding of peptide 42 to HLA-DR was strongly inhibited by a 25 fold excess of peptides 39, 40, 41, 43, 44 and 45 (FIG. 4). The other peptides only marginally inhibited the binding. Notably, none of the peptides carrying amino acid 61 were able to significantly inhibit binding to HLA-DR and subsequent activation of clone I. Conversely, all of the peptides inhibited binding of peptide 45 to HLA-DQ, and subsequent activation of clone E (FIG. 5). Thus, all the peptides carrying amino acid sequences derived from p21 ras, were capable of binding HLA-DQ, including the peptides carrying the unmutated 6–19 sequence (gly in position 12 and 13) and the unmutated 54 to 69 sequence (gln in position 61). It is thus possible that all of these peptides may be immunogenic in the context of HLA-DQ, and that several of the peptides in addition may be immunogeneic in the context of HLA-DR, as already shown for peptide 42 and 44, and a peptide containing Val in position 12 (Jung & Schluesener, 1991).

In order to investigate which amino acids were essential for peptide recognition by the HLA-DQ restricted T cell clones E and F, we synthesized truncated forms of peptide 43 and 45 as shown in Table 2. The peptides were truncated both from the N-terminal and C-terminal end. The first important question was whether the addition of a duplication of amino acids Ala and Leu in the C-terminal part of the peptides used for in vitro immunization was of importance. Results in FIGS. 6 and 8 demonstrate that the two additional amino acids contributed marginally to the site recognized by clone E, and were of no importance for the recognition of peptide by clone F. Since peptide 79 lacking the duplicated amino acids was equally efficient in stimulating clone F. Peptides 64, 79 and 80 stimulate clone E in a concentration of 10 µl. Peptides 65 and 81 become stimulatory in a concentration of 250 µl. Peptides 66, 67, 68, 82 and 83 inhibit at this concentration (FIG. 7), and are thus capable of binding to HLA-DQ. Peptides 69, 70, 74, 75 and 76 stimulate clone F at 10 µl concentrations.

The combined data in FIGS. 6–8 show that several peptides carrying Ala in position 12 or Val in position 13 and varying in length, can be recognized by clones E and F. The striking symmetry in the results with clone E and F demonstrate that the amino acids Val in position 8 and Ser in position 17 are absolutely essential for stimulation of these T cell clones. A predicted minimum peptide for stimulation of clone E will therefore have the sequence Val-Val-Gly-Ala-Gly-Val-Val-Gly-Lys-Ser (SEQ ID NO: 103) and for Clone F the sequence Val-Val-Gly-Ala-Ala-Gly-Val-Gly-Lys-Ser (SEQ ID NO: 27). The predicted minimum peptide 8–17, 12-Ala, (peptide 88) was synthesized and its capacity to stimulate clone F was compared to peptide 45 and several other peptides as depicted in FIG. 16. The dose-response curve for peptide 88 confirms its stimulatory capacity, but shows that it is far less potent than the peptide used for eliciting this clone. Shorter peptides still bind HLA-DQ, but have lost amino acids critical for recognition by these T cell clones. We anticipate that also these peptides, when used to stimulate T cells in vitro, may give rise to a new set of T cell clones with slightly different specificities.

In order to investigate if the same amino acids that were identified as being important for peptide recognition by the HLA-DQ restricted T cell clones were also essential for the recognition by the DR restricted clones B and I, we synthesized truncated forms of the peptides 42 and 44 as shown in Table 2. The peptides were truncated both from the C- and N-terminal ends. Results in FIGS. 17a–17b confirm that the duplicated amino acids Ala and Leu were of no importance for recognition by these T cell clones. For both clones, Lys in position 16 is absolutely essential as removal of this amino acid abrogates the peptide response. The two clones differ in their requirement for the presence of Val in position 7, as this amino acid is essential for stimulation of clone B, while its presence seems to negatively influence the response to clone I. From the results in FIGS. 17a–17b the minimum peptides for stimulation of clone B and I are Val-Val-Val-Gly-Ala-Arg-Gly-Val-Gly-Lys (SEQ ID NO: 101) and Val-Val-Gly-Ala-Lys-Gly-Val-Gly-Lys (SEQ ID NO: 102).

To address the question of peptide processing, we synthesized p21 ras peptides encompassing the residues 1–25. Presumably these peptides would allow the generation of naturally processed peptides when fed to the APC. The results of this series of experiments are given in FIG. 18. All the clones were able to respond to the 1–25 peptides provided the correct amino acid substitution in positions 12 and 13 were present. When compared to the response against the peptides used in primary stimulation, long peptides were more efficient in stimulating clones B and F. Clones E and I showed the opposite reactivity pattern. These results may indicate that processing of the long peptides may give rise to peptides which differ from the peptides used for generation of the clones.

To summarize the results obtained with only four of our T cell clones:

1. Peptides 45, 41, 40, 39, (and 37) and peptide 43 can be recognized by T cell clones F and E respectively. Peptides 42 and 44 are recognized by clones I and B respectively, thus all but two of the most common p21 Gly-12 and Gly-13 ras mutations can be recognized by a limited set of T cell clones derived from precursor T cells present in the normal repertoire of a single donor.
2. Peptides can bind to both HLA-DR and DQ molecules, since peptides are recognized in a HLA-DR restricted manner (Clone I and B) and in a HLA-DQ restricted manner (clone E and F).
3. By using truncated peptides we have defined putative minimum sequences required for stimulation of our DQ and DR restricted T cell clones. All clones require the presence of a core sequence spanning positions 8–16 and differ only slightly in the requirements of amino acids in the positions flanking this sequence.

4. Both the DQ and DR restricted clones can respond to peptides of varying length, from the short core sequence up to sequences of 25 amino acids.

5. Our T cell clones have also provided us with important insight into those peptides where no reactive clones are available. Thus, by blocking experiments using 25–50 fold excess of peptides, and the clones E, F, and I as indicator responder cells, we have demonstrated as shown in FIG. 5 that all the synthetic peptides in this study, including the peptides representing ras mutations in amino acid 61, are capable of binding to HLA-DQ, and that several of the peptides are capable of binding to HLA-DR.

Having achieved responses in healthy donors by primary immunization in vitro with the shorter peptides, (peptides 42, 43, 44, 45), and observed that T cell clones elicited by stimulation with these peptides were capable of responding to the longer peptides, which presumably required processing, we investigated if the long peptides also would elicit T cell responses after primary stimulation. For these experiments we selected normal donors having HLA molecules not previously known to bind ras peptides. The results from these experiments appear in FIGS. 19a–19b. Peptides 114 and 115 were capable of stimulating specific T cell responses, and T cell clones recognizing these peptides could be generated from bulk cultures. Thus peptides spanning the sequence 1–25 and containing amino acid substitutions in position 12 are also immunogenic. Our results also show that ras peptide responsiveness is not confined to a single HLA haplotype.

In order to investigate the general nature of ras peptide binding to HLA molecules, we established a binding assay for measuring peptide binding to purified HLA DR and DQ molecules. To compare the binding of ras peptides with a standard, high affinity binding peptide, we first studied inhibition of a radio labelled influenza matrix peptide to purified HLA DR1 molecules. Results shown in Table 11 demonstrate that all the peptides tested were capable of binding to DR1. The binding strength of the ras peptides, as measured by the capacity to inhibit binding of the indicator peptide, was similar to that of the influenza matrix peptide. These data confirm the binding capacity of the peptides used for T cell stimulation, and also demonstrate that nonstimulatory peptides can bind to HLA DR. Furthermore, these data extend our knowledge of DR molecules capable of binding ras peptides to include also DR1. The observation on peptide binding to purified DQ molecules confirms our cellular studies and provides a first example on direct binding of peptides to purified DQ molecules.

The observation so far indicate that binding of ras derived peptides may be a general phenomenon, perhaps reflecting an important surveillance function of the HLA / T cell system in eliminating cells carrying potentially deleterious ras mutations.

It should be noted that our T cell responses are obtained without the addition of exogenous IL-2 to the cell cultures, and thus depend on the inherent capacity of our synthetic peptides to induce specific proliferative responses in the donor T cells. This offers a great advantage over recent techniques based on massive use of IL-2 to induce in vitro proliferation of cells from cancer patients, either derived from peripheral blood (LAK cells) or from tumour infiltrating lymphocytes (TIL cells). This nonspecific manner of T (and NK) cell activation is responsible for the severe side effects seen in patients given treatment with LAK or TIL cell preparations.

The new finding that the T cell repertoire of a normal individual contains T cells capable of specifically recognizing peptides containing several of the mutations commonly found in ras oncogenes in human cancers, is of importance in cancer therapy and the prevention of cancer by prophylactic vaccination. Furthermore it is also important that all of the synthetic peptides from ras oncogenes are capable of binding to HLA gene products as demonstrated in the peptide blocking experiments.

Of central importance is the finding as shown below, that peripheral blood from a patient with follicular carcinoma of the thyroid gland contain lymphocytes capable of giving a classical memory response against a ras p21 synthetic peptide representing one of the ras mutations commonly found in this cancer form. Such a response is not to be expected unless the patient's T cells have experienced a prior exposure to the same or a very similar peptide fragment in vivo. Such exposure is easily envisaged to occur if the cancer cells of the patient harbour this specific mutation of amino acid 61.

Demonstration of ras Peptide Specific Memory T Cells in Cancer Patients

The synthetic peptides employed for induction of ras peptide specific T cells by primary immunization in vitro, were constructed without precise knowledge of the composition of naturally occurring ras peptides formed by processing of the mutated ras gene product by proteolytic enzymes in vivo.

Although we have demonstrated that each clone shows specificity for individual peptides representing different mutations of otherwise identical peptides from ras, indicating that the amino acid representing the mutation forms an essential part of the site recognized by the T cell and that each clone may recognize several peptides of different length derived from the same mutated product, one crucial point remains to be elucidated. In order to retain functional competence in vivo (i.e. for prophylactic and therapeutic purposes), T cells/clones derived by specific stimulation by synthetic peptides must overlap in their specificity with peptides derived from the cancer cells.

We accordingly tested PBMC from several cancer patients that had tumours where high incidences of ras mutations have been reported, for evidence of previous recognition of ras derived peptides (i.e. memory T cell responses). Of several patients showing evidence of prior T cell stimulation, one was selected for further studies. Results recorded in FIG. 9 show that a patient with a follicular thyroid carcinoma was capable of responding to peptide 23. Response was synergistically enhanced by the addition of recombinant human IL-2. The response was confirmed in a second experiment (FIG. 10), using higher number of cells and a higher concentration of peptide 23. One week after stimulation with peptide 23, the culture was restimulated, this time with five different peptides derived from ras around amino acid 61. Only peptide 23 was capable of restimulating the cells, demonstrating exclusive specificity for this peptide (FIG. 11). T cell clones from the patients were established by cloning from bulk culture on day 3 of restimulation using the protocol outlined in FIG. 1. Several hundred T cell clones were obtained, and the results of four of these clones are shown in FIG. 12. Clone 10, 14, 15 and 23 all respond strongly to peptide 23. The clones are HLA-DQ restricted (inhibition with mAb FN 81.1.1, FIG. 13 and data not shown), as predicted from our peptide blocking experiments with peptide 23 using the DQ restricted clone E (FIG. 7). The capacity of peptide 23 to elicit a strong T cell response in a cancer patient, in a classical memory T cell assay, strongly suggests that the T cells have encountered an identical or very similar peptide in vivo.

In order to further investigate this, we synthesized a series of truncated forms of the peptide 23, and tested their capacity to stimulate clone 15. Data given in FIG. 14 show that the N terminal amino acids Asp in position 54 and Ile in position 55 are critical for recognition by clone 15. Removal of Asp 54 strongly reduces the response, and removal of Ile 55 totally abrogates the response. As shown in FIG. 14, clone 15 was insensitive to the removal of the C terminal amino acids Asp 69, Arg 68, Met 67 and Ala 66. Removal of Ser 65 strongly reduced the response. Together these data indicate that the processed p21 ras peptide which originally stimulated these T cells in vivo may have contained additional amino acids from the N terminal sequence of the ras protein. We accordingly synthesized new peptides that lacked several of the C terminal amino acids that were found not to contribute to T cell recognition, but contained the new amino acids Leu 53, Leu 52 and Cys 51, derived from the natural p21 ras sequence. Data showing stimulation of clone 14 with this set of peptides are given in FIG. 15. Optimal stimulation was seen with peptide 106 which encompasses the sequence 51–67. The observation that an even stronger response is achieved with a peptide having a sequence which differs significantly from the peptide used for in vitro stimulation of the T cell giving rise to the clone, strongly indicates that peptide 106 is more representative of the peptide processed by the cancer cell and originally giving rise to an immune response than peptide 23.

It is noteworthy that the cancer type of the patient is the only one in which high incidences of ras mutations in position 61 have been reported.

Thus it is shown that the processing of the mutated ras proteins in vivo must result in peptides very similar or even identical to the synthetic peptides according to this invention. The use of synthetic peptides in order to enhance in vitro the pre-existing T cell response of cancer patients is thus highly feasible. Such in vitro expanded ras specific T cell populations may contribute to eradicating the tumour cells carrying ras mutations from the patient in a refined LAK/TIL cell approach.

With oncogene specific T cells from a cancer patient available to us, we next wanted to investigate the possible role of such cells in regulating the growth of cancer cells in vitro. We accordingly tested the effect of 61 Leu specific T cell clone 14 on the growth of the human colon carcinoma cell line HT29 in vitro. This cell line can be induced to express the same HLA DQ molecules on its cell surface, as found in the cancer patient following exposure to recombinant IFN-γ. The results in FIG. 20 show that the growth of IFN-γ treated cancer cells preincubated with the oncogene peptide, peptide 106, is strongly inhibited by the presence of the T cell clone recognizing this peptide in the context of HLA-DQ. The inhibition was dependent on the number of the cells added to the culture and the peptide concentration used. Control cancer cells treated with IFN-γ alone were not influenced by the presence of this clone. These functional studies further indicate the usefulness of the peptides according to the invention for use in cancer therapy.

Synthesis

The peptides were synthesized by using continuous flow solid phase peptide synthesis (Biolynx 4170 synthesizer, Pharmacia LKB). N-α-Fmoc-amino acids with appropriate side chain protection (Ser(tBu), Thr(tBu), Lys(Boc), His (Trt), Arg(Pmc), Cys(Trt), Asp(O-tBu), Glu(O-tBu)) were used. The Fmoc-amino acids were activated by TBTU prior to coupling. 20% piperidine in DMF was used for selective removal of Fmoc after each coupling. Detachment from the resin and final removal of side chain protection was performed by 95% TFA (aq.). The peptides were purified and analysed by reversed phase (C18) HPLC (Shimadzu LC8A). Amino acid analysis was carried out using the PICO-Tag method (Waters Millipore Inc.).

The following peptides and peptide fragments were synthesized by this method:

A1). ras peptides of the following sequence having mutation points in position 12 or 13:

```
 6   7   8   9  10  11  12  13  14  15  16  17  18  19

Leu-Val-Val-Val-Gly-Ala-Gly-Val-Val-Gly-Lys-Ser-Ala-Leu  (SEQ ID NO. 31)
```

Other synthesized peptides having the sequence 1–25 of the normal ras peptide, but carrying mutations in position 12 or 13 will appear from Table 8.

A2) ras peptides of the following sequence having mutation points in position 12 or 13 and additional amino acids at one end not belonging to the natural sequence of the ras proteins:

```
 6   7   8   9  10  11  12  13  14  15  16  17  18  19  20  21

Leu-Val-Val-Val-Gly-Ala-Gly-Gly-Val-Gly-Lys-Ser-Ala-Leu-Ala-Leu  (SEQ ID NO. 1)

Leu-Val-Val-Val-Gly-Ala-Asp-Gly-Val-Gly-Lys-Ser-Ala-Leu-Ala-Leu  (SEQ ID NO. 2)

Leu-Val-Val-Val-Gly-Ala-Val-Gly-Val-Gly-Lys-Ser-Ala-Leu-Ala-Leu  (SEQ ID NO. 3)

Leu-Val-Val-Val-Gly-Ala-Cys-Gly-Val-Gly-Lys-Ser-Ala-Leu-Ala-Leu  (SEQ ID NO. 4)

Leu-Val-Val-Val-Gly-Ala-Ser-Gly-Val-Gly-Lys-Ser-Ala-Leu-Ala-Leu  (SEQ ID NO. 5)

Leu-Val-Val-Val-Gly-Ala-Lys-Gly-Val-Gly-Lys-Ser-Ala-Leu-Ala-Leu  (SEQ ID NO. 6)
```

Leu-Val-Val-Val-Gly-Ala-Arg-Gly-Val-Gly-Lys-Ser-Ala-Leu-Ala-Leu (SEQ ID NO. 7)

Leu-Val-Val-Val-Gly-Ala-Ala-Gly-Val-Gly-Lys-Ser-Ala-Leu-Ala-Leu (SEQ ID NO. 8)

Leu-Val-Val-Val-Gly-Ala-Gly-Val-Val-Gly-Lys-Ser-Ala-Leu-Ala-Leu (SEQ ID NO. 9)

Leu-Val-Val-Val-Gly-Ala-Gly-Asp-Val-Gly-Lys-Ser-Ala-Leu-Ala-Leu (SEQ ID NO. 10)

A3) ras peptides of the following sequence having mutation points in position 12 or 13 and having truncated N-terminal or C-terminal ends:

```
6    7    8    9    10   11   12   13   14   15   16   17   18   19   20
     Val-Val-Val-Gly-Ala-Ala-Gly-Val-Gly-Lys-Ser-Ala (SEQ ID NO. 30)
          Val-Val-Gly-Ala-Ala-Gly-Val-Gly-Lys-Ser-Ala (SEQ ID NO. 29)
     Val-Val-Val-Gly-Ala-Ala-Gly-Val-Gly-Lys-Ser (SEQ ID NO. 28)
          Val-Val-Gly-Ala-Ala-Gly-Val-Gly-Lys-Ser (SEQ ID NO. 27)
Leu-Val-Val-Val-Gly-Ala-Ala-Gly-Val-Gly-Lys-Ser-Ala (SEQ ID NO. 18)
Leu-Val-Val-Val-Gly-Ala-Ala-Gly-Val-Gly-Lys-Ser (SEQ ID NO. 19)
Leu-Val-Val-Val-Gly-Ala-Ala-Gly-Val-Gly-Lys (SEQ ID NO. 20)
Leu-Val-Val-Val-Gly-Ala-Ala-Gly-Val-Gly (SEQ ID NO. 21)
     Val-Val-Val-Gly-Ala-Ala-Gly-Val-Gly-Lys-Ser-Ala-Leu-Ala-Leu (SEQ ID NO. 22)
          Val-Val-Gly-Ala-Ala-Gly-Val-Gly-Lys-Ser-Ala-Leu-Ala-Leu (SEQ ID NO. 23)
               Val-Gly-Ala-Ala-Gly-Val-Gly-Lys-Ser-Ala-Leu-Ala-Leu (SEQ ID NO. 24)
                    Gly-Ala-Ala-Gly-Val-Gly-Lys-Ser-Ala-Leu-Ala-Leu (SEQ ID NO. 25)
                         Ala-Ala-Gly-Val-Gly-Lys-Ser-Ala-Leu-Ala-Leu (SEQ ID NO. 26)
Leu-Val-Val-Val-Gly-Ala-Gly-Val-Val-Gly-Lys-Ser-Ala (SEQ ID NO. 32)
Leu-Val-Val-Val-Gly-Ala-Gly-Val-Val-Gly-Lys-Ser (SEQ ID NO. 33)
Leu-Val-Val-Val-Gly-Ala-Gly-Val-Val-Gly-Lys (SEQ ID NO. 34)
Leu-Val-Val-Val-Gly-Ala-Gly-Val-Val-Gly (SEQ ID NO. 35)
     Val-Val-Val-Gly-Ala-Gly-Val-Val-Gly-Lys-Ser-Ala-Leu-Ala-Leu (SEQ ID NO. 36)
          Val-Val-Gly-Ala-Gly-Val-Val-Gly-Lys-Ser-Ala-Leu-Ala-Leu (SEQ ID NO. 37)
               Val-Gly-Ala-Gly-Val-Val-Gly-Lys-Ser-Ala-Leu-Ala-Leu (SEQ ID NO. 38)
                    Ala-Gly-Val-Val-Gly-Lys-Ser-Ala-Leu-Ala-Leu (SEQ ID NO. 39)
```

B). ras peptides with a mutation in position 61:

```
54   55   56   57   58   59   60   61   62   63   64   65   66   67   68   69
Asp-Ile-Leu-Asp-Thr-Ala-Gly-Leu-Glu-Glu-Tyr-Ser-Ala-Met-Arg-Asp (SEQ ID NO. 14)
Asp-Ile-Leu-Asp-Thr-Ala-Gly-Arg-Glu-Glu-Tyr-Ser-Ala-Met-Arg-Asp (SEQ ID NO. 12)
Asp-Ile-Leu-Asp-Thr-Ala-Gly-Lys-Glu-Glu-Tyr-Ser-Ala-Met-Arg-Asp (SEQ ID NO. 13)
Asp-Ile-Leu-Asp-Thr-Ala-Gly-His-Glu-Glu-Tyr-Ser-Ala-Met-Arg-Asp (SEQ ID NO. 15)
```

C). abl—bcr fusion gene peptide:

```
Ile-Pro-Leu-Thr-Ile-Asn-Lys-Glu-Glu-Ala-Leu-Gln-
Arg-Pro-Val-Ala-Ser-Asp-Phe-Glu (SEQ ID NO. 95)
Ala-Thr-Gly-Phe-Lys-Gln-Ser-Ser-Lys-Ala-Leu-Gln-
Arg-Pro-Val-Ala-Ser-Asp-Phe-Glu (SEQ ID NO. 96)
``` d). egf receptor peptide and retinoid receptor peptide

```
Ser-Arg-Ala-Leu-Glu-Glu-Lys-Lys-Gly-Asn-Tyr-Val- (SEQ ID NO. 99)
Val-Thr-Asp-His-Gly
Leu-Ser-Ser-Cys-Ile-Thr-Gln-Gly-Lys-Ala-Ile-Glu-
Thr-Gln-Ser-Ser-Ser-Glu-Glu (SEQ ID NO. 100)
```

TABLE 1

SYNTHETIC p21 ras PEPTIDES USED FOR IN VITRO T CELL STIMULATION.

```
      p21 Gly 12 mutations: (SEQ ID NO. 1)
p37:  Leu-Val-Val-Val-Gly-Ala-Gly-Gly-Val-Gly-Lys-Ser-Ala-Leu-Ala-Leu (SEQ ID NO. 2)
p38:  -----------------------Asp------------------------------------ (SEQ ID NO. 3)
p39:  -----------------------Val------------------------------------ (SEQ ID NO. 4)
p40:  -----------------------Cys------------------------------------ (SEQ ID NO. 5)
p41:  -----------------------Ser------------------------------------ (SEQ ID NO. 6)
p42:  -----------------------Lys------------------------------------ (SEQ ID NO. 7)
p44:  -----------------------Arg------------------------------------ (SEQ ID NO. 8)
p45:  -----------------------Ala------------------------------------
      p21 Gly 13 mutations:
p43:  -----------------------Gly-Val-------------------------------- (SEQ ID NO. 9)
p46:  ---------------------------Asp-------------------------------- (SEQ ID NO. 10)
      p21 Gln 61 mutations:
p22:  Asp-Ile-Leu-Asp-Thr-Ala-Gly-Gln-Glu-Glu-Tyr-Ser-Ala-Met-Arg-Asp (SEQ ID NO. 11)
p20:  -----------------------Arg------------------------------------ (SEQ ID NO. 12)
p21:  -----------------------Lys------------------------------------ (SEQ ID NO. 13)
p23:  -----------------------Leu------------------------------------ (SEQ ID NO. 14)
p24:  -----------------------His------------------------------------ (SEQ ID NO. 15)
      p21 Leu 61 mutation:
p169: Leu-Asp-Ile-Leu-Asp-Thr-Ala-Gly-Leu-Glu-Glu-Phe-Gly-Ala-Met (SEQ ID NO. 16)
```

TABLE 2

TRUNCATED p21 ras PEPTIDES USED FOR IN VITRO T CELL PROLIFERATION ASSAYS

```
p45 Leu-Val-Val-Val-Gly-Ala-Ala-Gly-Val-Gly-Lys-Ser-Ala-Leu-Ala-Leu (SEQ ID NO. 8)
p74 Leu-Val-Val-Val-Gly-Ala-Ala-Gly-Val-Gly-Lys-Ser-Ala-Leu (SEQ ID NO. 17)
p75 Leu-Val-Val-Val-Gly-Ala-Ala-Gly-Val-Gly-Lys-Ser-Ala (SEQ ID NO. 18)
```

TABLE 2-continued

TRUNCATED p21 ras PEPTIDES USED FOR IN VITRO T CELL PROLIFERATION ASSAYS p76 Leu-Val-Val-Val-Gly-Ala-Ala-Gly-Val-Gly-Lys-Ser (SEQ ID NO. 19)

p77 Leu-Val-Val-Val-Gly-Ala-Ala-Gly-Val-Gly-Lys (SEQ ID NO. 20)

p78 Leu-Val-Val-Val-Gly-Ala-Ala-Gly-Val-Gly (SEQ ID NO. 21)

p69     -Val-Val-Gly-Ala-Ala-Gly-Val-Gly-Lys-Ser-Ala-Leu-Ala-Leu (SEQ ID NO. 22)

p70         -Val-Gly-Ala-Ala-Gly-Val-Gly-Lys-Ser-Ala-Leu-Ala-Leu (SEQ ID NO. 23)

p71             -Val-Gly-Ala-Ala-Gly-Val-Gly-Lys-Ser-Ala-Leu-Ala-Leu (SEQ ID NO. 24)

p72                 -Gly-Ala-Ala-Gly-Val-Gly-Lys-Ser-Ala-Leu-Ala-Leu (SEQ ID NO. 25)

p73                     -Ala-Ala-Gly-Val-Gly-Lys-Ser-Ala-Leu-Ala-Leu (SEQ ID NO. 26)

p88         Val-Val-Gly-Ala-Gly-Val-Gly-Lys-Ser (SEQ ID NO. 27)

p89     Val-Val-Val-Gly-Ala-Gly-Val-Gly-Lys-Ser (SEQ ID NO. 28)

p90         Val-Val-Gly-Ala-Gly-Val-Gly-Lys-Ser-Ala (SEQ ID NO. 29)

p91     Val-Val-Val-Gly-Ala-Gly-Val-Gly-Lys-Ser-Ala (SEQ ID NO. 30)

p43 Leu-Val-Val-Val-Gly-Ala-Gly-Val-Val-Gly-Lys-Ser-Ala-Leu-Ala-Leu (SEQ ID NO. 9)

p79 Leu-Val-Val-Val-Gly-Ala-Gly-Val-Val-Gly-Lys-Ser-Ala-Leu (SEQ ID NO. 31)

p80 Leu-Val-Val-Val-Gly-Ala-Gly-Val-Val-Gly-Lys-Ser-Ala (SEQ ID NO. 32)

p81 Leu-Val-Val-Val-Gly-Ala-Gly-Val-Val-Gly-Lys-Ser (SEQ ID NO. 33)

p82 Leu-Val-Val-Val-Gly-Ala-Gly-Val-Val-Gly-Lys (SEQ ID NO. 34)

p83 Leu-Val-Val-Val-Gly-Ala-Gly-Val-Val-Gly (SEQ ID NO. 35)

p64     -Val-Val-Gly-Ala-Gly-Val-Val-Gly-Lys-Ser-Ala-Leu-Ala-Leu (SEQ ID NO. 36)

p65         -Val-Gly-Ala-Gly-Val-Val-Gly-Lys-Ser-Ala-Leu-Ala-Leu (SEQ ID NO. 37)

p66             -Val-Gly-Ala-Gly-Val-Val-Gly-Lys-Ser-Ala-Leu-Ala-Leu (SEQ ID NO. 38)

p67                 -Gly-Ala-Gly-Val-Val-Gly-Lys-Ser-Ala-Leu-Ala-Leu (SEQ ID NO. 39)

p68                     -Ala-Gly-Val-Val-Gly-Lys-Ser-Ala-Leu-Ala-Leu (SEQ ID NO. 40)

p140 Leu-Val-Val-Val-Gly-Ala-Arg-Gly-Val-Gly-Lys-Ser-Ala (SEQ ID NO. 41)

p141 Leu-Val-Val-Val-Gly-Ala-Arg-Gly-Val-Gly-Lys (SEQ ID NO. 43)

p142 Leu-Val-Val-Val-Gly-Ala-Arg-Gly-Val-Gly-Lys-Ser (SEQ ID NO. 42)

p143 Leu-Val-Val-Val-Gly-Ala-Lys-Gly-Val-Gly-Lys-Ser-Ala (SEQ ID NO. 44)

p144 Leu-Val-Val-Val-Gly-Ala-Lys-Gly-Val-Gly-Lys-Ser (SEQ ID NO. 45)

p145 Leu-Val-Val-Val-Gly-Ala-Lys-Gly-Val-Gly-Lys (SEQ ID NO. 46)

p154 Val-Val-Val-Gly-Ala-Lys-Gly-Val-Gly-Lys-Ser-Ala-Leu-Ala-Leu (SEQ ID NO. 47)

p155     Val-Val-Gly-Ala-Lys-Gly-Val-Gly-Lys-Ser-Ala-Leu-Ala-Leu (SEQ ID NO. 48)

p156 Val-Val-Val-Gly-Ala-Arg-Gly-Val-Gly-Lys-Ser-Ala-Leu-Ala-Leu (SEQ ID NO. 49)

p157     Val-Val-Gly-Ala-Arg-Gly-Val-Gly-Lys-Ser-Ala-Leu-Ala-Leu (SEQ ID NO. 50)

p177 Leu-Val-Val-Val-Gly-Ala-Arg-Gly-Val-Gly (SEQ ID NO. 51)

p178 Leu-Val-Val-Val-Gly-Ala-Arg-Gly-Val (SEQ ID NO. 52)

p179 Leu-Val-Val-Val-Gly-Ala-Lys-Gly-Val-Gly (SEQ ID NO. 53)

p180 Leu-Val-Val-Val-Gly-Ala-Lys-Gly-Val (SEQ ID NO. 54)

TABLE 2-continued

TRUNCATED p21 ras PEPTIDES USED FOR IN VITRO T CELL PROLIFERATION ASSAYS p181 Val-Gly-Ala-Lys-Gly-Val-Gly-Lys-Ser-Ala-Leu-Ala-Leu (SEQ ID NO. 55)

p182     Gly-Ala-Lys-Gly-Val-Gly-Lys-Ser-Ala-Leu-Ala-Leu (SEQ ID NO. 56)

TABLE 3

| | PRIMARY RESPONSE: | RESPONSE AFTER THE THIRD STIMULATION WITH PEPTIDE-MIXTURE III: |
|---|---|---|
| | CPM | |
| PBMC | 9798,8 | 3666,1 |
| PBMC + IL2 | 14060,7 | 29768,4 |
| PBMC + PEPTIDE-MIXTURE III | 9027,7 | 21706,9 |
| PBMC + PEPTIDE-MIXTURE III + IL2 | 14365,0 | 44909,8 |

PBMC: 100000 cells per well
IL2: 1 U/ml final dilution
Peptide mixture III: 20 micrograms of each of the five peptides 42, 43, 44, 45, 46.

The specificity of the clones:
16 out to 45 clones show specificity for the peptide mixture or a single peptide.
Peptide 42 2/45
Peptide 43 9/45
Peptide 44 1/45
Peptide 45 1/45
Peptide 46 0.45
Peptide mixture: 3/45

TABLE 5

EXAMPLES OF ONCOGENES AND TUMOR SUPPRESSOR GENES FOUND IN HUMAN TUMORS

| | neoplasms(s) | lesion |
|---|---|---|
| proto-oncogene | | |
| abl | Chronic myelogenous leukemia | translocation |
| gip. | Carcinoma of ovary and adrenal gland | point mutations |
| gsp | Adrenoma of pituitary gland; carcinoma of thyroid | point mutations |
| H-ras | Carcinoma of colon, lung and pancreas; melanoma | point mutations |
| K-ras | Acute myelogenous and lymphoblastic leukemia; carcinoma of thyroid; melanoma | point mutations |
| N-ras | Carcinoma of genito-urinary tract and thyroid; melanoma | |
| ret | Carcinoma of thyroid | rearrangement |
| trk | Carcinoma of thyroid | rearrangement |
| Tumor suppressor genes | | |
| rb1 | Retinoblastoma; osteosarcoma; carcinoma of breast, bladder and lung | point mutation |
| p53 | Astrocytoma; carcinoma of breast, colon and lung; osteosarcoma | point mutation |

TABLE 6

THE SEQUENCE OF THE AMINO-ACIDS FROM POSITION 1 TO 26
IN THE p21 H-, K- AND N-RAS PROTEIN:

Met-Thr-Glu-Tyr-Lys-Leu-Val-Val-Val-Gly-Ala-Gly-Gly-Val-
Gly-Lys-Ser-Ala-Leu-Thr-Ile-Gln-Leu-Ile-Gln-Asn (SEQ ID NO: 57)

THE SEQUENCE OF THE AMINO-ACIDS FROM POSITION 45 TO 72
IN THE p21 H-, K- AND N-RAS PROTEIN:

Val-Ile-Asp-Gly-Glu-Thr-Cys-Leu-Leu-Asp-Ile-Leu-Asp-Thr-
Als-Gly-Gln-Glu-Glu-Tyr-Ser-Ala-Met-Arg-Asp-Gln-Tyr-Met (SEQ ID NO: 58)

THE SEQUENCE OF THE AMINO-ACIDS FROM POSITION 53 TO 67
IN THE p21 R-RAS PROTEIN:

Leu-Asp-Ile-Leu-Asp-Thr-Ala-Gly-Gln-Glu-Glu-Phe-Gly-
Ala-Met (SEQ ID NO. 59)

TABLE 7

TRUNCATED p21 ras PEPTIDES USED FOR IN VITRO T CELL PROLIFERATION ASSAYS:

p124: Glu-Thr-Cys-Leu-Leu-Asp-Leu-Leu-Asp-Ile-Leu-Asp-Thr-Ala-Gly-Leu-Glu-Glu-Tyr-Ser-Ala-Met (SEQ ID NO. 60)

p125:     Thr-Cys-Leu-Leu-Asp-Leu-Leu-Asp-Ile-Leu-Asp-Thr-Ala-Gly-Leu-Glu-Glu-Tyr-Ser-Ala-Met (SEQ ID NO. 61)

p106: Cys-Leu-Leu-Asp-Ile-Leu-Asp-Thr-Ala-Gly-Leu-Glu-Glu-Tyr-Ser-Ala-Met (SEQ ID NO. 63)

p107:      Leu-------------------------------------------------------------- (SEQ ID NO. 64)

p108:           Leu--------------------------------------------------------- (SEQ ID NO. 65)

p109: Cys-Leu-Leu-Asp-Ile-Leu-Asp-Thr-Ala-Gly-Leu-Glu-Glu-Tyr-Ser (SEQ ID NO. 66)

p110:      Leu----------------------------------------------------- (SEQ ID NO. 67)

p111:           Leu------------------------------------------------ (SEQ ID NO. 68)

p188: Asp-Ile-Leu-Asp-Thr-Ala-Gly-Glu-Glu-Tyr-Ser-Ala-Met (SEQ ID NO. 69)

p 94:     Ile-Leu-Asp-Thr-Ala-Gly-Leu-Glu-Glu-Tyr-Ser-Ala-Met-Arg-Asp (SEQ ID NO. 70)

p 95:         Leu--------------------------------------------------- (SEQ ID NO. 71)

p 96:             Asp----------------------------------------------- (SEQ ID NO. 72)

p 97:                 Thr------------------------------------------- (SEQ ID NO. 73)

p 98:                     Ala--------------------------------------- (SEQ ID NO. 74)

p 99: Asp-Ile-Leu-Asp-Thr-Ala-Gly-Leu-Glu-Glu-Tyr-Ser-Ala-Met-Arg (SEQ ID NO. 75)

p100: Asp------------------------------------------Met (SEQ ID NO. 76)

p101: Asp------------------------------------------Ala (SEQ ID NO. 77)

p102: Asp------------------------------------------Ser (SEQ ID NO. 78)

p103: Asp------------------------------------------Tyr (SEQ ID NO. 79)

TABLE 8

```
         1   2   3   4   5   6   7   8   9   10  11
P 112: Met-Thr-Glu-Tyr-Lys-Leu-Val-Val-Val-Gly-Ala- 12  13  14  15  16  17  18  19  20  21  22
       Gly-Gly-Val-Gly-Lys-Ser-Ala-Leu-Thr-Ile-Gln- 23  24  25
       Leu-Ile-Gln (SEQ ID NO. 79)

1   2   3   4   5   6   7   8   9   10  11
P 113: Met-Thr-Glu-Tyr-Lys-Leu-Val-Val-Val-Gly-Ala- 12  13  14  15  16  17  18  19  20  21  22
       Val-Gly-Val-Gly-Lys-Ser-Ala-Leu-Thr-Ile-Gln- 23  24  25
       Leu-Ile-Gln (SEQ ID NO. 80)

1   2   3   4   5   6   7   8   9   10  11
P 114: Met-Thr-Glu-Tyr-Lys-Leu-Val-Val-Val-Gly-Ala- 12  13  14  15  16  17  18  19  20  21  22
       Lys-Gly-Val-Gly-Lys-Ser-Ala-Leu-Thr-Ile-Gln- 23  24  25
       Leu-Ile-Gln (SEQ ID NO. 81)

1   2   3   4   5   6   7   8   9   10  11
P 115: Met-Thr-Glu-Tyr-Lys-Leu-Val-Val-Val-Gly-Ala- 12  13  14  15  16  17  18  19  20  21  22
       Arg-Gly-Val-Gly-Lys-Ser-Ala-Leu-Thr-Ile-Gln- 23  24  25
       Leu-Ile-Gln (SEQ ID NO. 82)

1   2   3   4   5   6   7   8   9   10  11
P 116: Met-Thr-Glu-Tyr-Lys-Leu-Val-Val-Val-Gly-Ala- 12  13  14  15  16  17  18  19  20  21  22
       Ala-Gly-Val-Gly-Lys-Ser-Ala-Leu-Thr-Ile-Gln- 23  24  25
       Leu-Ile-Gln (SEQ ID NO. 83)

1   2   3   4   5   6   7   8   9   10  11
P 117: Met-Thr-Glu-Tyr-Lys-Leu-Val-Val-Val-Gly-Ala- 12  13  14  15  16  17  18  19  20  21  22
       Ser-Gly-VAl-Gly-Lys-Ser-Ala-Leu-Thr-Ile-Gln- 23  24  25
       Leu-Ile-Gln (SEQ ID NO. 84)

1   2   3   4   5   6   7   8   9   10  11
P 118: Met-Thr-Glu-Tyr-Lys-Leu-Val-Val-Val-Gly-Ala- 12  13  14  15  16  17  18  19  20  21  22
       Cys-Gly-Val-Gly-Lys-Ser-Ala-Leu-Thr-Ile-Gln-
```

TABLE 8-continued

```
                    23  24  25
                    Leu-Ile-Gln (SEQ ID NO. 85)

1   2   3   4   5   6   7   8   9   10  11
P 119:  Met-Thr-Glu-Tyr-Lys-Leu-Val-Val-Val-Gly-Ala- 12  13  14  15  16  17  18  19  20  21  22
        Asp-Gly-Val-Gly-Lys-Ser-Ala-Leu-Thr-Ile-Gln- 23  24  25
        Leu-Ile-Gln (SEQ ID NO. 86)

1   2   3   4   5   6   7   8   9   10  11
P 120:  Met-Thr-Glu-Tyr-Lys-Leu-Val-Val-Val-Gly-Ala- 12  13  14  15  16  17  18  19  20  21  22
        Gly-Val-Val-Gly-Lys-Ser-Ala-Leu-Thr-Ile-Gln- 23  24  25
        Leu-Ile-Gln (SEQ ID NO. 87)

1   2   3   4   5   6   7   8   9   10  11
P 121:  Met-Thr-Glu-Tyr-Lys-Leu-Val-Val-Val-Gly-Ala- 12  13  14  15  16  17  18  19  20  21  22
        Gly-Asp-Val-Gly-Lys-Ser-Ala-Leu-Thr-Ile-Gln- 23  24  25
        Leu-Ile-Gln (SEQ ID NO. 88)
```

TABLE 9 p158 Val-Ile-Asp-Gly-Glu-Thr-Cys-Leu-Leu-Asp-Ile-Leu-Asp-Thr-Ala-Gly-Leu-Glu-Glu-Tyr-Ser-Ala-Met-Arg-Asp-Gln-Tyr-Met (SEQ ID NO. 89)

p166 Val-Ile-Asp-Gly-Glu-Thr-Cys-Leu-Leu-Asp-Ile-Leu-Asp-Thr-Ala-Gly-Arg-Glu-Glu-Tyr-Ser-Ala-Met-Arg-Asp-Gln-Tyr-Met (SEQ ID NO. 90)

p168 Val-Ile-Asp-Gly-Glu-Thr-Cys-Leu-Leu-Asp-Ile-Leu-Asp-Thr-Ala-Gly-Lys-Glu-Glu-Tyr-Ser-Ala-Met-Arg-Asp-Gln-Tyr-Met (SEQ ID NO. 91)

p167 Val-Ile-Asp-Gly-Glu-Thr-Cys-Leu-Leu-Asp-Ile-Leu-Asp-Thr-Ala-Gly-His-Glu-Glu-Tyr-Ser-Ala-Met-Arg-Asp-Gln-Tyr-Met (SEQ ID NO. 92)

| Clone: | Peptide specificity: | Response blocked by: |
| --- | --- | --- |
| B | P-115 | anti HLA-DR mAb |
| KB16 | P-115 | anti HLA-DQ mAb |
| KB11 | P-115 | anti HLA-DP mAb |

| Peptides | Sequences | Results DQw6 IC50 (μM) | DR1 IC50 (μM) |
| --- | --- | --- | --- |
| P112 | MTEYKLVVVGAGGVGKSALTIQLIQ (SEQ ID NO. 79) | 6,02 | 1,21 |
| P113 | -----------V------------- (SEQ ID NO. 80) | 8,97 | 0,78 |
| P114 | -----------K------------- (SEQ ID NO. 81) | 2,53 | 0,55 |
| P115 | -----------R------------- (SEQ ID NO. 82) | 2,78 | 0,24 |
| P116 | -----------A------------- (SEQ ID NO. 83) | 2,68 | 0,44 |
| P117 | -----------S------------- (SEQ ID NO. 84) | 1,91 | <0,11 |
| P118 | -----------C------------- (SEQ ID NO. 85) | 10 | 1,75 |
| P119 | -----------D------------- (SEQ ID NO. 86) | 3,03 | 1,10 |
| P120 | --------------GV--------- (SEQ ID NO. 87) | 7,31 | 0,74 |
| P121 | --------------D---------- (SEQ ID NO. 88) | 2,74 | 0,31 |
| P88 | VVGAAGVGKS (SEQ ID NO. 27) | 8,97 | |
| P89 | V---------- (SEQ ID NO. 28) | 10 | |
| P90 | ----------A (SEQ ID NO. 29) | 9,98 | |
| P91 | ------------ (SEQ ID NO. 30) | 1,29 | |
| P45 | L------------LAL (SEQ ID NO. 8) | 0,90 | |
| P104 | Y----------- (SEQ ID NO. 93) | <0,33 | 0,78 |
| P34 | SGPLKAEIAQLEY (SEQ ID NO. 94) | >>10 | 0,15 |

The binding of peptides to affinity purified HLA molecules was tested by their capacity to inhibit the binding of a radio-labeled indicator peptide. To test the binding of peptides to DQw6, iodinated P104 was used as an indicator peptide. Whereas iodinated P34(derived from Influenza matrix protein aa 17–29) was used as indicator peptide to test the binding of peptides to DR1. In the table the concentration at 50% inhibition (IC50) of the binding of the indicator peptide is shown Low IC50 means good binding capacity. The peptides were tested in the concentration range from 0,33–10 μM.

We claim:

1. A method of eliciting a T cell response in a human, wherein the T cell response is specific to cancer cells expressing a mutant p21 ras oncogene protein, comprising vaccinating said human with a corresponding mutant peptide consisting of an amino acid sequence found in normal p21 ras protein (Sequence I.D. No. 57 herein) that includes at least positions 8–17 of said protein but not more than positions 1–25 of said protein, but wherein the amino acid residues at positions 12 and 13 of said sequence are not both Gly, said peptide being capable of binding to both type DQ and type DR human leucocyte antigen (HLA) molecules.

2. The method of claim 1, wherein one of the amino acid residues at positions 12 and 13 is Gly.

3. The method of claim 2, wherein the amino acid residue at position 13 is Gly.

4. The method of claim 3, wherein the amino acid residue at position 12 is selected from the group consisting of Val, Lys, Arg, Ala, Ser, Cys, and Asp.

5. The method of claim 4, wherein the peptide's amino acid sequence consists of at least positions 7–17 of normal p21 ras protein.

6. The method of claim 4, wherein the peptide's amino acid sequence consists of at least positions 6–17 of normal p21 ras protein.

7. The method of claim 4, wherein the peptide's amino acid sequence consists of at least positions 1–17 of normal p21 ras protein.

8. The method of claim 4, wherein the peptide's amino acid sequence consists of at least positions 8–18 of normal p21 ras protein.

9. The method of claim 4, wherein the peptide's amino acid sequence consists of at least positions 8–19 of normal p21 ras protein.

10. The method of claim 4, wherein the peptide's amino acid sequence consists of at least positions 8–25 of normal p21 ras protein.

11. The method of claim 5, wherein the peptide's amino acid sequence consists of at least positions 7–18 of normal p21 ras protein.

12. The method of claim 5, wherein the peptide's amino acid sequence consists of at least positions 7–19 of normal p21 ras protein.

13. The method of claim 5, wherein the peptide's amino acid sequence consists of at least positions 7–25 of normal p21 ras protein.

14. The method of claim 6, wherein the peptide's amino acid sequence consists of at least positions 6–11 of normal p21 ras protein.

15. The method of claim 6, wherein the peptide's amino acid sequence consists of at least positions 6–19 of normal p21 ras protein.

16. The method of claim 6, wherein the peptide's amino acid sequence consists of at least positions 6–25 of normal p21 ras protein.

17. The method of claim 7, wherein the peptide's amino acid sequence consists of at least positions 1–18 of normal p21 ras protein.

18. The method of claim 7, wherein the peptide's amino acid sequence consists of at least positions 1–19 of normal p21 ras protein.

19. The method of claim 7, wherein the peptide's amino acid sequence consists of at least positions 1–25 of normal p21 ras protein.

20. The method of claim 19, wherein the peptide is selected from the group consisting of the peptides set forth in Sequence I.D. Nos. 80, 81, 82, 83, 84, 85, and 86 herein.

21. The method of claim 2, wherein the amino acid at position 12 is Gly.

22. The method of claim 21, wherein the amino acid at position 13 is either Val or Asp.

23. The method of claim 21, wherein the peptide's amino acid sequence consists of at least positions 7–17 of normal p21 ras protein.

24. The method of claim 21, wherein the peptide's amino acid sequence consists of at least positions 6–17 of normal p21 ras protein.

25. The method of claim 21, wherein the peptide's amino acid sequence consists of at least positions 1–17 of normal p21 ras protein.

26. The method of claim 21, wherein the peptide's amino acid sequence consists of at least positions 8–18 of normal p21 ras protein.

27. The method of claim 21, wherein the peptide's amino acid sequence consists of at least positions 8–19 of normal p21 ras protein.

28. The method of claim 21, wherein the peptide's amino acid sequence consists of at least positions 8–25 of normal p21 ras protein.

29. The method of claim 23, wherein the peptide's amino acid sequence consists of at least positions 7–18 of normal p21 ras protein.

30. The method of claim 23, wherein the peptide's amino acid sequence consists of at least positions 7–25 of normal p21 ras protein.

31. The method of claim 23, wherein the peptide's amino acid sequence consists of at least positions 7–25 of normal p21 ras protein.

32. The method of claim 24, wherein the peptide's amino acid sequence consists of at least positions 6–18 of normal p21 ras protein.

33. The method of claim 24, wherein the peptide's amino acid sequence consists of at least positions 6–19 of normal p21 ras protein.

34. The method of claim 24, wherein the peptide's amino acid sequence consists of at least positions 6–25 of normal p21 ras protein.

35. The method of claim 25, wherein the peptide's amino acid sequence consists of at least positions 1–18 of normal p21 ras protein.

36. The method of claim 25, wherein the peptide's amino acid sequence consists of at least positions 1–19 of normal p21 ras protein.

37. The method of claim 25, wherein the peptide's amino acid sequence consists of positions 1–25 of normal p21 ras protein.

38. The method of claim 37, wherein the peptide is selected from the group consisting of the peptides set forth in Sequence I.D. Nos. 87 and 88 herein.

39. The method of claim 1, wherein the peptide is administered together with a cytokine.

40. The method of claim 2, wherein the peptide is administered together with a cytokine.

41. The method of claim 40, wherein the cytokine is interleukin-2.

42. The method of claim 40, wherein the peptide is administered in the form of a lipopeptide conjugate.

43. The method of claim 41, wherein the peptide is administered in the form of a lipopeptide conjugate.

44. A method of stimulating the proliferation of T cells from a human patient afflicted with a type of cancer that is associated with a p21 ras oncogene, said T cells being specific to cancer cells expressing a mutant p21 ras oncogene protein, which method comprises the following steps:
   i) withdrawing peripheral blood from said human;
   ii) separating mononuclear cells from said withdrawn blood; and
   iii) incubating said mononuclear cells with a mutant peptide corresponding to the mutant p21 ras oncogene protein expressed by the cancer cells, said peptide having an amino acid sequence found in normal p21 ras protein (Sequence I.D. No. 57 herein) that consists of at least positions 8–17 of said protein but not more than positions 1 25 of said protein, but wherein the amino acid residues at positions 12 and 13 of said sequence are not both Gly, said peptide being capable of binding to both type DQ and type DR human leucocyte antigen (HLA) molecules.

45. The method of claim 44, wherein the amino acid residue at position 13 is Gly.

46. The method of claim 45, wherein the amino acid residue at position 12 is selected from the group consisting of Val, Lys, Arg, Ala, Ser, Cys, and Asp.

47. The method of claim 46, wherein the peptide's amino acid sequence consists of at least positions 7–17 of normal p21 ras protein.

48. The method of claim 46, wherein the peptide's amino acid sequence consists of at least positions 6–17 of normal p21 ras protein.

49. The method of claim 46, wherein the peptide's amino acid sequence consists of at least positions 8–18 of normal p21 ras protein.

50. The method of claim 46, wherein the peptide's amino acid sequence consists of at least positions 8–19 of normal p21 ras protein.

51. The method of claim 47, wherein the peptide's amino acid sequence consists of at least positions 7–18 of normal p21 ras protein.

52. The method of claim 47, wherein the peptide's amino acid sequence consists of at least positions 7–19 of normal p21 ras protein.

53. The method of claim 48, wherein the peptide's amino acid sequence consists of at least positions 6–18 of normal p21 ras protein.

54. The method of claim 48, wherein the peptide's amino acid sequence consists of at least positions 6–19 of normal p21 ras protein.

55. The method of claim 54, wherein the peptide is selected from the group consisting of the peptides set forth in Sequence I.D. Nos. 80, 81, 82, 83, 84, 85, and 86 herein.

56. The method of claim 44, wherein the amino acid residue at position 12 is Gly.

57. The method of claim 56, wherein the amino acid residue at position 13 is either Val or Asp.

58. The method of claim 56, wherein the peptide's amino acid sequence consists of at least positions 7–17 of normal p21 ras protein.

59. The method of claim 56, wherein the peptide's amino acid sequence consists of at least positions 6–17 of normal p21 ras protein.

60. The method of claim 56, wherein the peptide's amino acid sequence consists of at least positions 8–18 of normal p21 ras protein.

61. The method of claim 56, wherein the peptide's amino acid sequence consists of at least positions 8–19 of normal p21 ras protein.

62. The method of claim 58, wherein the peptide's amino acid sequence consists of at least positions 7–18 of normal p21 ras protein.

63. The method of claim 58, wherein the peptide's amino acid sequence consists of at least positions 7–19 of normal p21 ras protein.

64. The method of claim 59, wherein the peptide's amino acid sequence consists of at least positions 6–18 of normal p21 ras protein.

65. The method of claim 59, wherein the peptide's amino acid sequence consists of at least positions 6–19 of normal p21 ras protein.

66. The method of claim 65, wherein the peptide is selected from the group consisting of the peptides set forth in Sequence I.D. Nos. 87 and 88 herein.

67. A peptide consisting of an amino acid sequence found in normal p21 ras protein (Sequence I.D. No. 57 herein) that includes at least positions 8–17 of said protein but not more than positions 1–25 of said protein, but wherein the amino acid residues at positions 12 and 13 of said sequence are not both Gly, said peptide being capable of binding to both type DQ and type DR human leucocyte antigen (HLA) molecules.

68. The peptide of claim 67, wherein one of the amino acid residues at positions 12 and 13 is Gly.

69. The peptide of claim 68, wherein the amino acid residue at position 13 is Gly.

70. The peptide of claim 69, wherein the amino acid residue at position 12 is selected from the group consisting of Val, Lys, Arg, Ala, Ser, Cys, and Asp.

71. The peptide of claim 70, wherein the peptide's amino acid sequence consists of at least positions 7–17 of normal p21 ras protein.

72. The peptide of claim 70, wherein the peptide's amino acid sequence consists of at least positions 6–17 of normal p21 ras protein.

73. The peptide of claim 70, wherein the peptide's amino acid sequence consists of at least positions 1–17 of normal p21 ras protein.

74. The peptide of claim 70, wherein the peptide's amino acid sequence consists of at least positions 8–18 of normal p21 ras protein.

75. The peptide of claim 70, wherein the peptide's amino acid sequence consists of at least positions 8–19 of normal p21 ras protein.

76. The peptide of claim 70, wherein the peptide's amino acid sequence consists of at least positions 8–25 of normal p21 ras protein.

77. The peptide of claim 71, wherein the peptide's amino acid sequence consists of at least positions 7–18 of normal p21 ras protein.

78. The peptide of claim 71, wherein the peptide's amino acid sequence consists of at least positions 7–19 of normal p21 ras protein.

79. The peptide of claim 71, wherein the peptide's amino acid sequence consists of at least positions 7–25 of normal p21 ras protein.

80. The peptide of claim 72, wherein the peptide's amino acid sequence consists of at least positions 6–18 of normal p21 ras protein.

81. The peptide of claim 72, wherein the peptide's amino acid sequence consists of at least positions 6–19 of normal p21 ras protein.

82. The peptide of claim 72, wherein the peptide's amino acid sequence consists of at least positions 6–25 of normal p21 ras protein.

83. The peptide of claim 73, wherein the peptide's amino acid sequence consists of at least positions 1–18 of normal p21 ras protein.

84. The peptide of claim 73, wherein the peptide's amino acid sequence consists of at least positions 1–19 of normal p21 ras protein.

85. The peptide of claim 73, wherein the peptide's amino acid sequence consists of positions 1–25 of normal p21 ras protein.

86. A peptide selected from the group consisting of the peptides set forth in Sequence I.D. Nos. 80, 81, 82, 83, 84, 85, and 86 herein.

87. The peptide of claim 68, wherein the amino acid at position 12 is Gly.

88. The peptide of claim 87, wherein the amino acid at position 13 is either Val or Asp.

89. The peptide of claim 87, wherein the peptide's amino acid sequence consists of at least positions 7–17 of normal p21 ras protein.

90. The peptide of claim 87, wherein the peptide's amino acid sequence consists of at least positions 6–17 of normal p21 ras protein.

91. The peptide of claim 87, wherein the peptide's amino acid sequence consists of at least positions 1–17 of normal p21 ras protein.

92. The peptide of claim 87, wherein The peptide's amino acid sequence consists of at least positions 8–18 of normal p21 ras protein.

93. The peptide of claim 87, wherein the peptide's amino acid sequence consists of at least positions 8–19 of normal p21 ras protein.

94. The peptide of claim 87, wherein the peptide's amino acid sequence consists of at least positions 8–25 of normal p21 ras protein.

95. The peptide of claim 89, wherein the peptide's amino acid sequence consists of at least positions 7–18 of normal p21 ras protein.

96. The peptide of claim 89, wherein the peptide's amino acid sequence consists of at least positions 7–19 of normal p21 ras protein.

97. The peptide of claim 89, wherein the peptide's amino acid sequence consists of a least positions 7–25 of normal p21 ras protein.

98. The peptide of claim 90, wherein the peptide's amino acid sequence consists of at least positions 6–18 of normal p21 ras protein.

99. The peptide of claim 90, wherein the peptide's amino acid sequence consists of at least positions 6–19 of normal p21 ras protein.

100. The peptide of claim 90, wherein the peptide's amino acid sequence consists of at least positions 6–25 of normal p21 ras protein.

101. The peptide of claim 91, wherein the peptide's amino acid sequence consists of at least positions 1–18 of normal p21 ras protein.

102. The peptide of claim 91, wherein the peptide's amino acid sequence consists of at least positions 1–19 of normal p21 ras protein.

103. The peptide of claim 91, wherein the peptide's amino acid sequence consists of positions 1–25 of normal p21 ras protein.

104. A peptide selected from the group consisting of the peptides set forth in Sequence I.D. Nos. 87 and 88 herein.

105. A peptide according to claim 68, wherein the peptide is as set forth in Sequence I.D. No 17 (p74).

106. A peptide according to claim 68, wherein the peptide is as set forth in Sequence I.D. No 18 (p75).

107. A peptide according to claim 68, wherein the peptide is as set forth in Sequence I.D. No 19 (p76).

108. A peptide according to claim 68, wherein the peptide is as set forth in Sequence I.D. No 31 (p79).

109. A peptide according to claim 68, wherein the peptide is as set forth in Sequence I.D. No 32 (p80).

110. A peptide according to claim 68, wherein the peptide is as set forth in Sequence I.D. No 33 (p81).

111. A peptide according to claim 68, wherein the peptide is as set forth in Sequence I.D. No 27 (p88).

112. A peptide according to claim 68, wherein the peptide is as set forth in Sequence I.D. No 28 (p89).

113. A peptide according to claim 68, wherein the peptide is as set forth in Sequence I.D. No 29 (p90).

114. A peptide according to claim 68, wherein the peptide is as set forth in Sequence I.D. No 30 (p91).

115. A vaccine comprising the peptide of claim 67 in combination with at least one pharmaceutically acceptable carrier.

116. A vaccine comprising the peptide of claim 68 in combination with at least one pharmaceutically acceptable carrier.

117. A vaccine comprising the peptide of claim 69 in combination with at least one pharmaceutically acceptable carrier.

118. A vaccine comprising the peptide of claim 70 in combination with at least one pharmaceutically acceptable carrier.

119. A vaccine comprising the peptide of claim 81 in combination with at least one pharmaceutically acceptable carrier.

120. A vaccine comprising the peptide of claim 86 in combination with at least one pharmaceutically acceptable carrier.

121. A vaccine comprising the peptide of claim 87 in combination with at least one pharmaceutically acceptable carrier.

122. A vaccine comprising the peptide of claim 88 in combination with at least one pharmaceutically acceptable carrier.

123. A vaccine comprising the peptide of claim 89 in combination with at least one pharmaceutically acceptable carrier.

124. A vaccine comprising the peptide of claim 99 in combination with at least one pharmaceutically acceptable carrier.

125. A vaccine comprising the peptide of claim 104 in combination with at least one pharmaceutically acceptable carrier.

126. A vaccine comprising the peptide of claim 105 in combination with at least one pharmaceutically acceptable carrier.

127. A vaccine comprising the peptide of claim 106 in combination with at least one pharmaceutically acceptable carrier.

128. A vaccine comprising the peptide of claim 107 in combination with at least one pharmaceutically acceptable carrier.

129. A vaccine comprising the peptide of claim 108 in combination with at least one pharmaceutically acceptable carrier.

130. A vaccine comprising the peptide of claim 109 in combination with at least one pharmaceutically acceptable carrier.

131. A vaccine comprising the peptide of claim 110 in combination with at least one pharmaceutically acceptable carrier.

132. A vaccine comprising the peptide of claim 111 in combination with at least one pharmaceutically acceptable carrier.

133. A vaccine comprising the peptide of claim 112 in combination with at least one pharmaceutically acceptable carrier.

134. A vaccine comprising the peptide of claim 113 in combination with at least one pharmaceutically acceptable carrier.

135. A vaccine comprising the peptide of claim 114 in combination with at least one pharmaceutically acceptable carrier.

136. The vaccine of claim 117, wherein the vaccine comprises the peptide in at least two molecular forms that differ only as regards the non-Gly amino acid residue at position 12, and wherein said at least two different non-Gly amino acid residues at position 12 are selected from the group consisting of Val, Lys, Arg, Ala, Ser, Cys, and Asp.

137. The method of claim 1, wherein the human is afflicted with follicular thyroid carcinoma.

138. The method of claim 1, wherein the human is a healthy person.

* * * * *

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.  Page 1 of 14

It is certified that error appears in the above-identified patent and that said Letters Patent is hereby corrected as shown below:

ON THE COVER PAGE
  [73] Assignee: "Norway" should read --Oslo, Norway--.

COLUMN 1
  Line 53, "12." should read --12--.

COLUMN 2
  Line 47, before "In" a new paragraph should be inserted.

COLUMN 4
  Line 59, "teeted" should read --tested--.

COLUMN 5
  Line 15, "position" should read --positions--.

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 6
  Line 20, "NO:" should read --NO.--.

COLUMN 7
  Line 44, "position" should read --positions--; and
  Line 64, "FIG. 2 and FIGS. 2a-2e" should read
--FIGS. 2A-2E--.

COLUMN 8
  Line 15, "FIGS. 3a-3d" should read --FIGS. 3A-3D--;
  Line 18, "FIG. 2" should read --FIGS. 2A-2E--;
  Line 23, "FIG. 2" should read --FIGS. 2A-2E--;
  Line 26, "FIG. 2" should read --FIGS. 2A-2E--;
  Line 31, "FIG. 2" should read --FIGS. 2A-2E--;
  Line 41, "FIG. 2" should read --FIGS. 2A-2E--; and
  Line 63, "FIG. 2" should read --FIGS. 2A-2E--.

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.          Page 3 of 14

It is certified that error appears in the above-identified patent and that said Letters Patent is hereby corrected as shown below:

COLUMN 9
```
  Line 4, "was" should read --were--;
  Line 12, "FIGS. 12a-12d" should read --FIGS. 12A-12D--;
  Line 14, "FIG. 2" should read --FIGS. 2A-2E--;
  Line 19, "FIG. 2 and 3" should read --FIGS. 2A-2E and
3A-3D--;
  Line 24, "FIG. 2" should read --FIGS. 2A-2E--;
  Line 40, "FIGS. 17a-17b" should read --FIGS. 17A-17B--;
  Line 48, "FIGS. 18a-18b" should read --FIGS. 18A-18D--; and
"result" should read --results--;
  Line 56, "FIGS. 19a-19b" should read --FIGS. 19A-19B--; and
  Line 59, "p-116))" should read --p-116).--.
```

UNITED STATES PATENT AND TRADEMARK OFFICE
CERTIFICATE OF CORRECTION

PATENT NO.   :  5,961,978

DATED        :  October 5, 1999

INVENTOR(S)  :  GUSTAV GAUDERNACK, ET AL.          Page 4 of 14

It is certified that error appears in the above-identified patent and that said Letters Patent is hereby corrected as shown below:

COLUMN 10
  Line 50, "(FIG. 2a)." should read --(FIG. 2A).--;
  Line 55, "(FIG. 3a)." should read --(FIG. 3A).--;
  Line 58, "(FIG. 2b)." should read --(FIG. 2B).--;
  Line 61, "(FIG. 3b)." should read --(FIG. 3B).--; and
  Line 64, "(FIG. 2c)." should read --(FIG. 2C).--.

COLUMN 11
  Line 2,  "(FIG. 3c)." should read --(FIG. 3C).--;
  Line 9,  "(FIG. 2d)," should read --(FIG. 2D),--;
  Line 10, "(FIG. 2e)." should read --(FIG. 2E).--;
  Line 19, "(FIG. 3d)." should read --(FIG. 3D).--;
  Line 40, "position" should read --positions--; and
  Line 52, "end." should read --ends.--.

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 12
```
 Line  2, "clone" should read --clones--;
 Line  7, "NO:" should read --NO.--;
 Line  9, "NO:" should read --NO.--;
 Line 26, "FIGS. 17a-17b" should read --FIGS. 17A-17B--;
 Line 34, "FIGS. 17a-17b" should read --FIGS. 17A-17B--;
 Line 35, "clone" should read --clones--;
 Line 36, "NO:" should read --NO.--;
 Line 38, "NO:" should read --NO.--;
 Line 43, "FIG. 18." should read --FIGS. 18A-18D--;
 Line 64, "(Clone" should read --(clones--; and
 Line 65, "(clone" should read --(clones--.
```

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 13
  Line 27, "FIGS. 19a-19b." should read --FIGS. 19A-19B.--; and
  Line 54, "indicate" should read --indicated--.

COLUMN 14
  Line 15, "contain" should read --contains--; and
  Line 65, "FIG. 12. Clone" should read
--FIGS. 12A-12D. Clones--.

UNITED STATES PATENT AND TRADEMARK OFFICE
CERTIFICATE OF CORRECTION

PATENT NO. : 5,961,978
DATED : October 5, 1999
INVENTOR(S) : GUSTAV GAUDERNACK, ET AL.

Page 7 of 14

It is certified that error appears in the above-identified patent and that said Letters Patent is hereby corrected as shown below:

COLUMN 19, Table 1

```
    "p21 Gly 12 mutations: (SEQ ID NO. 1)
p37: Leu-Val-Val-Val-Gly-Ala-Gly-Gly-Val-Gly-Lys-Ser-Ala-Leu-Ala-Leu (SEQ ID NO. 2)

p38: ------------------------Asp------------------------------------ (SEQ ID NO. 3)

p39: ------------------------Val------------------------------------ (SEQ ID NO. 4)

p40: ------------------------Cys------------------------------------ (SEQ ID NO. 5)

p41: ------------------------Ser------------------------------------ (SEQ ID NO. 6)

p42: ------------------------Lys------------------------------------ (SEQ ID NO. 7)

p44: ------------------------Arg------------------------------------ (SEQ ID NO. 8)

p45: ------------------------Ala------------------------------------"
```

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.   Page 8 of 14

It is certified that error appears in the above-identified patent and that said Letters Patent is hereby corrected as shown below:

COLUMN 19, TABLE 1 Cont'd.
should read

```
  --p21 Gly 12 mutations:
p37: Leu-Val-Val-Val-Gly-Ala-Gly-Gly-Val-Gly-Lys-Ser-Ala-Leu-Ala-Leu (SEQ ID NO. 1)

p38: ----------------------Asp------------------------------------ (SEQ ID NO. 2)

p39: ----------------------Val------------------------------------ (SEQ ID NO. 3)

p40: ----------------------Cys------------------------------------ (SEQ ID NO. 4)

p41: ----------------------Ser------------------------------------ (SEQ ID NO. 5)

p42: ----------------------Lys------------------------------------ (SEQ ID NO. 6)

p44: ----------------------Arg------------------------------------ (SEQ ID NO. 7)

p45: ----------------------Ala------------------------------------ (SEQ ID NO. 8)
--; and
```

"p21 Leu 61 mutation:" should read --p21 Leu 61 mutations:--.

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 21, TABLE 2
  After p88: "Ala" should read --Ala-Ala--;
  After p89: "Ala" should read --Ala-Ala--;
  After p90: "Ala" (first occurrence) should read --Ala-Ala--; and
  After p91: "Ala" (first occurrence) should read --Ala-Ala--.

COLUMN 23, TABLE 5
  "neoplasms(s)" should read --neoplasm(s)--.

COLUMN 24, TABLE 5
  "neoplasms(s)" should read --neoplasm(s)--; and
  After "Carcinoma of genito-": the third column should read --point mutations--.

COLUMN 25, TABLE 7
  After p124: "Leu-Leu-Asp-Leu-Leu-Asp" should read --Leu-Leu-Asp--;

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

Page 10 of 14

It is certified that error appears in the above-identified patent and that said Letters Patent is hereby corrected as shown below:

```
COLUMN 25, TABLE 7 Cont'd
 After p125: "Leu-Leu-Asp-Leu-Leu-Asp" should read--Leu-Leu-Asp--;
 After p188: "Gly-Glu-Glu" should read --Gly-Gln-Glu-Glu--;
 After p106: "(SEQ ID NO. 63)" should read --(SEQ ID NO. 62)--;
 After p107: "(SEQ ID NO. 64)" should read --(SEQ ID NO. 63)--;
 After p108: "(SEQ ID NO. 65)" should read --(SEQ ID NO. 64)--;
 After p109: "(SEQ ID NO. 66)" should read --(SEQ ID NO. 65)--;
 After p110: "(SEQ ID NO. 67)" should read --(SEQ ID NO. 66)--;
 After p111: "(SEQ ID NO. 68)" should read --(SEQ ID NO. 67)--;
```

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 25, TABLE 7 Cont'd.
```
 After p188: "(SEQ ID NO. 69)" should read --(SEQ ID NO. 68)--;
 After p94:  "(SEQ ID NO. 70)" should read --(SEQ ID NO. 69)--;
 After p95:  "(SEQ ID NO. 71)" should read --(SEQ ID NO. 70)--;
 After p96:  "(SEQ ID NO. 72)" should read --(SEQ ID NO. 71)--;
 After p97:  "(SEQ ID NO. 73)" should read --(SEQ ID NO. 72)--;
 After p98:  "(SEQ ID NO. 74)" should read --(SEQ ID NO. 73)--;
 After p99:  "(SEQ ID NO. 75)" should read --(SEQ ID NO. 74)--;
```

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 25, TABLE 7 Cont'd.
```
 After p100: "(SEQ ID NO. 76)" should read --(SEQ ID NO. 75)--;
 After p101: "(SEQ ID NO. 77)" should read --(SEQ ID NO. 76)--;
 After p102: "(SEQ ID NO. 78)" should read --(SEQ ID NO. 77)--; and
 After p103: "(SEQ ID NO. 79)" should read --(SEQ ID NO. 78)--;.
```

COLUMN 27
  Line 51, on the line before "Clone:", --TABLE 10-- should be inserted.

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 28
  Line 2, on the line before "Results", --BINDING OF PEPTIDES TO AFFINITY PURIFIED HLA MOLECULES-- should be inserted;
  Line 46, on the line before "The binding", --TABLE 11-- should be inserted; and
  Line 54, "shown" should read --shown.--.

COLUMN 105
  Line 63, "6-11" should read --6-18--.

COLUMN 106
  Line 51, "7-25" should read --7-19--.

COLUMN 107
  Line 40, "1 25" should read --1-25--.

UNITED STATES PATENT AND TRADEMARK OFFICE
CERTIFICATE OF CORRECTION

PATENT NO. : 5,961,978

DATED : October 5, 1999

INVENTOR(S) : GUSTAV GAUDERNACK, ET AL.

It is certified that error appears in the above-identified patent and that said Letters Patent is hereby corrected as shown below:

COLUMN 109
 Line 50, "The" should read --the--.

COLUMN 110
 Line 65, "claim 89" should read --claim 90--.

Signed and Sealed this

Third Day of April, 2001

Attest:

NICHOLAS P. GODICI

*Attesting Officer*   Acting Director of the United States Patent and Trademark Office

SEQUENCE LISTING (1) GENERAL INFORMATION:

(iii) NUMBER OF SEQUENCES: 103

(2) INFORMATION FOR SEQ ID NO:1:

(i) SEQUENCE CHARACTERISTICS:
       (A) LENGTH: 16 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: internal (vi) ORIGINAL SOURCE:
       (A) ORGANISM: human (ix) FEATURE:
       (A) NAME/KEY: Peptide
       (B) LOCATION: 1..16
       (D) OTHER INFORMATION: /label= peptide
           /note= "p37, ras peptide"

(xi) SEQUENCE DESCRIPTION: SEQ ID NO:1:

Leu Val Val Val Gly Ala Gly Gly Val Gly Lys Ser Ala Leu Ala Leu
1               5                   10                  15

(2) INFORMATION FOR SEQ ID NO:2:

(i) SEQUENCE CHARACTERISTICS:
       (A) LENGTH: 16 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: internal (vi) ORIGINAL SOURCE:
       (A) ORGANISM: human (ix) FEATURE:
       (A) NAME/KEY: Peptide
       (B) LOCATION: 1..16
       (D) OTHER INFORMATION: /label= peptide
           /note= "p38, ras peptide"

(xi) SEQUENCE DESCRIPTION: SEQ ID NO:2:

Leu Val Val Val Gly Ala Asp Gly Val Gly Lys Ser Ala Leu Ala Leu
1               5                   10                  15

(2) INFORMATION FOR SEQ ID NO:3:

(i) SEQUENCE CHARACTERISTICS:
       (A) LENGTH: 16 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..16
            (D) OTHER INFORMATION: /label= peptide
                /note= "p39, ras peptide"

(xi) SEQUENCE DESCRIPTION: SEQ ID NO:3:

Leu Val Val Val Gly Ala Val Gly Val Gly Lys Ser Ala Leu Ala Leu
1               5                   10                  15

(2) INFORMATION FOR SEQ ID NO:4:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..16
            (D) OTHER INFORMATION: /label= peptide
                /note= "p40, ras peptide"

(xi) SEQUENCE DESCRIPTION: SEQ ID NO:4:

Leu Val Val Val Gly Ala Cys Gly Val Gly Lys Ser Ala Leu Ala Leu
1               5                   10                  15

(2) INFORMATION FOR SEQ ID NO:5:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..16
            (D) OTHER INFORMATION: /label= peptide
                /note= "p41, ras peptide"

(xi) SEQUENCE DESCRIPTION: SEQ ID NO:5:

Leu Val Val Val Gly Ala Ser Gly Val Gly Lys Ser Ala Leu Ala Leu
1               5                   10                  15

(2) INFORMATION FOR SEQ ID NO:6:

(i) SEQUENCE CHARACTERISTICS:
            (A) LENGTH: 16 amino acids
            (B) TYPE: amino acid
            (C) STRANDEDNESS: single
            (D) TOPOLOGY: linear

```
        (ii) MOLECULE TYPE: peptide (iii) HYPOTHETICAL: NO (v) FRAGMENT TYPE: internal (vi) ORIGINAL SOURCE:
             (A) ORGANISM: human (ix) FEATURE:
             (A) NAME/KEY: Peptide
             (B) LOCATION: 1..16
             (D) OTHER INFORMATION: /label= peptide
                 /note= "p42, ras peptide"

(xi) SEQUENCE DESCRIPTION: SEQ ID NO:6:

Leu Val Val Val Gly Ala Lys Gly Val Gly Lys Ser Ala Leu Ala Leu
1               5                  10                  15

(2) INFORMATION FOR SEQ ID NO:7:

(i) SEQUENCE CHARACTERISTICS:
             (A) LENGTH: 16 amino acids
             (B) TYPE: amino acid
             (C) STRANDEDNESS: single
             (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: human (ix) FEATURE:
             (A) NAME/KEY: Peptide
             (B) LOCATION: 1..16
             (D) OTHER INFORMATION: /label= peptide
                 /note= "p44, ras peptide"

(xi) SEQUENCE DESCRIPTION: SEQ ID NO:7:

Leu Val Val Val Gly Ala Arg Gly Val Gly Lys Ser Ala Leu Ala Leu
1               5                  10                  15

(2) INFORMATION FOR SEQ ID NO:8:

(i) SEQUENCE CHARACTERISTICS:
             (A) LENGTH: 16 amino acids
             (B) TYPE: amino acid
             (C) STRANDEDNESS: single
             (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: human (ix) FEATURE:
             (A) NAME/KEY: Peptide
             (B) LOCATION: 1..16
             (D) OTHER INFORMATION: /label= peptide
                 /note= "p45, ras peptide"

(xi) SEQUENCE DESCRIPTION: SEQ ID NO:8:

Leu Val Val Val Gly Ala Ala Gly Val Gly Lys Ser Ala Leu Ala Leu
1               5                  10                  15
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..16
        (D) OTHER INFORMATION: /label= peptide
            /note= "p43, ras peptide"

(xi) SEQUENCE DESCRIPTION: SEQ ID NO:9:

```
Leu Val Val Val Gly Ala Gly Val Val Gly Lys Ser Ala Leu Ala Leu
1               5                  10                  15
```

(2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..16
        (D) OTHER INFORMATION: /label= peptide
            /note= "p46, ras peptide"

(xi) SEQUENCE DESCRIPTION: SEQ ID NO:10:

```
Leu Val Val Val Gly Ala Gly Asp Val Gly Lys Ser Ala Leu Ala Leu
1               5                  10                  15
```

(2) INFORMATION FOR SEQ ID NO:11:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..16
        (D) OTHER INFORMATION: /label= peptide
            /note= "p22, ras peptide"

(xi) SEQUENCE DESCRIPTION: SEQ ID NO:11:

Asp Ile Leu Asp Thr Ala Gly Gln Glu Glu Tyr Ser Ala Met Arg Asp
1               5                   10                  15

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..16
        (D) OTHER INFORMATION: /label= peptide
            /note= "p20, ras peptide"

(xi) SEQUENCE DESCRIPTION: SEQ ID NO:12:

Asp Ile Leu Asp Thr Ala Gly Arg Glu Glu Tyr Ser Ala Met Arg Asp
1               5                   10                  15

(2) INFORMATION FOR SEQ ID NO:13:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..16
        (D) OTHER INFORMATION: /label= peptide
            /note= "p21, ras peptide"

(xi) SEQUENCE DESCRIPTION: SEQ ID NO:13:

Asp Ile Leu Asp Thr Ala Gly Lys Glu Glu Tyr Ser Ala Met Arg Asp
1               5                   10                  15

(2) INFORMATION FOR SEQ ID NO:14:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:

(A) ORGANISM: human (ix) FEATURE:
         (A) NAME/KEY: Peptide
         (B) LOCATION: 1..16
         (D) OTHER INFORMATION: /label= peptide
             /note= "p23, ras peptide"

(xi) SEQUENCE DESCRIPTION: SEQ ID NO:14:

Asp Ile Leu Asp Thr Ala Gly Leu Glu Glu Tyr Ser Ala Met Arg Asp
1               5                  10                  15

(2) INFORMATION FOR SEQ ID NO:15:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..16
         (D) OTHER INFORMATION: /label= peptide
             /note= "p24, ras peptide"

(xi) SEQUENCE DESCRIPTION: SEQ ID NO:15:

Asp Ile Leu Asp Thr Ala Gly His Glu Glu Tyr Ser Ala Met Arg Asp
1               5                  10                  15

(2) INFORMATION FOR SEQ ID NO:16:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..15
         (D) OTHER INFORMATION: /label= peptide
             /note= "p169, ras peptide"

(xi) SEQUENCE DESCRIPTION: SEQ ID NO:16:

Leu Asp Ile Leu Asp Thr Ala Gly Leu Glu Glu Phe Gly Ala Met
1               5                  10                  15

(2) INFORMATION FOR SEQ ID NO:17:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..14
            (D) OTHER INFORMATION: /label= peptide
                /note= "p74, ras peptide"

(xi) SEQUENCE DESCRIPTION: SEQ ID NO:17:

Leu Val Val Val Gly Ala Ala Gly Val Gly Lys Ser Ala Leu
1               5                  10

(2) INFORMATION FOR SEQ ID NO:18:

(i) SEQUENCE CHARACTERISTICS:
             (A) LENGTH: 14 amino acids
             (B) TYPE: amino acid
             (C) STRANDEDNESS: single
             (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..14
            (D) OTHER INFORMATION: /label= peptide
                /note= "p75, ras peptide"

(xi) SEQUENCE DESCRIPTION: SEQ ID NO:18:

Leu Val Val Val Gly Ala Ala Gly Val Gly Lys Ser Ala Leu
1               5                  10

(2) INFORMATION FOR SEQ ID NO:19:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..12
            (D) OTHER INFORMATION: /label= peptide
                /note= "p76, ras peptide"

(xi) SEQUENCE DESCRIPTION: SEQ ID NO:19:

Leu Val Val Val Gly Ala Ala Gly Val Gly Lys Ser
1               5                  10

(2) INFORMATION FOR SEQ ID NO:20:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..11
            (D) OTHER INFORMATION: /label= peptide
                /note= "p77, ras peptide"

(xi) SEQUENCE DESCRIPTION: SEQ ID NO:20:

Leu Val Val Val Gly Ala Ala Gly Val Gly Lys
1               5                   10

(2) INFORMATION FOR SEQ ID NO:21:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..10
            (D) OTHER INFORMATION: /label= peptide
                /note= "p78, ras peptide"

(xi) SEQUENCE DESCRIPTION: SEQ ID NO:21:

Leu Val Val Val Gly Ala Ala Gly Val Gly
1               5                   10

(2) INFORMATION FOR SEQ ID NO:22:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..15
            (D) OTHER INFORMATION: /label= peptide
                /note= "p69, ras peptide"

(xi) SEQUENCE DESCRIPTION: SEQ ID NO:22:

Val Val Val Gly Ala Ala Gly Val Gly Lys Ser Ala Leu Ala Leu
1               5                   10                  15

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..14
        (D) OTHER INFORMATION: /label= peptide
            /note= "p70, ras peptide"

(xi) SEQUENCE DESCRIPTION: SEQ ID NO:23:

Val Val Gly Ala Ala Gly Val Gly Lys Ser Ala Leu Ala Leu
1               5                   10

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..13
        (D) OTHER INFORMATION: /label= peptide
            /note= "p71, ras peptide"

(xi) SEQUENCE DESCRIPTION: SEQ ID NO:24:

Val Gly Ala Ala Gly Val Gly Lys Ser Ala Leu Ala Leu
1               5                   10

(2) INFORMATION FOR SEQ ID NO:25:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human

```
        (ix) FEATURE:
              (A) NAME/KEY: Peptide
              (B) LOCATION: 1..12
              (D) OTHER INFORMATION: /label= peptide
                   /note= "p72, ras peptide"

(xi) SEQUENCE DESCRIPTION: SEQ ID NO:25:

Gly Ala Ala Gly Val Gly Lys Ser Ala Leu Ala Leu
1               5                  10

(2) INFORMATION FOR SEQ ID NO:26:

(i) SEQUENCE CHARACTERISTICS:
              (A) LENGTH: 11 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (vi) ORIGINAL SOURCE:
              (A) ORGANISM: human (ix) FEATURE:
              (A) NAME/KEY: Peptide
              (B) LOCATION: 1..11
              (D) OTHER INFORMATION: /label= peptide
                   /note= "p73, ras peptide"

(xi) SEQUENCE DESCRIPTION: SEQ ID NO:26:

Ala Ala Gly Val Gly Lys Ser Ala Leu Ala Leu
1               5                  10

(2) INFORMATION FOR SEQ ID NO:27:

(i) SEQUENCE CHARACTERISTICS:
              (A) LENGTH: 10 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (vi) ORIGINAL SOURCE:
              (A) ORGANISM: human (ix) FEATURE:
              (A) NAME/KEY: Peptide
              (B) LOCATION: 1..10
              (D) OTHER INFORMATION: /label= peptide
                   /note= "p88, ras peptide"

(xi) SEQUENCE DESCRIPTION: SEQ ID NO:27:

Val Val Gly Ala Ala Gly Val Gly Lys Ser
1               5                  10

(2) INFORMATION FOR SEQ ID NO:28:

(i) SEQUENCE CHARACTERISTICS:
              (A) LENGTH: 11 amino acids
              (B) TYPE: amino acid
              (C) STRANDEDNESS: single
              (D) TOPOLOGY: linear (ii) MOLECULE TYPE: peptide
```

(iii) HYPOTHETICAL: NO (v) FRAGMENT TYPE: internal (vi) ORIGINAL SOURCE:
             (A) ORGANISM: human (ix) FEATURE:
             (A) NAME/KEY: Peptide
             (B) LOCATION: 1..11
             (D) OTHER INFORMATION: /label= peptide
                 /note= "p89, ras peptide"

(xi) SEQUENCE DESCRIPTION: SEQ ID NO:28:

Val Val Val Gly Ala Ala Gly Val Gly Lys Ser
1               5                  10

(2) INFORMATION FOR SEQ ID NO:29:

(i) SEQUENCE CHARACTERISTICS:
             (A) LENGTH: 11 amino acids
             (B) TYPE: amino acid
             (C) STRANDEDNESS: single
             (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: human (ix) FEATURE:
             (A) NAME/KEY: Peptide
             (B) LOCATION: 1..11
             (D) OTHER INFORMATION: /label= peptide
                 /note= "p90, ras peptide"

(xi) SEQUENCE DESCRIPTION: SEQ ID NO:29:

Val Val Gly Ala Ala Gly Val Gly Lys Ser Ala
1               5                  10

(2) INFORMATION FOR SEQ ID NO:30:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: human (ix) FEATURE:
             (A) NAME/KEY: Peptide
             (B) LOCATION: 1..12
             (D) OTHER INFORMATION: /label= peptide
                 /note= "p91, ras peptide"

(xi) SEQUENCE DESCRIPTION: SEQ ID NO:30:

Val Val Val Gly Ala Ala Gly Val Gly Lys Ser Ala
1               5                  10

(2) INFORMATION FOR SEQ ID NO:31:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..14
            (D) OTHER INFORMATION: /label= peptide
                /note= "p79, ras peptide"

(xi) SEQUENCE DESCRIPTION: SEQ ID NO:31:

Leu Val Val Val Gly Ala Gly Val Val Gly Lys Ser Ala Leu
1               5                   10

(2) INFORMATION FOR SEQ ID NO:32:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..13
            (D) OTHER INFORMATION: /label= peptide
                /note= "p80, ras peptide"

(xi) SEQUENCE DESCRIPTION: SEQ ID NO:32:

Leu Val Val Val Gly Ala Gly Val Val Gly Lys Ser Ala
1               5                   10

(2) INFORMATION FOR SEQ ID NO:33:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..12
            (D) OTHER INFORMATION: /label= peptide
                /note= "p81, ras peptide"

(xi) SEQUENCE DESCRIPTION: SEQ ID NO:33:

```
Leu Val Val Val Gly Ala Gly Val Val Gly Lys Ser
1               5                   10
```

(2) INFORMATION FOR SEQ ID NO:34:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..11
        (D) OTHER INFORMATION: /label= peptide
            /note= "p82, ras peptide"

(xi) SEQUENCE DESCRIPTION: SEQ ID NO:34:

```
Leu Val Val Val Gly Ala Gly Val Val Gly Lys
1               5                   10
```

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..10
        (D) OTHER INFORMATION: /label= peptide
            /note= "p83, ras peptide"

(xi) SEQUENCE DESCRIPTION: SEQ ID NO:35:

```
Leu Val Val Val Gly Ala Gly Val Val Gly
1               5                   10
```

(2) INFORMATION FOR SEQ ID NO:36:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
              (A) NAME/KEY: Peptide
              (B) LOCATION: 1..15
              (D) OTHER INFORMATION: /label= peptide
                  /note= "p64, ras peptide"

(xi) SEQUENCE DESCRIPTION: SEQ ID NO:36:

Val Val Val Gly Ala Gly Val Val Gly Lys Ser Ala Leu Ala Leu
1               5                  10                  15

(2) INFORMATION FOR SEQ ID NO:37:

(i) SEQUENCE CHARACTERISTICS:
              (A) LENGTH: 14 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (vi) ORIGINAL SOURCE:
              (A) ORGANISM: human (ix) FEATURE:
              (A) NAME/KEY: Peptide
              (B) LOCATION: 1..14
              (D) OTHER INFORMATION: /label= peptide
                  /note= "p65, ras peptide"

(xi) SEQUENCE DESCRIPTION: SEQ ID NO:37:

Val Val Gly Ala Gly Val Val Gly Lys Ser Ala Leu Ala Leu
1               5                  10

(2) INFORMATION FOR SEQ ID NO:38:

(i) SEQUENCE CHARACTERISTICS:
              (A) LENGTH: 13 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (vi) ORIGINAL SOURCE:
              (A) ORGANISM: human (ix) FEATURE:
              (A) NAME/KEY: Peptide
              (B) LOCATION: 1..13
              (D) OTHER INFORMATION: /label= peptide
                  /note= "p66, ras peptide"

(xi) SEQUENCE DESCRIPTION: SEQ ID NO:38:

Val Gly Ala Gly Val Val Gly Lys Ser Ala Leu Ala Leu
1               5                  10

(2) INFORMATION FOR SEQ ID NO:39:

(i) SEQUENCE CHARACTERISTICS:
              (A) LENGTH: 12 amino acids
              (B) TYPE: amino acid
              (C) STRANDEDNESS: single
              (D) TOPOLOGY: linear (ii) MOLECULE TYPE: peptide

```
        (iii) HYPOTHETICAL: NO (v) FRAGMENT TYPE: internal (vi) ORIGINAL SOURCE:
              (A) ORGANISM: human (ix) FEATURE:
              (A) NAME/KEY: Peptide
              (B) LOCATION: 1..12
              (D) OTHER INFORMATION: /label= peptide
                  /note= "p67, ras peptide"

(xi) SEQUENCE DESCRIPTION: SEQ ID NO:39:

Gly Ala Gly Val Val Gly Lys Ser Ala Leu Ala Leu
1               5                  10

(2) INFORMATION FOR SEQ ID NO:40:

(i) SEQUENCE CHARACTERISTICS:
              (A) LENGTH: 11 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (vi) ORIGINAL SOURCE:
              (A) ORGANISM: human (ix) FEATURE:
              (A) NAME/KEY: Peptide
              (B) LOCATION: 1..11
              (D) OTHER INFORMATION: /label= peptide
                  /note= "p68, ras peptide"

(xi) SEQUENCE DESCRIPTION: SEQ ID NO:40:

Ala Gly Val Val Gly Lys Ser Ala Leu Ala Leu
1               5                  10

(2) INFORMATION FOR SEQ ID NO:41:

(i) SEQUENCE CHARACTERISTICS:
              (A) LENGTH: 13 amino acids
              (B) TYPE: amino acid
              (C) STRANDEDNESS: single
              (D) TOPOLOGY: linear (ii) MOLECULE TYPE: peptide (iii) HYPOTHETICAL: NO (v) FRAGMENT TYPE: internal (vi) ORIGINAL SOURCE:
              (A) ORGANISM: human (ix) FEATURE:
              (A) NAME/KEY: Peptide
              (B) LOCATION: 1..13
              (D) OTHER INFORMATION: /label= peptide
                  /note= "p140, ras peptide"

(xi) SEQUENCE DESCRIPTION: SEQ ID NO:41:

Leu Val Val Val Gly Ala Arg Gly Val Gly Lys Ser Ala
1               5                  10

(2) INFORMATION FOR SEQ ID NO:42:

(i) SEQUENCE CHARACTERISTICS:
```

(A) LENGTH: 12 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..12
            (D) OTHER INFORMATION: /label= peptide
                /note= "p142, ras peptide"

(xi) SEQUENCE DESCRIPTION: SEQ ID NO:42:

Leu Val Val Val Gly Ala Arg Gly Val Gly Lys Ser
1               5                   10

(2) INFORMATION FOR SEQ ID NO:43:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..11
            (D) OTHER INFORMATION: /label= peptide
                /note= "p141, ras peptide"

(xi) SEQUENCE DESCRIPTION: SEQ ID NO:43:

Leu Val Val Val Gly Ala Arg Gly Val Gly Lys
1               5                   10

(2) INFORMATION FOR SEQ ID NO:44:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..13
            (D) OTHER INFORMATION: /label= peptide
                /note= "p143, ras peptide"

(xi) SEQUENCE DESCRIPTION: SEQ ID NO:44:

```
Leu Val Val Val Gly Ala Lys Gly Val Gly Lys Ser Ala
1               5                   10
```

(2) INFORMATION FOR SEQ ID NO:45:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..12
        (D) OTHER INFORMATION: /label= peptide
            /note= "p144, ras peptide"

(xi) SEQUENCE DESCRIPTION: SEQ ID NO:45:

```
Leu Val Val Val Gly Ala Lys Gly Val Gly Lys Ser
1               5                   10
```

(2) INFORMATION FOR SEQ ID NO:46:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..11
        (D) OTHER INFORMATION: /label= peptide
            /note= "p145, ras peptide"

(xi) SEQUENCE DESCRIPTION: SEQ ID NO:46:

```
Leu Val Val Val Gly Ala Lys Gly Val Gly Lys
1               5                   10
```

(2) INFORMATION FOR SEQ ID NO:47:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:

(A) NAME/KEY: Peptide
        (B) LOCATION: 1..15
        (D) OTHER INFORMATION: /label= peptide
            /note= "p154, ras peptide"

(xi) SEQUENCE DESCRIPTION: SEQ ID NO:47:

Val Val Val Gly Ala Lys Gly Val Gly Lys Ser Ala Leu Ala Leu
1               5                  10                  15

(2) INFORMATION FOR SEQ ID NO:48:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..14
        (D) OTHER INFORMATION: /label= peptide
            /note= "p155, ras peptide"

(xi) SEQUENCE DESCRIPTION: SEQ ID NO:48:

Val Val Gly Ala Arg Gly Val Gly Lys Ser Ala Leu Ala Leu
1               5                  10

(2) INFORMATION FOR SEQ ID NO:49:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..15
        (D) OTHER INFORMATION: /label= peptide
            /note= "p156, ras peptide"

(xi) SEQUENCE DESCRIPTION: SEQ ID NO:49:

Val Val Val Gly Ala Arg Gly Val Gly Lys Ser Ala Leu Ala Leu
1               5                  10                  15

(2) INFORMATION FOR SEQ ID NO:50:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..14
            (D) OTHER INFORMATION: /label= peptide
                /note= "p157, ras peptide"

(xi) SEQUENCE DESCRIPTION: SEQ ID NO:50:

Val Val Gly Ala Arg Gly Val Gly Lys Ser Ala Leu Ala Leu
1               5                   10

(2) INFORMATION FOR SEQ ID NO:51:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..10
            (D) OTHER INFORMATION: /label= peptide
                /note= "p177, ras peptide"

(xi) SEQUENCE DESCRIPTION: SEQ ID NO:51:

Leu Val Val Val Gly Ala Arg Gly Val Gly
1               5                   10

(2) INFORMATION FOR SEQ ID NO:52:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..9
            (D) OTHER INFORMATION: /label= peptide
                /note= "p178, ras peptide"

(xi) SEQUENCE DESCRIPTION: SEQ ID NO:52:

Leu Val Val Val Gly Ala Arg Gly Val
1               5

(2) INFORMATION FOR SEQ ID NO:53:

(i) SEQUENCE CHARACTERISTICS:
            (A) LENGTH: 10 amino acids (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..10
            (D) OTHER INFORMATION: /label= peptide
                /note= "p179, ras peptide"

(xi) SEQUENCE DESCRIPTION: SEQ ID NO:53:

Leu Val Val Val Gly Ala Lys Gly Val Gly
1               5                   10

(2) INFORMATION FOR SEQ ID NO:54:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..9
            (D) OTHER INFORMATION: /label= peptide
                /note= "p180, ras peptide"

(xi) SEQUENCE DESCRIPTION: SEQ ID NO:54:

Leu Val Val Val Gly Ala Lys Gly Val
1               5

(2) INFORMATION FOR SEQ ID NO:55:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..13
            (D) OTHER INFORMATION: /label= peptide
                /note= "p181, ras peptide"

(xi) SEQUENCE DESCRIPTION: SEQ ID NO:55:

Val Gly Ala Lys Gly Val Gly Lys Ser Ala Leu Ala Leu

```
1               5                    10
```

(2) INFORMATION FOR SEQ ID NO:56:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..12
        (D) OTHER INFORMATION: /label= peptide
            /note= "p182, ras peptide"

(xi) SEQUENCE DESCRIPTION: SEQ ID NO:56:

```
Gly Ala Lys Gly Val Gly Lys Ser Ala Leu Ala Leu
1               5                   10
```

(2) INFORMATION FOR SEQ ID NO:57:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..26
        (D) OTHER INFORMATION: /label= peptide
            /note= "amino acids 1-26 of p21 h-, k- and n-ras"

(xi) SEQUENCE DESCRIPTION: SEQ ID NO:57:

```
Met Thr Glu Tyr Lys Leu Val Val Val Gly Ala Gly Gly Val Gly Lys
1               5                   10                  15

Ser Ala Leu Thr Ile Gln Leu Ile Gln Asn
            20                  25
```

(2) INFORMATION FOR SEQ ID NO:58:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
    (A) NAME/KEY: Peptide
    (B) LOCATION: 1..28
    (D) OTHER INFORMATION: /label= peptide
        /note= "amino acies 45-72 of p21 h-, k- and n-ras"

(xi) SEQUENCE DESCRIPTION: SEQ ID NO:58:

```
Val Ile Asp Gly Glu Thr Cys Leu Leu Asp Ile Leu Asp Thr Ala Gly
1               5                   10                  15

Gln Glu Glu Tyr Ser Ala Met Arg Asp Gln Tyr Met
            20                  25
```

(2) INFORMATION FOR SEQ ID NO:59:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..15
        (D) OTHER INFORMATION: /label= peptide
            /note= "p170, ras peptide"

(xi) SEQUENCE DESCRIPTION: SEQ ID NO:59:

```
Leu Asp Ile Leu Asp Thr Ala Gly Gln Glu Glu Phe Gly Ala Met
1               5                   10                  15
```

(2) INFORMATION FOR SEQ ID NO:60:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..19
        (D) OTHER INFORMATION: /label= peptide
            /note= "p124, ras peptide"

(xi) SEQUENCE DESCRIPTION: SEQ ID NO:60:

```
Glu Thr Cys Leu Leu Asp Ile Leu Asp Thr Ala Gly Leu Glu Glu Tyr
1               5                   10                  15

Ser Ala Met
```

(2) INFORMATION FOR SEQ ID NO:61:

(i) SEQUENCE CHARACTERISTICS:
        (A) LENGTH: 18 amino acids

-continued (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..18
        (D) OTHER INFORMATION: /label= peptide
            /note= "p125, ras peptide"

(xi) SEQUENCE DESCRIPTION: SEQ ID NO:61:

Thr Cys Leu Leu Asp Ile Leu Asp Thr Ala Gly Leu Glu Glu Tyr Ser
1               5                   10                  15

Ala Met (2) INFORMATION FOR SEQ ID NO:62:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..17
        (D) OTHER INFORMATION: /label= peptide
            /note= "p106, ras peptide"

(xi) SEQUENCE DESCRIPTION: SEQ ID NO:62:

Cys Leu Leu Asp Ile Leu Asp Thr Ala Gly Leu Glu Glu Tyr Ser Ala
1               5                   10                  15

Met (2) INFORMATION FOR SEQ ID NO:63:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..16
        (D) OTHER INFORMATION: /label= peptide
            /note= "jp107, ras peptide"

(xi) SEQUENCE DESCRIPTION: SEQ ID NO:63:

Leu Leu Asp Ile Leu Asp Thr Ala Gly Leu Glu Glu Tyr Ser Ala Met
1               5                   10                  15

(2) INFORMATION FOR SEQ ID NO:64:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: internal (vi) ORIGINAL SOURCE:
          (A) ORGANISM: human (ix) FEATURE:
          (A) NAME/KEY: Peptide
          (B) LOCATION: 1..15
          (D) OTHER INFORMATION: /label= peptide
              /note= "p108, ras peptide"

(xi) SEQUENCE DESCRIPTION: SEQ ID NO:64:

Leu Asp Ile Leu Asp Thr Ala Gly Leu Glu Glu Tyr Ser Ala Met
1               5                   10                  15

(2) INFORMATION FOR SEQ ID NO:65:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: internal (vi) ORIGINAL SOURCE:
          (A) ORGANISM: human (ix) FEATURE:
          (A) NAME/KEY: Peptide
          (B) LOCATION: 1..15
          (D) OTHER INFORMATION: /label= peptide
              /note= "p109, ras peptide"

(xi) SEQUENCE DESCRIPTION: SEQ ID NO:65:

Cys Leu Leu Asp Ile Leu Asp Thr Ala Gly Leu Glu Glu Tyr Ser
1               5                   10                  15

(2) INFORMATION FOR SEQ ID NO:66:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (iii) HYPOTHETICAL: NO (v) FRAGMENT TYPE: internal (vi) ORIGINAL SOURCE:

(A) ORGANISM: human (ix) FEATURE:
         (A) NAME/KEY: Peptide
         (B) LOCATION: 1..14
         (D) OTHER INFORMATION: /label= peptide
             /note= "p110, ras peptide"

(xi) SEQUENCE DESCRIPTION: SEQ ID NO:66:

Leu Leu Asp Ile Leu Asp Thr Ala Gly Leu Glu Glu Tyr Ser
1               5                  10

(2) INFORMATION FOR SEQ ID NO:67:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..13
         (D) OTHER INFORMATION: /label= peptide
             /note= "p111, ras peptide"

(xi) SEQUENCE DESCRIPTION: SEQ ID NO:67:

Leu Asp Ile Leu Asp Thr Ala Gly Leu Glu Glu Tyr Ser
1               5                  10

(2) INFORMATION FOR SEQ ID NO:68:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..14
         (D) OTHER INFORMATION: /label= peptide
             /note= "p188, ras peptide"

(xi) SEQUENCE DESCRIPTION: SEQ ID NO:68:

Asp Ile Leu Asp Thr Ala Gly Gln Glu Glu Tyr Ser Ala Met
1               5                  10

(2) INFORMATION FOR SEQ ID NO:69:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..15
            (D) OTHER INFORMATION: /label= peptide
                /note= "p94, ras peptide"

(xi) SEQUENCE DESCRIPTION: SEQ ID NO:69:

Ile Leu Asp Thr Ala Gly Leu Glu Glu Tyr Ser Ala Met Arg Asp
1               5                  10                  15

(2) INFORMATION FOR SEQ ID NO:70:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..14
            (D) OTHER INFORMATION: /label= peptide
                /note= "p95, ras peptide"

(xi) SEQUENCE DESCRIPTION: SEQ ID NO:70:

Leu Asp Thr Ala Gly Leu Glu Glu Tyr Ser Ala Met Arg Asp
1               5                  10

(2) INFORMATION FOR SEQ ID NO:71:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..13
            (D) OTHER INFORMATION: /label= peptide
                /note= "p96, ras peptide"

(xi) SEQUENCE DESCRIPTION: SEQ ID NO:71:

Asp Thr Ala Gly Leu Glu Glu Tyr Ser Ala Met Arg Asp
1               5                  10

(2) INFORMATION FOR SEQ ID NO:72:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..12
        (D) OTHER INFORMATION: /label= peptide
            /note= "p97, ras peptide"

(xi) SEQUENCE DESCRIPTION: SEQ ID NO:72:

Thr Ala Gly Leu Glu Glu Tyr Ser Ala Met Arg Asp
1               5                   10

(2) INFORMATION FOR SEQ ID NO:73:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..11
        (D) OTHER INFORMATION: /label= peptide
            /note= "p98, ras peptide"

(xi) SEQUENCE DESCRIPTION: SEQ ID NO:73:

Ala Gly Leu Glu Glu Tyr Ser Ala Met Arg Asp
1               5                   10

(2) INFORMATION FOR SEQ ID NO:74:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..15
        (D) OTHER INFORMATION: /label= peptide
            /note= "p99, ras peptide"

(xi) SEQUENCE DESCRIPTION: SEQ ID NO:74:

Asp Ile Leu Asp Thr Ala Gly Leu Glu Glu Tyr Ser Ala Met Arg
1               5                   10                  15

(2) INFORMATION FOR SEQ ID NO:75:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..14
        (D) OTHER INFORMATION: /label= peptide
            /note= "p100, ras peptide"

(xi) SEQUENCE DESCRIPTION: SEQ ID NO:75:

Asp Ile Leu Asp Thr Ala Gly Leu Glu Glu Tyr Ser Ala Met
1               5                   10

(2) INFORMATION FOR SEQ ID NO:76:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..13
        (D) OTHER INFORMATION: /label= peptide
            /note= "p101, ras peptide"

(xi) SEQUENCE DESCRIPTION: SEQ ID NO:76:

Asp Ile Leu Asp Thr Ala Gly Leu Glu Glu Tyr Ser Ala
1               5                   10

(2) INFORMATION FOR SEQ ID NO:77:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..12
        (D) OTHER INFORMATION: /label= peptide
            /note= "p102, ras peptide"

(xi) SEQUENCE DESCRIPTION: SEQ ID NO:77:

Asp Ile Leu Asp Thr Ala Gly Leu Glu Glu Tyr Ser
1               5                   10

(2) INFORMATION FOR SEQ ID NO:78:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..11
        (D) OTHER INFORMATION: /label= peptide
            /note= "p103, ras peptide"

(xi) SEQUENCE DESCRIPTION: SEQ ID NO:78:

Asp Ile Leu Asp Thr Ala Gly Leu Glu Glu Tyr
1               5                   10

(2) INFORMATION FOR SEQ ID NO:79:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..25
        (D) OTHER INFORMATION: /label= peptide
            /note= "p112, ras peptide"

(xi) SEQUENCE DESCRIPTION: SEQ ID NO:79:

Met Thr Glu Tyr Lys Leu Val Val Val Gly Ala Gly Gly Val Gly Lys
1               5                   10                  15

Ser Ala Leu Thr Ile Gln Leu Ile Gln
            20                  25

(2) INFORMATION FOR SEQ ID NO:80:

(i) SEQUENCE CHARACTERISTICS:
        (A) LENGTH: 25 amino acids
        (B) TYPE: amino acid
        (C) STRANDEDNESS: single (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..25
         (D) OTHER INFORMATION: /label= peptide
              /note= "p113, ras peptide"

(xi) SEQUENCE DESCRIPTION: SEQ ID NO:80:

Met Thr Glu Tyr Lys Leu Val Val Val Gly Ala Val Gly Val Gly Lys
1               5                  10                  15

Ser Ala Leu Thr Ile Gln Leu Ile Gln
            20                  25

(2) INFORMATION FOR SEQ ID NO:81:

(i) SEQUENCE CHARACTERISTICS:
         (A) LENGTH: 25 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..25
         (D) OTHER INFORMATION: /label= peptide
              /note= "p114, ras peptide"

(xi) SEQUENCE DESCRIPTION: SEQ ID NO:81:

Met Thr Glu Tyr Lys Leu Val Val Val Gly Ala Lys Gly Val Gly Lys
1               5                  10                  15

Ser Ala Leu Thr Ile Gln Leu Ile Gln
            20                  25

(2) INFORMATION FOR SEQ ID NO:82:

(i) SEQUENCE CHARACTERISTICS:
         (A) LENGTH: 25 amino acids
         (B) TYPE: amino acid
         (C) STRANDEDNESS: single
         (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..25
         (D) OTHER INFORMATION: /label= peptide
              /note= "p115, ras peptide"

(xi) SEQUENCE DESCRIPTION: SEQ ID NO:82:

Met Thr Glu Tyr Lys Leu Val Val Val Gly Ala Arg Gly Val Gly Lys
1               5                   10                  15

Ser Ala Leu Thr Ile Gln Leu Ile Gln
            20                  25

(2) INFORMATION FOR SEQ ID NO:83:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..25
        (D) OTHER INFORMATION: /label= peptide
            /note= "p116, ras peptide"

(xi) SEQUENCE DESCRIPTION: SEQ ID NO:83:

Met Thr Glu Tyr Lys Leu Val Val Val Gly Ala Ala Gly Val Gly Lys
1               5                   10                  15

Ser Ala Leu Thr Ile Gln Leu Ile Gln
            20                  25

(2) INFORMATION FOR SEQ ID NO:84:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..25
        (D) OTHER INFORMATION: /label= peptide
            /note= "p117, ras peptide"

(xi) SEQUENCE DESCRIPTION: SEQ ID NO:84:

Met Thr Glu Tyr Lys Leu Val Val Val Gly Ala Ser Gly Val Gly Lys
1               5                   10                  15

Ser Ala Leu Thr Ile Gln Leu Ile Gln
            20                  25

(2) INFORMATION FOR SEQ ID NO:85:

(i) SEQUENCE CHARACTERISTICS:
        (A) LENGTH: 25 amino acids
        (B) TYPE: amino acid
        (C) STRANDEDNESS: single

```
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..25
            (D) OTHER INFORMATION: /label= peptide
                  /note= "p118, ras peptide"

(xi) SEQUENCE DESCRIPTION: SEQ ID NO:85:

Met Thr Glu Tyr Lys Leu Val Val Val Gly Ala Cys Gly Val Gly Lys
1               5                  10                  15

Ser Ala Leu Thr Ile Gln Leu Ile Gln
              20                  25

(2) INFORMATION FOR SEQ ID NO:86:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..25
            (D) OTHER INFORMATION: /label= peptide
                  /note= "p119, ras peptide"

(xi) SEQUENCE DESCRIPTION: SEQ ID NO:86:

Met Thr Glu Tyr Lys Leu Val Val Val Gly Ala Asp Gly Val Gly Lys
1               5                  10                  15

Ser Ala Leu Thr Ile Gln Leu Ile Gln
              20                  25

(2) INFORMATION FOR SEQ ID NO:87:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..25
            (D) OTHER INFORMATION: /label= peptide
                  /note= "p120, ras peptide"
```

(xi) SEQUENCE DESCRIPTION: SEQ ID NO:87:

Met Thr Glu Tyr Lys Leu Val Val Val Gly Ala Gly Val Val Gly Lys
1               5                   10                  15

Ser Ala Leu Thr Ile Gln Leu Ile Gln
            20                  25

(2) INFORMATION FOR SEQ ID NO:88:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..25
        (D) OTHER INFORMATION: /label= peptide
            /note= "p121, ras peptide"

(xi) SEQUENCE DESCRIPTION: SEQ ID NO:88:

Met Thr Glu Tyr Lys Leu Val Val Val Gly Ala Gly Asp Val Gly Lys
1               5                   10                  15

Ser Ala Leu Thr Ile Gln Leu Ile Gln
            20                  25

(2) INFORMATION FOR SEQ ID NO:89:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..28
        (D) OTHER INFORMATION: /label= peptide
            /note= "p158, ras peptide"

(xi) SEQUENCE DESCRIPTION: SEQ ID NO:89:

Val Ile Asp Gly Glu Thr Cys Leu Leu Asp Ile Leu Asp Thr Ala Gly
1               5                   10                  15

Leu Glu Glu Tyr Ser Ala Met Arg Asp Gln Tyr Met
            20                  25

(2) INFORMATION FOR SEQ ID NO:90:

(i) SEQUENCE CHARACTERISTICS:
        (A) LENGTH: 28 amino acids
        (B) TYPE: amino acid
        (C) STRANDEDNESS: single (D) TOPOLOGY: linear (ii) MOLECULE TYPE: peptide (iii) HYPOTHETICAL: NO (v) FRAGMENT TYPE: internal (vi) ORIGINAL SOURCE:
                    (A) ORGANISM: human (ix) FEATURE:
                    (A) NAME/KEY: Peptide
                    (B) LOCATION: 1..28
                    (D) OTHER INFORMATION: /label= peptide
                              /note= "p166, ras peptide"

(xi) SEQUENCE DESCRIPTION: SEQ ID NO:90:

Val Ile Asp Gly Glu Thr Cys Leu Leu Asp Ile Leu Asp Thr Ala Gly
1               5                   10                  15

Arg Glu Glu Tyr Ser Ala Met Arg Asp Gln Tyr Met
            20                  25

(2) INFORMATION FOR SEQ ID NO:91:

(i) SEQUENCE CHARACTERISTICS:
                    (A) LENGTH: 28 amino acids
                    (B) TYPE: amino acid
                    (C) STRANDEDNESS: single
                    (D) TOPOLOGY: linear (ii) MOLECULE TYPE: peptide (iii) HYPOTHETICAL: NO (v) FRAGMENT TYPE: internal (vi) ORIGINAL SOURCE:
                    (A) ORGANISM: human (ix) FEATURE:
                    (A) NAME/KEY: Peptide
                    (B) LOCATION: 1..28
                    (D) OTHER INFORMATION: /label= peptide
                              /note= "p168, ras peptide"

(xi) SEQUENCE DESCRIPTION: SEQ ID NO:91:

Val Ile Asp Gly Glu Thr Cys Leu Leu Asp Ile Leu Asp Thr Ala Gly
1               5                   10                  15

Lys Glu Glu Tyr Ser Ala Met Arg Asp Gln Tyr Met
            20                  25

(2) INFORMATION FOR SEQ ID NO:92:

(i) SEQUENCE CHARACTERISTICS:
                    (A) LENGTH: 28 amino acids
                    (B) TYPE: amino acid
                    (C) STRANDEDNESS: single
                    (D) TOPOLOGY: linear (ii) MOLECULE TYPE: peptide (iii) HYPOTHETICAL: NO (v) FRAGMENT TYPE: internal (vi) ORIGINAL SOURCE:
                    (A) ORGANISM: human (ix) FEATURE:
                    (A) NAME/KEY: Peptide
                    (B) LOCATION: 1..28
                    (D) OTHER INFORMATION: /label= peptide
                              /note= "p167, ras peptide"

(xi) SEQUENCE DESCRIPTION: SEQ ID NO:92:

Val Ile Asp Gly Glu Thr Cys Leu Leu Asp Ile Leu Asp Thr Ala Gly
1               5                   10                  15

His Glu Glu Tyr Ser Ala Met Arg Asp Gln Tyr Met
            20                  25

(2) INFORMATION FOR SEQ ID NO:93:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..13
        (D) OTHER INFORMATION: /label= peptide
            /note= "p104, ras peptide"

(xi) SEQUENCE DESCRIPTION: SEQ ID NO:93:

Tyr Val Val Val Gly Ala Ala Gly Val Gly Lys Ser Ala
1               5                   10

(2) INFORMATION FOR SEQ ID NO:94:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..14
        (D) OTHER INFORMATION: /label= peptide
            /note= "p34, ras peptide"

(xi) SEQUENCE DESCRIPTION: SEQ ID NO:94:

Ser Gly Pro Leu Lys Ala Glu Ile Ala Gln Arg Leu Glu Tyr
1               5                   10

(2) INFORMATION FOR SEQ ID NO:95:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO

```
        (v) FRAGMENT TYPE: internal (vi) ORIGINAL SOURCE:
            (A) ORGANISM: human (ix) FEATURE:
            (A) NAME/KEY: Peptide
            (B) LOCATION: 1..20
            (D) OTHER INFORMATION: /label= peptide
                /note= "Bcr-Abl fusion protein peptide"

(xi) SEQUENCE DESCRIPTION: SEQ ID NO:95:

Ile Pro Leu Thr Ile Asn Lys Glu Glu Ala Leu Gln Arg Pro Val Ala
1               5                  10                  15

Ser Asp Phe Glu
            20

(2) INFORMATION FOR SEQ ID NO:96:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..20
            (D) OTHER INFORMATION: /label= peptide
                /note= "second Bcr-Abl fusion protein peptide"

(xi) SEQUENCE DESCRIPTION: SEQ ID NO:96:

Ala Thr Gly Phe Lys Gln Ser Ser Lys Ala Leu Gln Arg Pro Val Ala
1               5                  10                  15

Ser Asp Phe Glu
            20

(2) INFORMATION FOR SEQ ID NO:97:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: human (ix) FEATURE:
            (A) NAME/KEY: Peptide
            (B) LOCATION: 1..16
            (D) OTHER INFORMATION: /label= peptide
                /note= "third Bcr-Abl fusion protein peptide"

(xi) SEQUENCE DESCRIPTION: SEQ ID NO:97:

Ala Phe Asp Val Lys Ala Leu Gln Arg Pro Val Ala Ser Asp Phe Glu
1               5                  10                  15
```

(2) INFORMATION FOR SEQ ID NO:98:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..15
        (D) OTHER INFORMATION: /label= peptide
            /note= "Ret fusion protein peptide"

(xi) SEQUENCE DESCRIPTION: SEQ ID NO:98:

```
Leu Arg Lys Ala Ser Val Thr Ile Glu Asp Pro Lys Trp Glu Phe
1               5                   10                  15
```

(2) INFORMATION FOR SEQ ID NO:99:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide
        (B) LOCATION: 1..17
        (D) OTHER INFORMATION: /label= peptide
            /note= "EGF receptor peptide"

(xi) SEQUENCE DESCRIPTION: SEQ ID NO:99:

```
Ser Arg Ala Leu Glu Glu Lys Lys Gly Asn Tyr Val Val Thr Asp His
1               5                   10                  15

Gly
```

(2) INFORMATION FOR SEQ ID NO:100:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: human (ix) FEATURE:
        (A) NAME/KEY: Peptide (B) LOCATION: 1..20
            (D) OTHER INFORMATION: /label= peptide
                /note= "Retinol receptor peptide"

(xi) SEQUENCE DESCRIPTION: SEQ ID NO:100:

Leu Ser Ser Cys Ile Thr Gln Gly Lys Ala Ile Glu Thr Gln Ser Ser
1               5                   10                  15

Ser Ser Glu Glu
            20

(2) INFORMATION FOR SEQ ID NO:101:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..10
         (D) OTHER INFORMATION: /label= peptide (xi) SEQUENCE DESCRIPTION: SEQ ID NO:101:

Val Val Val Gly Ala Arg Gly Val Gly Lys
1               5                   10

(2) INFORMATION FOR SEQ ID NO:102:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
         (A) ORGANISM: human (ix) FEATURE:
         (A) NAME/KEY: Peptide
         (B) LOCATION: 1..9
         (D) OTHER INFORMATION: /label= peptide (xi) SEQUENCE DESCRIPTION: SEQ ID NO:102:

Val Val Gly Ala Lys Gly Val Gly Lys
1               5

(2) INFORMATION FOR SEQ ID NO:103:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO

```
    (v) FRAGMENT TYPE: internal (vi) ORIGINAL SOURCE:
        (A) ORGANISM: human (ix) FEATURE:
        (A) NAME/KEY: Peptide
        (B) LOCATION: 1..10
        (D) OTHER INFORMATION: /label= peptide (xi) SEQUENCE DESCRIPTION: SEQ ID NO:103:

Val Val Gly Ala Gly Val Val Gly Lys Ser
1               5                   10
```